US008067632B2

(12) United States Patent
Wender et al.

(10) Patent No.: US 8,067,632 B2
(45) Date of Patent: Nov. 29, 2011

(54) PROCESS TO PRODUCE PROSTRATIN AND STRUCTURAL OR FUNCTIONAL ANALOGS THEREOF

(75) Inventors: Paul A. Wender, Menlo Park, CA (US); Jeffrey Warrington, Redwood City, CA (US); Jung-Min Kee, New York, NY (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 497 days.

(21) Appl. No.: 12/178,860

(22) Filed: Jul. 24, 2008

(65) Prior Publication Data
US 2009/0187046 A1 Jul. 23, 2009

Related U.S. Application Data

(60) Provisional application No. 60/962,020, filed on Jul. 26, 2007.

(51) Int. Cl.
*C07C 69/00* (2006.01)
(52) U.S. Cl. .................................................. 560/129
(58) Field of Classification Search .................. None
See application file for complete search history.

(56) References Cited

U.S. PATENT DOCUMENTS

| | | | |
|---|---|---|---|
| 3,710,795 A | 1/1973 | Higuchi | |
| 5,021,450 A | 6/1991 | Blumberg | |
| 5,145,842 A | 9/1992 | Driedger et al. | |
| 5,274,124 A | 12/1993 | Holton | |
| 5,405,875 A | 4/1995 | Blumberg et al. | |
| 5,420,162 A | 5/1995 | Blumberg et al. | |
| 5,430,160 A | 7/1995 | Holton | |
| 5,599,839 A * | 2/1997 | Boyd et al. ............. | 514/546 |
| 5,620,962 A | 4/1997 | Winget | |
| 5,643,948 A | 7/1997 | Driedger et al. | |
| 5,663,335 A | 9/1997 | Qi et al. | |
| 5,674,902 A | 10/1997 | Blumberg et al. | |
| 5,750,568 A | 5/1998 | Driedger et al. | |
| 5,767,095 A | 6/1998 | Winget | |
| 5,795,909 A | 8/1998 | Shashoua et al. | |
| 5,955,501 A * | 9/1999 | Driedger et al. ........ | 514/533 |
| 5,962,498 A | 10/1999 | Driedger et al. | |
| 6,080,784 A * | 6/2000 | Driedger et al. ........ | 514/546 |
| 6,200,969 B1 | 3/2001 | Fritz et al. | |
| 6,576,636 B2 | 6/2003 | Webb et al. | |
| 6,602,902 B2 | 8/2003 | Shashoua et al. | |
| 7,183,089 B2 | 2/2007 | Keasling et al. | |
| 7,199,151 B2 | 4/2007 | Shashoua et al. | |
| 2002/0010208 A1 | 1/2002 | Shashoua et al. | |
| 2003/0059471 A1 | 3/2003 | Compton et al. | |
| 2004/0180949 A1 | 9/2004 | Shashoua et al. | |
| 2005/0053977 A1 | 3/2005 | Greene et al. | |
| 2006/0018933 A1 | 1/2006 | Vaya et al. | |
| 2006/0018934 A1 | 1/2006 | Vaya et al. | |
| 2006/0024365 A1 | 2/2006 | Vaya et al. | |
| 2006/0079476 A1 | 4/2006 | Keasling et al. | |
| 2006/0216251 A1 | 9/2006 | Morariu | |
| 2007/0093462 A1 | 4/2007 | Rogers et al. | |
| 2007/0134653 A1 | 6/2007 | Greene et al. | |
| 2007/0212756 A1 | 9/2007 | Greene et al. | |
| 2007/0269379 A1 | 11/2007 | Mitragotri et al. | |
| 2008/0118494 A1 | 5/2008 | Kutsch et al. | |

FOREIGN PATENT DOCUMENTS

| | | |
|---|---|---|
| EP | 0531413 B1 | 8/1998 |
| EP | 0553107 B1 | 9/1999 |
| WO | 92/17064 A2 | 10/1992 |
| WO | 96/40614 A1 | 12/1996 |
| WO | 2007009055 A2 | 1/2007 |

OTHER PUBLICATIONS

Cashmore, A.R., et al., "The Structure of Prostratin: A Toxic Tetracyclic Diterpene Ester from Pimelea Prosstrata," Tetrahedron Letters, 1976, No. 20., 1737-1738.
Williams, Samuel A., et al., "Prostratin Antagonizes HIV Latency by Activating NF-KB," The Journal of Biological Chemistry, Oct. 1, 2004, vol. 279, No. 40., 42008-42017.
Hezareh, Marjan, et al., "Mechanisms of HIV Receptor and Co-receptor Down-regulation by Prostratin: Role of Conventional and Novel PKC Isoforms," Antiviral Chemistry and Chemotherapy, 2004, 15:4, 207-222.
Gustafson, Kirk R., et al., "A Nonpromoting Phorbol from the Samoan Medicinal Plant Homalanthus nutans Inhibits Cell Killing by HIV-1," Journal of Medicinal Chemistry, 1992, vol. 35, No. 11, 1978-1986.
Rullas, Joaquin, et al., "Prostratin induces HIV activation and downregulates HIV receptors in peripheral blood lymphocytes," Antiviral Therapy, 2004, 9:545-554.
Kulkosky, Joseph, et al., "Prostratin: activation of latent HIV-1 expression suggests a potential inductive adjuvant therapy for HAART," Blood, Nov. 15, 2001, vol. 98, No. 10, 3006-3015.
Wender, Paul A., et al., "Conversion of Phorbol to 12-deoxy tiglianes and daphnanes including Prostratin and 12-deoxyphorbol-13phenylacetate (DPP)," Stanford University Department of Systems Biology, 1-14.
Wender, Paul A., et al., "Practical Synthesis of Prostratin, DPP, and Their Analogs, Adjuvant Leads Against Latent HIV," Science, May 2, 2008, vol. 320, 649-652.
Everts, Sarah, "Ferreting Out HIV," Chemical and Engineering News, May 5, 2008, vol. 86, No. 18, 11.
Wender, Paul A., et al., "Inspirations from Nature. New reactions, therapeutic leads, and drug delivery systems," Pure Appl. Chem., 2003, vol. 75, Nos. 2-3, 143-155.

(Continued)

*Primary Examiner* — Sudhakar Katakam
(74) *Attorney, Agent, or Firm* — David J. Aston; Peters Verny, LLP

(57) ABSTRACT

This invention concerns a process to convert a hydroxyl group (bold in $R_3C$—OH) in a tigliane-type compound to a hydrogen (bold in $R_3C$—H) to obtain deoxytigliane-type compounds or structural or functional analogs thereof. The process has wide application particularly to produce specific biologically active compounds in quantity for use as pharmaceuticals. In particular the process can be used to convert phorbol to a 12-deoxytigliane (prostrating which is a therapeutic lead for the treatment of AIDS. New compositions of matter are also disclosed.

32 Claims, 14 Drawing Sheets

OTHER PUBLICATIONS

Wender, Paul A., et al., "Efficient Synthetic Access to a New Family of Highly Potent Bryostatin Analogues via a Prins-Driven Macrocyclization Strategy," J. Am. Chem. Soc., 2008, vol. 130, No. 21, 6658-6659.

"Danishefsky Taxol total synthesis," http://en.wkipedia.org/wiki/Danishefsky_Taxol_total_synthesis, Jun. 27, 2007.

"Nicolaou Taxol total synthesis," http://en.wkipedia.org/wiki/Nicolaou_Taxol_total synthesis. Jun. 27, 2007.

Gschwendt, M., et al., "Tumor-promoting Compounds from Euphorbia Cooperi Di- and Triesthers of 16-Hydroxy-12-Desoxy-Phorbol," Biochemisches Institut, Duetsched Krebsforschungszentrum, Heidelberg, Germany, Tetrahedron Letters No. 8, 1970, 567-570.

07 AIDS epidemic update, UNAIDS and WHO, Dec. 2007, pp. 1-60.

Gulakowski, et al., "Antireplicative and anticytopathic activities of prostratin, a non-tumor-promoting phorbol ester, against human immunodeficiency virus (HIV)," Antiviral Research, 1997, 33 87-97.

Appendino, Giovanni, et al., "Synthesis and Biological Evaluation of Phorbol-Resiniferatoxin (RTX) Hybrids," Eur. J. Org. Chem., 2004, 3413-3421.

Kennedy, G. Davon, et al., "Thermolysis of Hexasubstituted-4,5-dihydro-3H-pyrazoles: Synthesis of 1-Alkoxy- and 1-Acetoxy-1,2,2,3,3- pentasubstituted-cyclopropanes," J. Heterocyclic Chem., Nov. 1991, vol. 28, 1773-1777.

Lee, Kwangho, et al., "Formal Synthesis of (+)-Phorbol," Department of Chemistry University of Alabama Tuscaloosa, Alabama, J. Am. Chem. Soc., 2001, vol. 123, No. 23, 5590-5591.

Azam, M. Mohibbe, et al., "Prospects and potential of fatty acid methyl esters of some non-traditional seed oils for use as biodiesel in India," Biomass and Bioenergy, 2005, 29, 293-302.

Kulkosky, Joseph, et al., "Expression of Latent HAART-Persistent HIV Type 1 Induced by Novel Cellular Activating Agents," AIDS Research and Human Retroviruses, 2004, vol. 20, No. 5, 497-505.

Quan-En Yang, "Eradication of HIV in infected patients: Some potential approaches," Med Sci Monit, 2004; 10(7): RA155-165.

Miana, G.A., et al., "Isolation of Prostratin from Euphorbia cornigera," Planta Medica, 1985, 353-354.

"Scientists discover a new compound that aids anti-HIV drugs," Future HIV Ther., 2008, 2(4) 316.

"Researchers' New Goal: Drug-free Remission for HIV Infection," ScienceDaily, Mar. 5, 2009, http://www.sciencedaily.com/releases/2009/03/090305141629.htm.

Witvrouw, Myriam, et al., "Potent and selective inhibition of HIV and SIV by prostratin interacting with viral entry," Antiviral Chemistry & Chemotherapy, 14:321-328.

Davis, B. R., et al., "Clemmensen Reduction. Part III. alpha beta-Unsaturated Ketones," J. Chem. SOC. (C), 1966 pp. 313-317.

Wender, Paul A., et al., "Studies on Tumor Promoters. 9. A Second-Generation Synthesis of Phorbol," J. Am. Chem. Soc., 1990, vol. 112, No. 12, 4956-4958.

Bowry, V. W., et al., "Kinetics of nitroxide radical trapping. 2. Structural effects," J. Am. Chem. SOC 1992, 114 (13), 4992-4996.

Danishefsky, Samuel J., et al., "Total Synthesis of Baccatin III and Taxol," J. Am. Chem. Soc., 1996, 118 (12), 2843-2859.

Wender, Paul A. et al., "The Pinene Path to Taxanes. 6. A Concise Stereocontrolled Synthesis of Taxol," J. Am. Chem. Soc., 1997, 119 (11), 2757-2758.

Morihira, Koichiro, et al., "Enantioselective Total Synthesis of Taxol," J. Am. Chem. Soc., 1998, 120 (49), 12980-12981.

Newman, David J., et al., "Natural Products as Sources of New Drugs over the Last 25 Years," J. Nat. Prod., 2007, 70 (3), 461-477.

Holton, Robert A., et al., "First total synthesis of taxol. 1. Functionalization of the B ring," J. Am. Chem. Soc., 1994, 116 (4), 1597-1598.

Wang, Yu-Bo, et al., "Diterpenoids from the Roots of Euphorbia fischeriana," Journal of Natural Products, 2006, vol. 69, No. 6, 967-970.

Nicolaou, K. C., et al., "Total Synthesis of Taxol," Nature, Feb. 17, 1994, vol. 367, 630-634.

Burdelya, Lyudmila G., et al., "An Agonist of Toll-Like Receptor 5 Has Radioprotective Activity in Mouse and Primate Models," Science, Apr. 11, 2008, vol. 320, 226-230.

Wender, Paul A., et al., "Studies on Tumor Promoters. 7. The Synthesis of a Potentially General Precursor of the Tiglianes, Daphnanes, and Ingenanes," J. Am. Chem. Soc., 1989, 111 , 8954-8957.

Wender, Paul A., et al., "Studies on Tumor Promoters. 8. The Synthesis of Phorbol," J. Am. Chem. SOC. 1989, 111, 8957-8958.

Cairnes, David A., et al., "A Rapid Method for Isolating Phorbol From Croton Oil," Cancer Letters, 1981, 14 85-91.

Wender, Paul A., et al., "The First Formal Asymmetric Synthesis of Phorbol," J. Am. Chem. Soc., 1997, 119, 7897-7898.

Bocklandt, Sven, et al., "Activation of latent HIV-1 expression by the potent anti-tumor promoter 12-deoxyphorbol 13-phenylacetate," Antiviral Research, 2003, 59, 89-98.

Kreibich, G., et al., "Uber einige Ather des Phorbols," Z. Naturforschg. Aug. 1968, 23 b, 1444-1452.

"Scientists discover a new compound that aids anti-HIV drugs," News in Brief, Expert Reviews of Anti-infective Therapy, 2008, 6(3), 278.

Johnson, Holly E., et al., "Variability in content of the anti-AIDS drug candidate Prostratin in Samoan populations of Homalanthus nutans (Euphorbiaceae)," Oral Presentation, 2007.

Alo B Duffy, "Shining some light on Prostratin discussion," file:///Users/PAW/Desktop/bryo.02/prostratin.original%20source%20new%20zealand.08.webarchive, Tuesday, Dec. 23, 2008 11:03, pp. 1-2.

Nature, Research Highlights, "Flushing Out HIV," Science 320, 649-652 (2008), vol. 453, May 8, 2008.

Bucci, Mirella, et al., "Prostratin in a snap," Research Highlights, Nature Chemical Biology, vol. 4, No. 6, Jun. 2008, p. 340.

Gary Stix, "Luring HIV from Hiding, The quest to kill the last traces of the virus secreted away in cells," Scientific American, May 13, 2008, http://www.sciam.com/article.cfm?id=luring-hiv-from-hiding &print=true, pp. 1-2.

Brief: Chemistry professor strives for HIV cure, The Stanford Daily, May 14, 2008, http://daily.stanford.edu/article/2008/5/14/briefChemistryProfessorStrivesForHivCure.

Korin, et al., "Effects of Prostratin on T-Cell Activation and Human Immunodeficiency Virus Latency," J. of Virology, Aug. 2002, vol. 76, No. 16, 8118-8123.

Warner, et al., "Propellanes. XV. Stereoselectivities of Cyclopropyl Radicals Generated Via Tin Hydride Reduction," Tetrahedron Letters, 1976, No. 51, 4665-4668.

Szallasi, et al., "Nonpromoting 12-Deoxyphorbol 13-Esters Inhibit Phorbol 12-Myristate 13-Acetate Induced Tumor Promotion in CD-1 Mouse Skin," Cancer Research, Jun. 1, 1993, 53, 2507-2512.

Blankson, et al., "The Challenge of Viral Reservoirs in HIV-1 Infection," Annual Review of Medicine, 2002, 53, pp. 557-593.

Freeman, Jeremiah P., "A Synthesis of Cyclopropyl Acetates," Journal of Organic Chemistry, Jun. 1964, vol. 29, 1379-1382.

Baumstark, A. L., et al., "Oxygen-Atom Transfer Reagents: New, Reactive alpha-Azohydroperoxides," Tetrahedron Letters, 1987, vol. 28, No. I8, 1963-1966.

Abushanab, et al., "Synthesis, Carbon-13 Nuclear Magnetic Resonance, and Mass Spectral Studies of 3-Aroyloxy-3,5,5-trimethyl-l-pyrazoline N-Oxides," J.Org. Chem., 1978, vol. 43, No. 10, 2017-2020.

Molchanov, et al., Reactions of Substituted Ethyl 1,2,3,4,4',5'-Hexahydrospiro-[naphthalene-2,5'-pyrazole]-3'-carboxylates with Halogens, Russian Journal of Organic Chemistry vol. 41 No. 7 2005, pp. 1036-1042. Translated from Zhurnal Organicheskoi Khimii, vol. 41, No. 7, 2005, pp. 1058-1063.

Stay, et al., Samoa Mamala & Prostratin Recommendations: Pharmaceutical Plant Proposal, Jun. 23, 2008, pp. 1-28.

Haas, Michael J., "Barking up the right tree," SciBX, May 15, 2008, vol. 1, No. 16, 9-10.

Richard Van Noorden, Synthesis boost for HIV research, Royal Society of Chemistry, Chemistry World, May 2, 2008, http://www.rsc.org/chemistryworld/News/2008/May/02050801.asp.

Mukaiyama, et al., "Asymmetric Total Synthesis of Taxol," Chem. Eur. J. 1999, 5, No. 1, pp. 121-161.

* cited by examiner

Prostratin
(12-deoxyphorbol-13-acetate)

Phorbol    Prostratin eg.

↓ very rapid rapid fragmentation products such as:

PROCESS TO PRODUCE PROSTRATIN AND STRUCTURAL OR FUNCTIONAL ANALOGS THEREOF

CROSS-REFERENCE TO RELATED APPLICATIONS

This application claims priority from U.S. Provisional Patent Application No. 60/962,020 filed on Jul. 26, 2007, which is hereby incorporated by reference in its entirety.

STATEMENT OF GOVERNMENTAL SUPPORT

This research was supported by the U.S. National Institutes of Health Grant #CA31841. The U.S. Government has certain rights in this invention.

REFERENCE TO SEQUENCE LISTING

None

BACKGROUND OF THE INVENTION

1. Field of the Invention

This invention concerns a process to convert a hydroxyl group (bold in $R_3C$—OH) in a tigliane-type compound to a hydrogen (bold in $R_3C$—H) to obtain deoxytigliane-type compounds or structural or functional analogs thereof. The process has wide application particularly to produce specific biologically active compounds in quantity for use as pharmaceuticals. In particular the process can be used to convert phorbol to 12-deoxytiglianes (e.g., prostrating, which are therapeutic leads for the treatment of AIDS.

2. Description of the Problems and Related Art

Availability of Prostratin

In the treatment of disease, many therapies use components from natural sources or from synthetic modifications of natural products. Aspirin was found early in the bark of a willow tree. Many natural and non-natural beta-lactam antibiotics are produced from natural sources often by semi-synthesis from a common fermentation product.[1] Naturally-occurring and non-natural steroids used as therapeutics have been obtained directly or through semi-synthesis from plant sources.

More recently, taxol, an effective anti-cancer agent, was originally extracted from a natural resource, e.g., the bark and needles of the Western Yew, *Taxus brevifolia*. The total synthesis of taxol has been reported by the groups of Holton,[2,3] Wender,[4] Nicolaou,[5] Danishefsky,[6] Kuwajima,[7] and Mukaiyama.[8] While taxol is thus available through total synthesis, it has proven to be significantly more practical to produce it through semi-synthesis from a more readily available and structurally related plant natural product of the baccatin family. Semi-synthesis has also led to the production of non-natural taxanes like taxotere that have proven to be more effective in some therapeutic applications than the natural product taxol. A recent compilation of natural products as sources of new drugs indicates that a significant percentage of all new drugs introduced over the last 25 years were either natural products or derived from natural products through semi-synthesis.[1] Not unlike the examples cited above and references cited therein, prostratin is currently available only in low natural abundance from *Euphorbia cornigera*, *Homolanthus nutans* and other organisms.[9] Other approaches are being explored, but none has yet addressed supply. Thus, there is a need in the art for a new process for production of prostratin and structural or functional analogs thereof through semi-synthesis from readily available starting materials.

AIDS and the HIV Reservoir Problem

AIDS (acquired immune deficiency syndrome) is a pandemic disease caused by HIV (human immunodeficiency virus). In a recent report, UNAIDS (the Joint United Nations Programme on HIV/AIDS) estimated that 33.2 million people were living with HIV and 2.1 million people lost their lives to AIDS in the year 2007.[10]

HAART (highly active antiretroviral therapy) has been successful in decreasing HIV-I in the plasma to undetectable levels in many treated patients. However, latent virus reservoirs remain in patients even after HAART. Such latent virus reservoirs are not targeted by current drug treatments and slowly produce the active virus over time. Therefore, interruption of treatment on such patients often results in viral rebound at a later stage.

Because HAART treats only active virus, the latent virus reservoirs decrease only very slowly in patients on HAART. It is estimated that decades of treatment would be required to deplete the latent viral reservoirs. Such long treatment is undesirable due to the side effects arising from prolonged use of the required therapeutic agents, the expense associated with this chronic therapy, patient compliance concerns, and the eventual emergence of resistance to the chronically administered therapeutics by viral mutation. Therefore, agents that can controllably flush the latent virus from its reservoirs could, in principle, provide a means to eradicate the virus when used as adjuvants in combination with HAART[11].

Prostratin's Activity—A Potential Solution to the HIV Reservoir Problem

Prostratin (12-deoxyphorbol-13-acetate) (FIG. 1) is a tigliane diterpene first isolated from *Pimelea prostrata* and reported by Cashmore et al. in 1976.[12] In 1985, Miana et al. reported isolation of prostratin from *Euphorbia cornigera*.[13] More recently, prostratin has been found in limited quantities in the Western Samoan plant *Homalanthus nutans* and other organisms. FIG. 2 shows a photograph of *Homalanthus nutans* (left) and a Samoan healer preparing an extract from the bark of the Samoan mamala tree (right). Prostratin demonstrated multiple promising activities against HIV, which are described in the following sections.[14]

Prostratin Induces Activation of Latent HIV Virus.[15]

In latently infected CD4+ T cells, prostratin induces HIV gene expression. NF-κB and PKC (α and θ) activation are the key events triggered by prostratin. Although other phorbol esters such as PMA (phorbol 12-myristate-13-acetate) are also shown to activate latent HIV, prostratin differs markedly from these and offers distinct therapeutic value because it does not exhibit the tumor-promoting activity of these other agents. Therefore, prostratin is a promising therapeutic lead as an adjuvant to be used in HAART.

Prostratin Protects HIV-Infected Immune Cells from Cell Death

In an in vitro study, prostratin was shown to protect T-lymphoblastoid CEM-SS and C-8166 cell lines. At a prostratin concentration of approximately 1 μM, cell viability was restored to the level of uninfected controls, and no sign of cytotoxicity was observed up to about 25 μM. The mode of action is unclear, but the $K_i$ of prostratin for PKC is 12 nM, suggesting the involvement of PKC in the process.[14a]

Prostratin Inhibits HIV Invasion into Healthy Cells by Down-regulating the Expression of HIV Receptors on Cell Surfaces[16]

In CEM-SS and MT-4 cell lines, CD4 receptors were significantly reduced on cell surfaces, and mRNA array assay confirmed that CD4 gene expression along with other HIV-1 receptors (CXCR4 and CCR5) were downregulated in THP-1 cells. Staurosporine, a PKC inhibitor was shown to reverse the CD4 downregulation by prostratin, implying the involvement of PKC activation in the process. In addition, prostratin stimulates the internalization and subsequent degradation of CD4 and CXCR receptors in CEM cells. PKC translocation studies on this cell line showed PKCβ and PKCδ remained in the cytosol, whereas PKCα, τ, θ, and ε were effectively translocated to the plasma membrane.

In a more recent study, DPP (12-deoxyphorbol 13-phenylacetate), another non-tumor promoting phorbol ester, was reported to be 20-30 fold more potent than prostratin in activating latent HIV-1. DPP also downregulates CD4 and CXCR4 receptors at nanomolar concentrations.[17] As is true for many therapeutic agents, greater potency could lead to improved therapeutic potential. This invention also provides a process for the production of DPP and other structural or functional analogs that may have superior clinical activity.
Potential Use of Prostratin as a Protective Adjuvant in Anticancer Radiotherapy Activators of NF-kappaB pathway can protect healthy cells from the radiation during anticancer radiotherapy. In studies with mice and rhesus monkeys, the survival rate of the animals after radiation therapy was significantly improved when the NF-kappaB activators were injected to the animals.[18] Therefore, prostratin and its functional analogs, being NF-kappaB activators without the tumor-promotion effect, hold great promise as adjuvants in anticancer radiotherapy.
Prostratin's Supply—A Hurdle in Clinical Trials and Future Human Use Prostratin has most recently been extracted from the bark and stemwood of Samoan mamala tree (*Homalanthus nutans*). However, the isolation process requires multiple chromatographic separations (one Sephadex column chromatography and two HPLC purifications) and the isolation yield is very low (15 mg of prostratin from 1.05 kg of fresh stemwood).[14a] In addition, the prostratin content varies significantly between samples (0.2 μg/g to 52.6 μg/g).[19] Other natural sources have been identified but they too suffer from low prostratin content, seasonal variation in content, and difficult separation procedures. Therefore, based on existing natural product sources, it would be difficult to economically produce prostratin in large quantities needed for human clinical trials (50 mg per treatment session).[20] Such large scale harvest could place significant burden on the ecosystem. In addition, at present it is not clear that farmed trees could produce prostratin at the same levels as the wild type.

A research group at UC Berkeley signed an agreement with the Samoan government to use the mamala tree to identify and isolate the genes required to biosynthesize prostratin.[23] Their goal is to engineer bacteria by inserting the genes responsible for prostratin biosynthesis and produce prostratin by fermentation. However, this technology is still in its early development stage and its feasibility is yet to be demonstrated.

These limitations on supply account for the limited research that has been done on prostratin and DPP, and the paucity of improved analogs. Accordingly, a need exists to obtain quantities of synthetic materials for use in the control of diseases.

SPECIFIC PATENTS AND PUBLICATIONS

Patents of interest include but are not limited to: U.S. Pat. No. 5,145,842; U.S. Pat. No. 5,599,839; U.S. Pat. No. 5,643,948; U.S. Pat. No. 5,955,501; U.S. Pat. No. 6,080,784; and WO 96/40614, all of which are incorporated by reference in their entirety.

SUMMARY OF THE INVENTION

The present invention provides a process and platform for a variety of syntheses. Specifically, the conversion of phorbol to prostratin, DPP, and structural and functional analogs thereof provides for both larger quantities and diversity of material than are presently available for therapy from natural prostratin sources. The process also enables the preparation of new agents with tunable and improved therapeutic properties.

In one embodiment, the present invention concerns a process to produce a 12-deoxy tigliane-type compound or a structural or functional analog thereof of the formula:

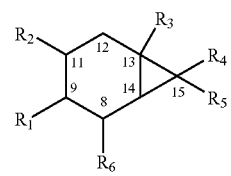

wherein $R_1$, $R_2$, $R_3$, $R_4$, $R_5$, and $R_6$ are each independently selected from the group consisting of hydrogen, alkyl (C1 to C15), cyclic alkyl (C3 to C15), aromatic ring, hydroxyl, carbonate, carbamate, ester, ether, thiol, amine, amide, guanidine or urea, wherein the $R_{1-6}$ groups may be straight-chained or branched, wherein the $R_{1-6}$ groups may comprise one or more heteroatoms including, but not limited to boron, nitrogen, oxygen, phosphorous, sulfur, silicon or selenium, and wherein $R_1$ and $R_6$ may be connected as in the case of 12-deoxy tigliane-type compounds, or may be disconnected as in the case of structural or functional analogs.

Preferably, $R_2$ is methyl, $R_3$ is an ester (—OC(O)Ak, where Ak is an alkyl chain), $R_4$ and $R_5$ are methyl groups, and $R_1$ and $R_6$ are connected by a 5 member alkyl chain as in the tigliane skeleton.

The process comprises:
a) contacting an enol derivative or a ketone at the position corresponding to C-13 of a compound that possesses partial or total structural features of C- and D-rings of a tigliane with hydrazine or an agent equivalent to hydrazine at a temperature between −20 and +150° C. for about 0.1 to about 72 hours;
b) contacting the product of step a with a solvent at approximately +20 to +250° C.;
c) contacting the product of step b with an oxidizing agent or nucleophilic agent in a solvent at between about −10 to +120° C. for approximately 0.1 to 72 hours;
d) 1) contacting the product of step c with light of a wavelength that is absorbed by the product in a solvent at between about −20 and +60° C. for between about 1 to 240 mm; or
2) contacting the product of step c with a solvent and heating between about +50 and +300° C. for between about 1 and 60 hours; or
3) contacting the product of step c with an excited state of a sensitizer formed by absorption of light by the sensitizer; or
4) contacting the product of step c with a metal or metal salt in a solvent at between about −80 and +110° C. for between about 1 and 48 hours; and
e) isolating the 12-deoxy tigliane-type compound or a structural or functional analog thereof.

In a preferred aspect of this embodiment, the 12-deoxy tigliane-type compound is prostratin or 12-deoxyphorbol-13-phenylacetate (DPP).

Step a) may be conducted in the presence of a base or acid, and may be followed by treatment with a base or hydrazine scavenger. Preferably, step a) is carried out with hydrazine hydrate in the presence of potassium carbonate, followed by acetic acid. In addition, the product of step a) may be treated with basic alumina.

Step b) may also be conducted in the presence of a base. Preferably, step b) is carried out in a mixture of N,N-diisopropyl ethylamine and toluene.

Preferably, the oxidizing agent in step c) is iodoso benzene diacetate (PhI(OAc)$_2$) or lead (IV) acetate. In addition, the oxidizing agent in step c) may be premixed with phenylacetic acid. Also preferably, the nucleophilic agent in step c is hydrogen cyanide.

Step c) may be conducted in the presence of carboxylic acids, alcohols, thiols, amines, halides, or combinations thereof. In one aspect of this embodiment, step c) is conducted in the presence of a mixture of carboxylic acids selected from the group consisting of primary alkyl, secondary alkyl, tertiary alkyl and aromatic organic carboxylic acids. Alternatively, or in addition, step c) may be conducted in the presence of a mixture of alcohols selected from the group consisting of primary alkyl, secondary alkyl, tertiary alkyl and aromatic alcohols. Preferably, the wavelength of light used in step d) is between 300 and 370 nm.

In one aspect of this embodiment, step c) is followed by:
contacting the product of step c) with a nucleophilic agent, an alcohol derivatizing agent or combinations thereof in a solvent at between −20 and +150° C. for between 0.1 and 72 hours or with an acid, base, oxidizing agent, or reducing agent; or
contacting the product of step c) with a nucleophilic agent, an alcohol derivatizing agent or combinations thereof in a solvent at between −20 and +150° C. for between 0.1 and 72 hours and then with an acid, base, oxidizing agent, or reducing agent; or
contacting the product of step c) with an acid, a base, an oxidizing agent, or a reducing agent and then with a nucleophilic agent, an alcohol derivatizing agent or combinations thereof in a solvent at between −20 and +150° C. for between 0.1 and 72 hours.

In another aspect of this embodiment, the process further comprises:
contacting the product of step d) with a nucleophilic agent, an alcohol derivatizing agent or combinations thereof in a solvent at between −20 and +150° C. for between 0.1 and 72 hours or with an acid, a base, an oxidizing agent, or a reducing agent; or
contacting the product of step d) with a nucleophilic agent, an alcohol derivatizing agent or combinations thereof in a solvent at between −20 and +150° C. for between 0.1 and 72 hours and then with an acid, a base, an oxidizing agent, or reducing agent; or
contacting the product of step d) with an acid, preferably perchloric acid, a base, an oxidizing agent, or a reducing agent and then with a nucleophilic agent, an alcohol derivatizing agent or combinations thereof in a solvent at between −20 and +150° C. for between 0.1 and 72 hours.
Preferably, the above acid is perchloric acid.

In a further aspect of this embodiment, the process further comprises:
obtaining a compound that possesses partial or total structural features of C- and D-rings of a tigliane;
contacting the obtained compound with a derivatizing agent, an acid agent or a base agent at approximately −20 to 150° C. for between about 1 to 72 hr to produce an enol derivative or ketone at the position corresponding to C13 of a tigliane; and, preferably,
contacting the enol derivative or ketone with an oxidizing agent, a nucleophilic agent, or a reducing agent at approximately +10 to +100° C. for approximately 0.1 to 72 hours.

The derivatizing agent, acid agent, or base agent, is preferably methanesulfonyl chloride in pyridine, or hydrazine hydrate. The obtained compound is preferably phorbol, a phorbol analog, or a precursor thereof. The obtained compound may be protected at positions corresponding to C-13 and/or C-20 of a tigliane or combinations thereof. The protecting groups may be removed by an acid agent or a base agent.

In another embodiment, the present invention covers a process to produce a 12-deoxy tigliane structure or a compound having a partial structure that includes the C- and D-rings of a 12-deoxytigliane of the structure:

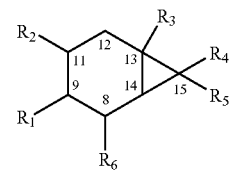

wherein $R_1$, $R_2$, $R_3$, $R_4$, $R_5$, and $R_6$ are the same or different and each are independently selected from hydrogen, methyl, alkyl (C1 to C20), cyclic alkyl (C3 to C15), aromatic ring (C4 to C6), hydroxyl, alkyl carbonate, carbamate, ester, ether, thiol, amine, and amide. $R_1$ may be alkanoyl as in —C(O)Ak wherein Ak is an alkyl chain (C1 to C20). $R_{1-6}$ groups may comprise one or more heteroatoms including, but not limited to boron, nitrogen, oxygen, phosphorous, sulfur, silicon or selenium. $R_1$ and $R_6$ may be connected as in the case of tiglianes, or may be disconnected as in the case of structural or functional analogs.

The process comprises:
a) obtaining an α, β or γ, β unsaturated ketone or enol derivative optionally protected at various positions of a compound that possesses partial or total structural derivatives of C- and D-rings of a tigliane;
b) contacting the product of step a with hydrazine or an agent equivalent to hydrazine, optionally in the presence of base or acid, between −90 and +150° C. for about 0.1 and 72 hours, followed by optional treatment with a base or hydrazine scavenger;
c) optionally contacting the product of step b with a solvent at between about +20 and +250° C. for between about 1 and 72 hours;
d) contacting the product of step b or step c, when performed, with an oxidizing agent in a solvent, optionally in the presence of other additives such as but not limited to: carboxylic acids, alcohols, thiols, amines, or halides, at between about −10 to +120° C. for between about 0.1 and 72 hours;
e) 1) contacting the product of step d with light of a wavelength that is absorbed by the product in a solvent at between about −20 and +100° C. for between about 1 to 240 min, or;

2) contacting the product of step d with a solvent and heating between about +50 and +300° C. for between about 1 and 72 hours, or;
3) contacting the product of step d with an excited state of a sensitizer formed by absorption of light by the sensitizer, or;
4) contacting the product of step d with a metal or metal salt in a solvent at between about −80 and +110° C. for between about 1 and 48 hours; and
e) isolating the cyclopropane containing functional or structural analog.

The present invention also provides products made by the above processes.

$R_1$, $R_2$=H, $R_3$=OAc (Prostratin); $R_1$, $R_2$=H, $R_3$=OCOCH$_2$PH (DPP); $R_2$ and/or $R_3$=H (di-deoxy tiglianes); OCOR (esters); OR (ethers); Cl, Br, I, F (halogens); SeR (selenium ethers); SAk, SOAk, SO$_2$Ak (thiol ethers, sulfones, sulfonates); Ak, Ar, CN (Carbon substituents); and NHR, NR$_2$, NHCOR (Amines, amides) Allows rapid diversification of C13 and cyclopropane substituents.

Figure 7:
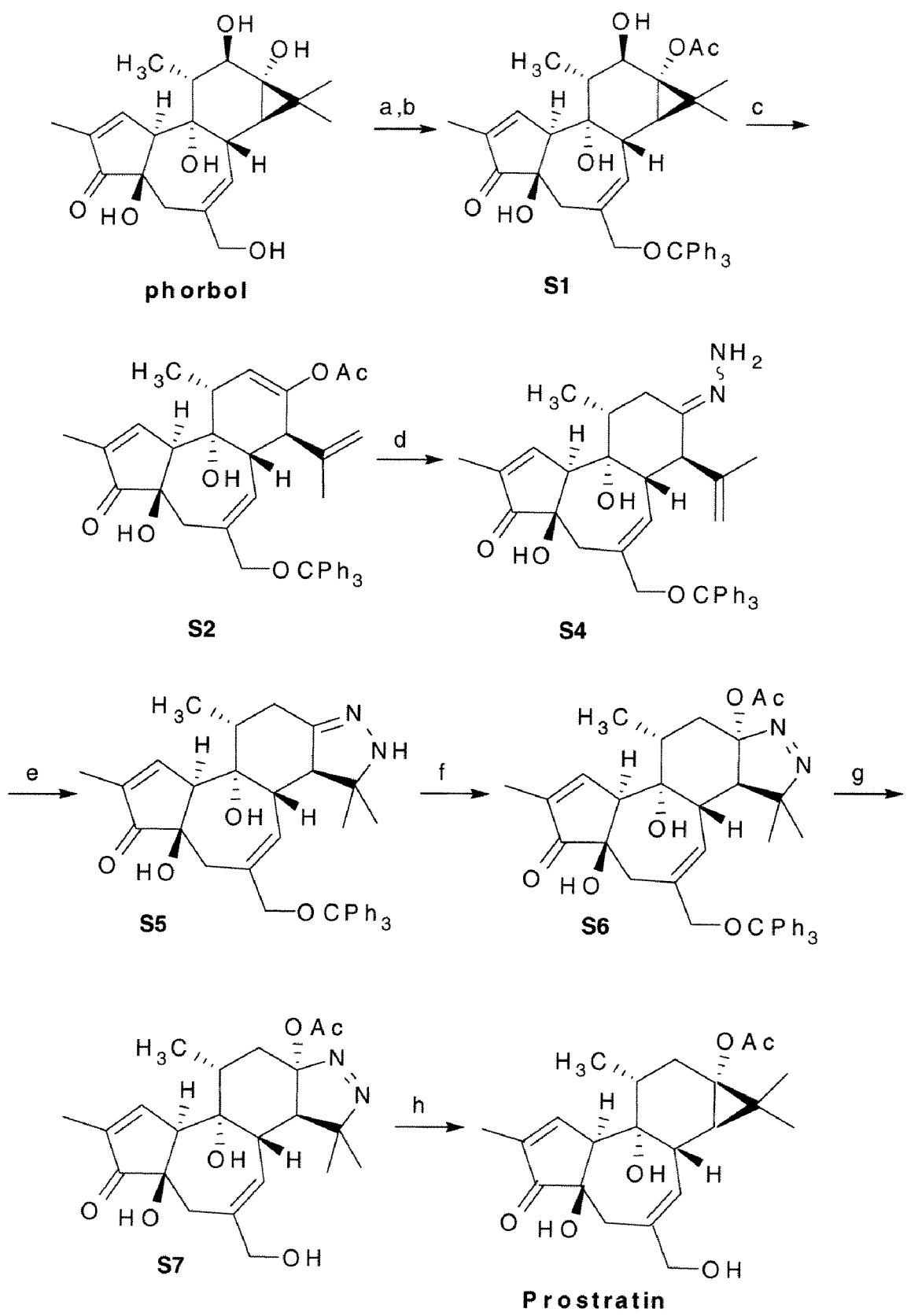

FIG. 7 is a schematic representation of one embodiment of the semi-synthesis of prostratin.
 a) TrCl (4 eq.), Pyr., RT, 72 hr (77%)
 b) Ac$_2$O (3 eq.) CH$_2$Cl$_2$/THF (1:1), RT, 24 hr (88%)
 c) MsCl (1.3 eq.), Pyridine, 60° C., (78%) 1 hr
 d) K$_2$CO$_3$ (1.5 eq.), then AcOH (4 eq.) H$_4$N$_2$H$_2$O (1.5 eq.), RT, 1 hr
 e) Tol./(iPr)$_2$NEt (9:1), 130° C., 12 hr
 f) Pb(OAc)$_4$ (1.2 eq.) DCM, 0° C. 10 min. (40%-50%, 4 steps)
 e) Tol./(iPr)$_2$NEt (9:1), 130° C., 12 hr
 f) Pb(OAc)$_4$ (1.2 eq.) DCM, 0° C., 10 min. (40%-50%, 4 steps)
 g) HClO$_4$ in MeOH (0.01M), RT, 15 min (90%)
 h) 300 nm light, PhH, RT, 45 min (92%)

Figure 8:
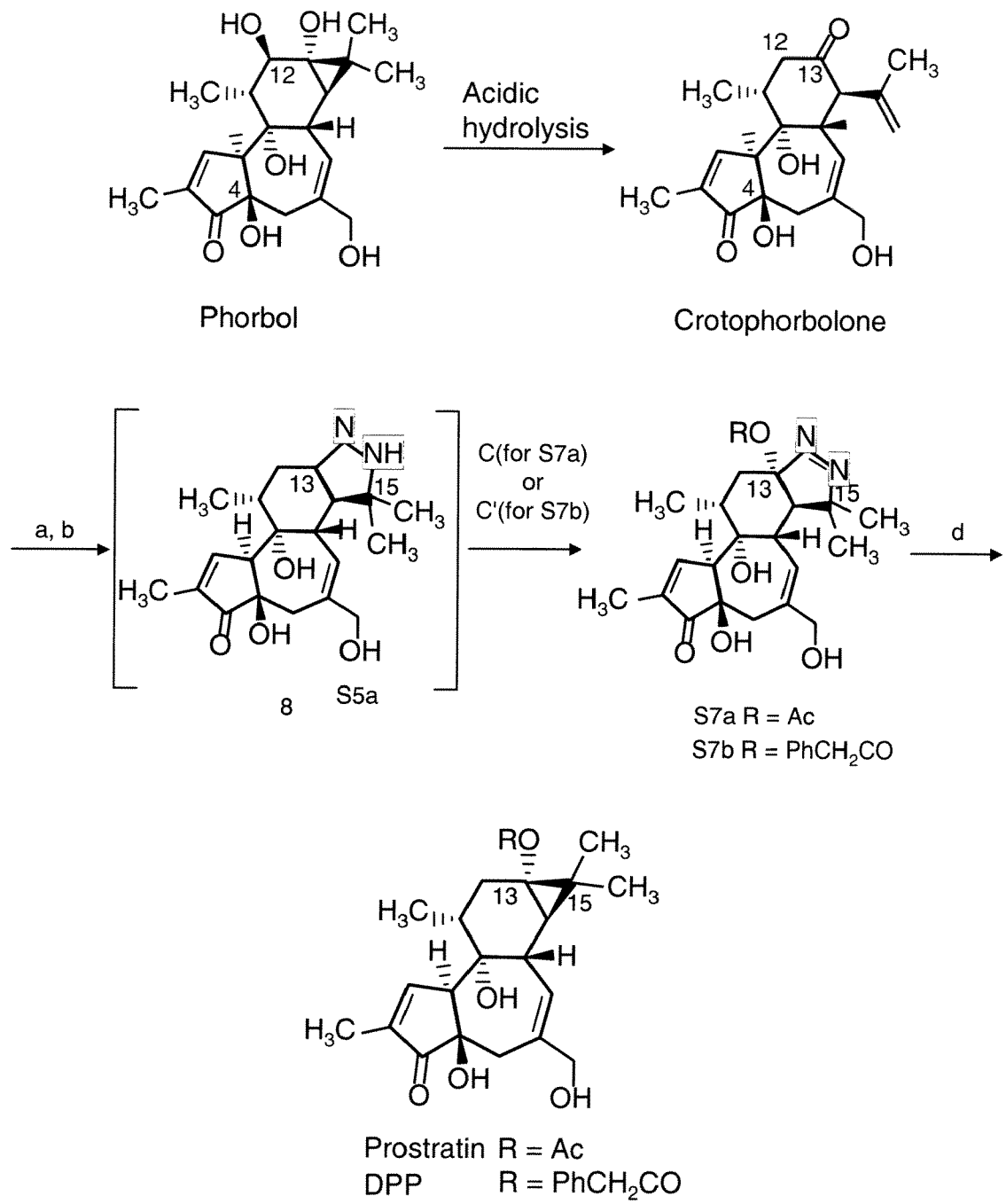

FIG. 8 is a schematic representation of another embodiment of the semi-synthesis of prostratin.
 (a) H$_4$N$_2$H$_2$O (2 equiv.), AcOH (5 equiv.), MeOH, 25° C., 45 min;
 (b) pyridine/DIPEA (9:1), 150° C., 48 h;
 (c) Pb(OAC)$_4$ (1.1 equiv.), CH$_2$Cl$_2$, 0° C., 30 min (43% of S7a from Crotophorbolone);
 (c') Pb(OaC)$_4$ (1.2 equiv.), PhCH$_2$COOH (50 equiv.) (premixed), CH$_2$Cl$_2$, 0° C., 30 min. (36% of S7b from Crotophorbolone;
 (d) hv (300 nm), EtOAc/benzene (1:1) or MeOH, 25° C. (67-92% for Prostratin, 90% for DPP)

Figure 9:
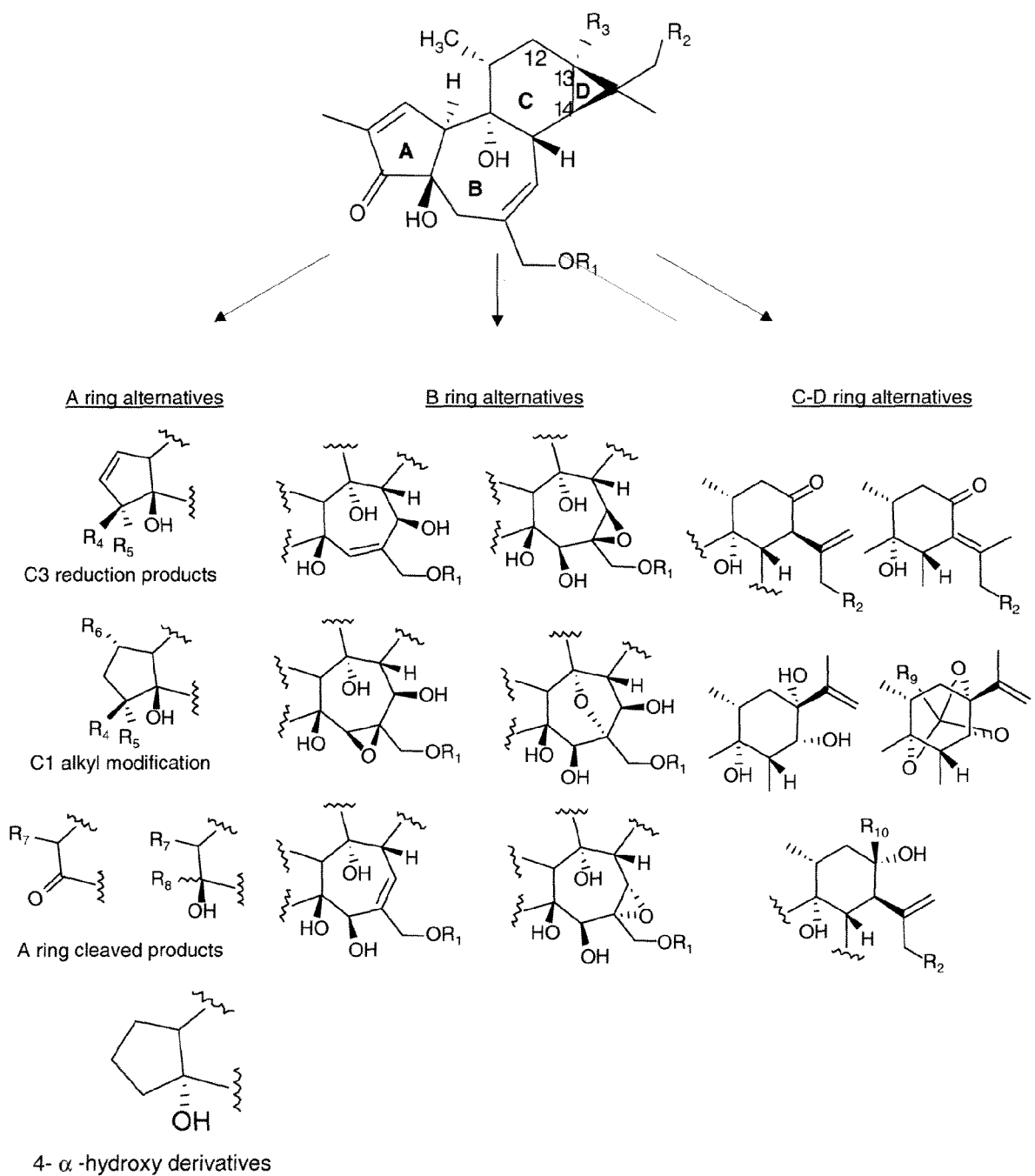

FIG. 9 is a schematic representation of representative analogs available through modification of a, b, c, and/or d rings.

Figure 10:
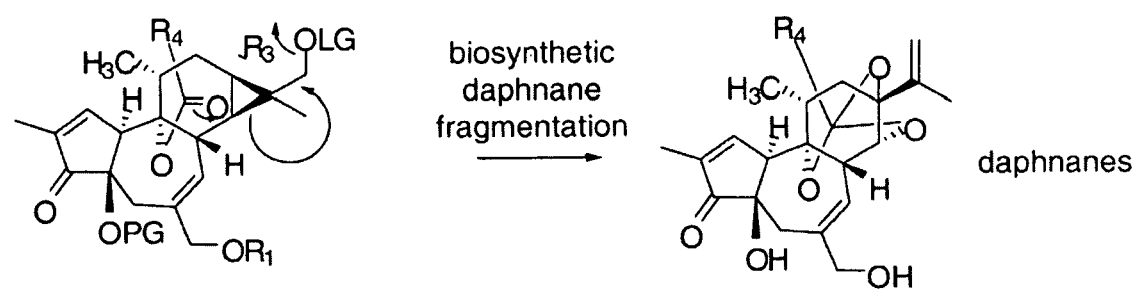

FIG. 10 is a schematic representation demonstrating ways to access biologically active daphnanes.

Figure 11:
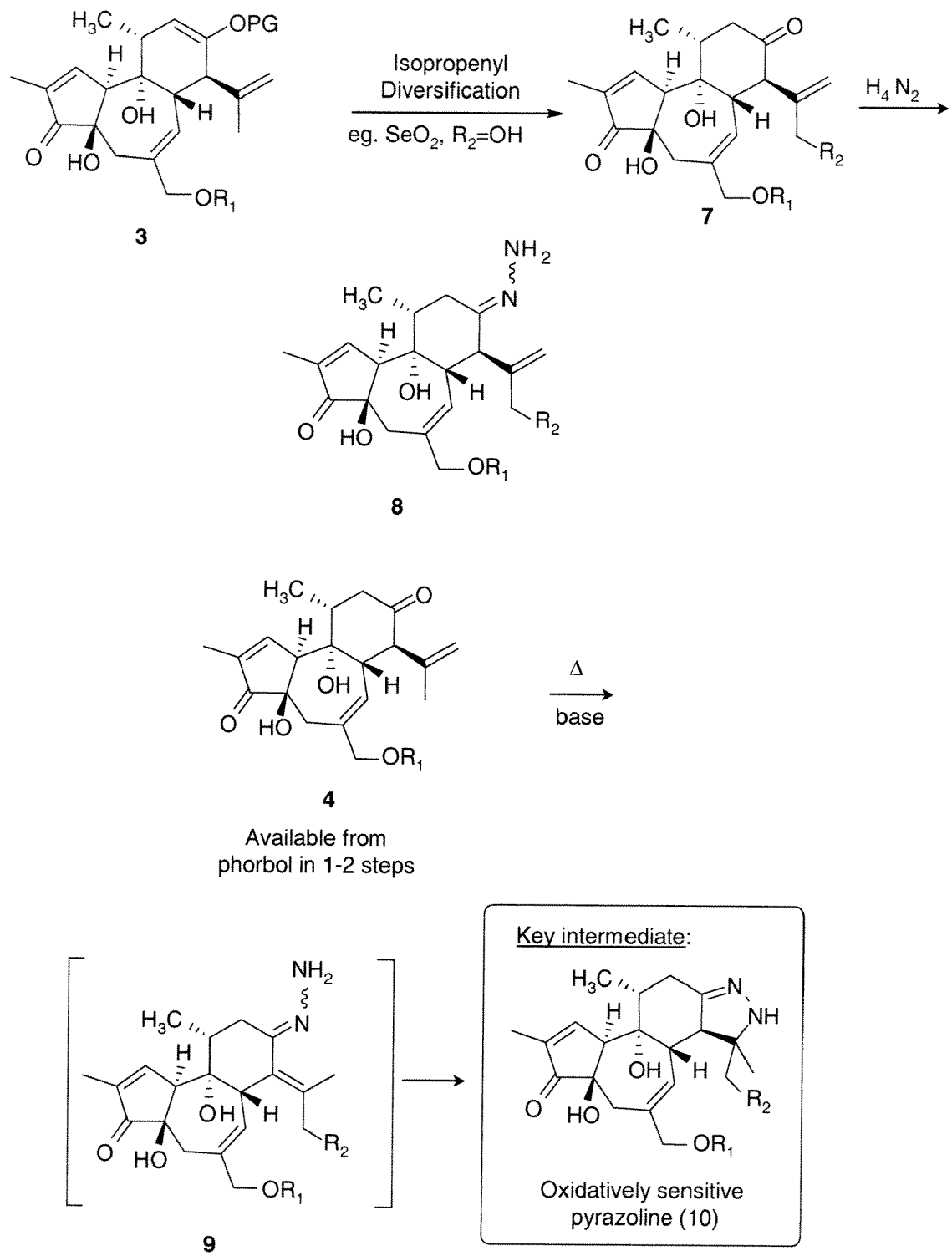

FIG. 11 is a schematic representation showing concise synthesis of a key intermediate.

Figure 12:
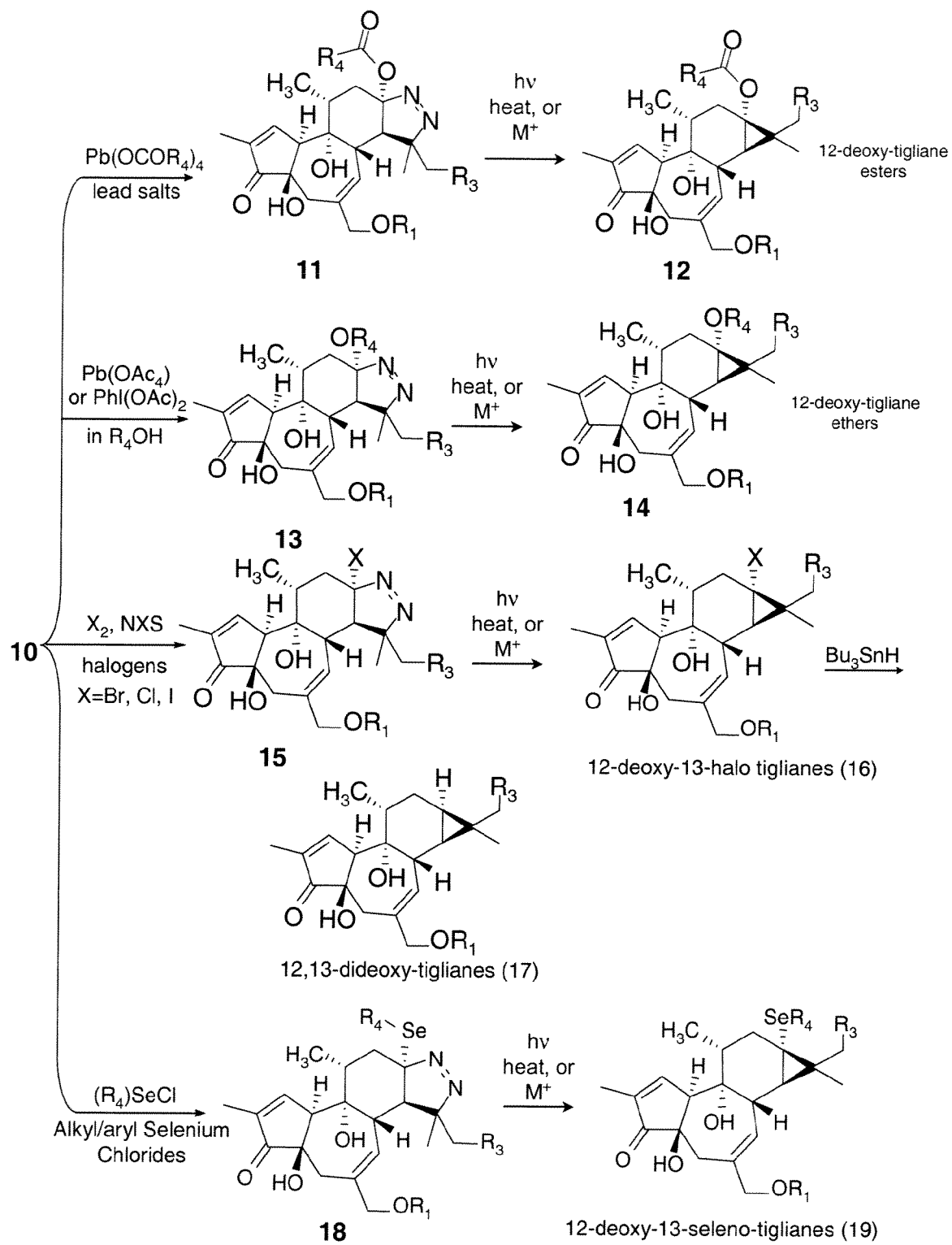

FIG. 12 is a schematic representation of the pyrazoline functionalizations, and conversion to cyclopropane derivatives, Part I.

Figure 13:
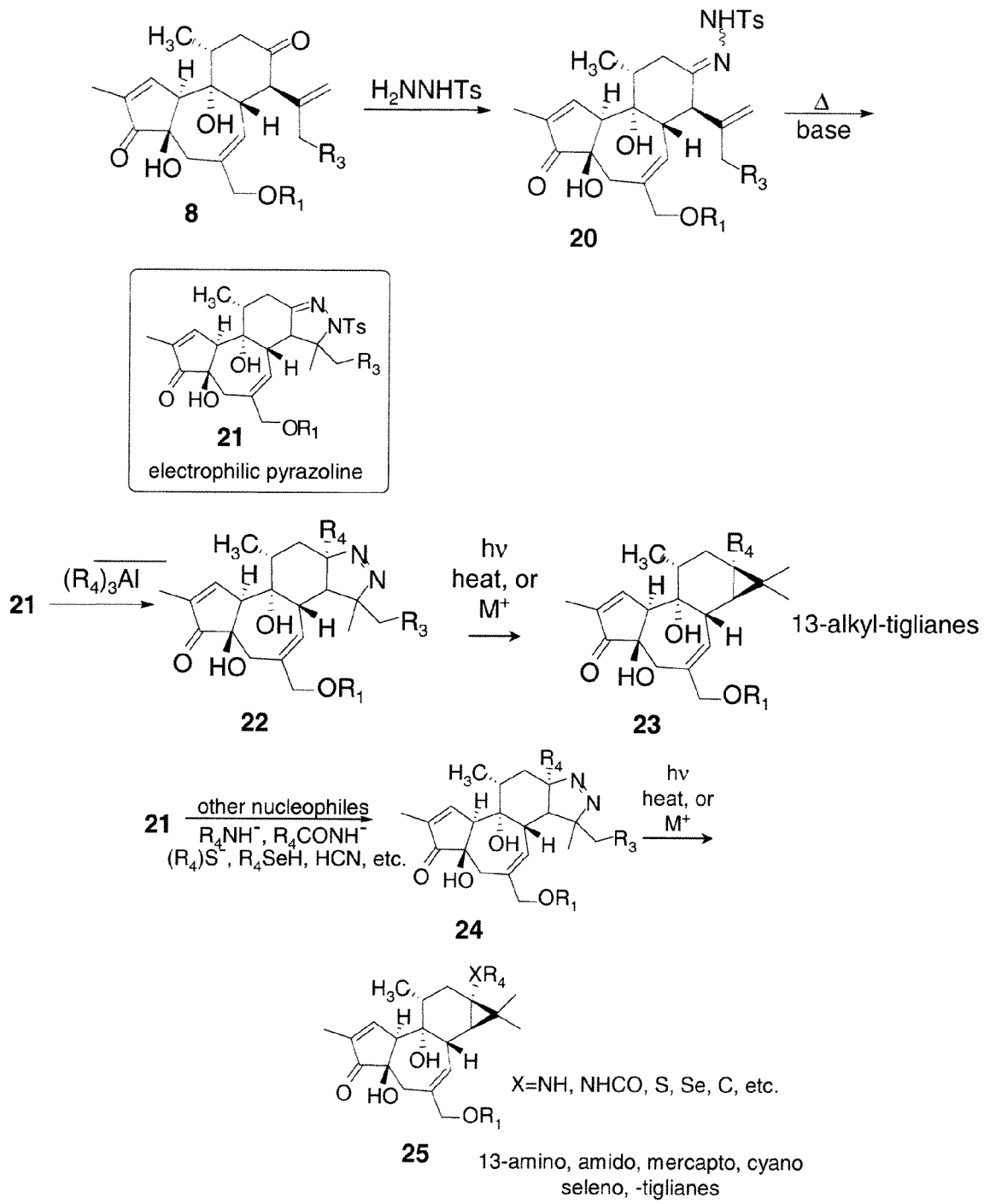

FIG. 13 is a schematic representation of the pyrazoline functionalizations, and conversion to cyclopropane derivatives, Part II.

Figure 14:
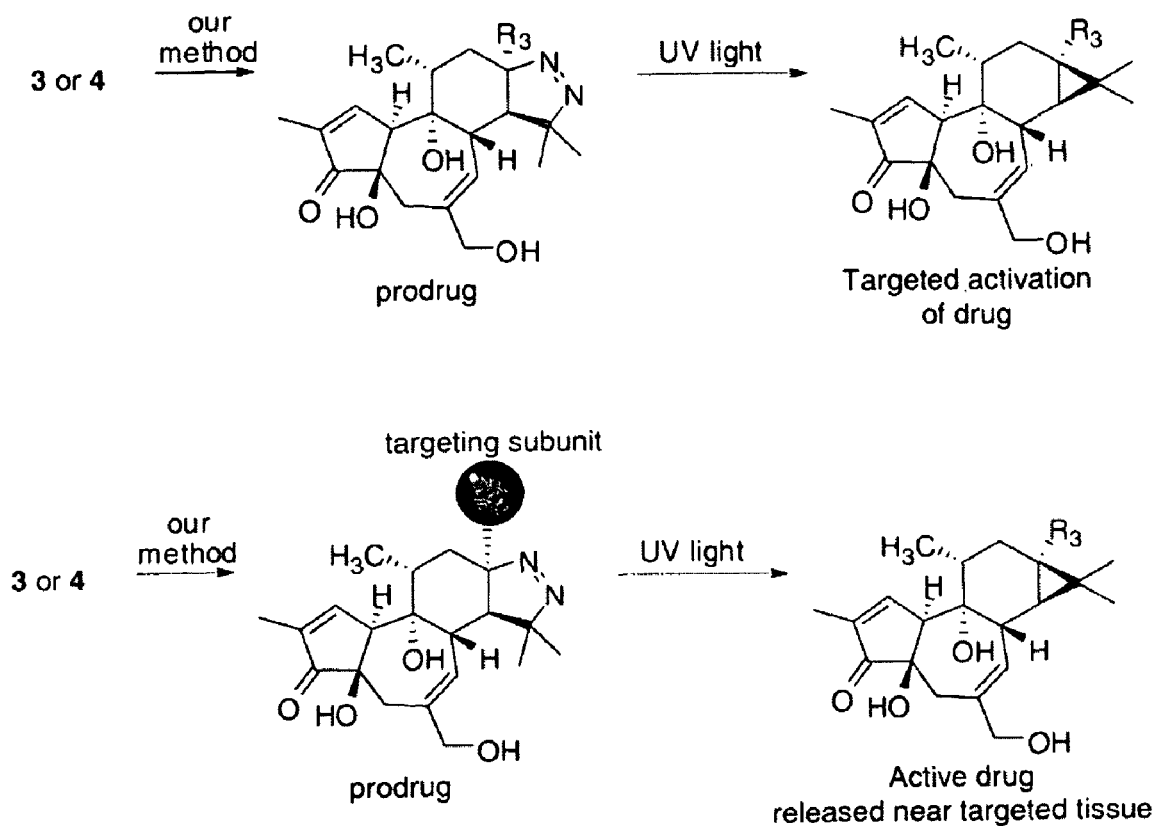

FIG. 14 is a schematic showing photo-activatable drugs.

DETAILED DESCRIPTION OF THE INVENTION AND PREFERRED EMBODIMENTS

Definitions

As used herein, the definition of the terms used herein are usually found in the art encyclopedias and dictionaries, see for example, Encyclopedia of Chemical Technology (all volumes), Hawley's Condensed Chemical Dictionary, etc.

"Alkyl (C1-C15)" refers to an alkyl group having from 1 (methyl) to 15 carbons in linear or branched chain. "Cyclic alkyl (C3 to C15)" refers to a cyclic group of from 3 to 15 carbon atoms. "Aromatic ring" refers to a carbocyclic or heterocyclic ring possessing resonance, namely it pertains to a closed ring of from 3 to 10 covalently linked atoms, more preferably from 5 to 8 covalently linked atoms, which ring is aromatic.

"Daphnane" refers to a compound having a partial structure, which includes a tricyclic carbon skeleton shown below (with numbering).

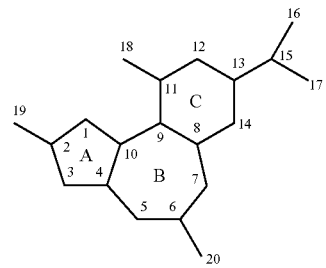

"Derivative" refers to a compound derived from another compound through one or more chemical transformations.

"Tigliane" refers to a compound having a partial structure, which includes a tetracyclic carbon skeleton shown below (with numbering).

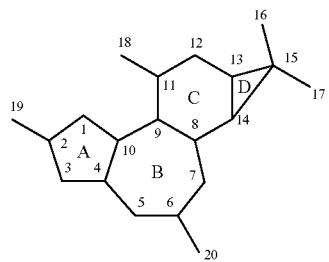

"Ingenane" refers to a compound having a partial structure which includes a tetracyclic carbon skeleton shown below (with numbering)

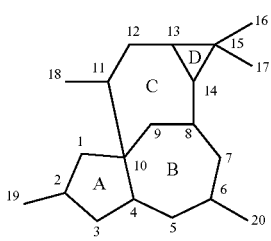

"Functional analog" refers to a compound that exhibits the same or similar activity (biological function) as another compound whether or not the compounds are structurally similar. For example, all protein kinase C (PKC) activators are functional analogs; even though they possess different structures they all activate PKC.

"Structural analog" refers to a compound that is structurally similar to another compound whether or not the compounds are functionally similar. For example, all tiglianes are structural analogs; even though they possess the same tigliane core they often exhibit widely different activities (functions).

"Tigliane-type compound" refers to a compound having at least a partial structure that includes the C- and D-rings of a tigliane, where $R_1$-$R_{14}$ can be varied. For example, Ingenanes are "Tigliane-type" compounds:

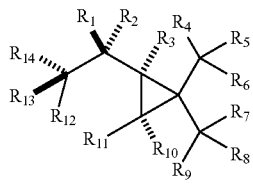

wherein $R_1$ to $R_{14}$ are the same or different and each independently selected from hydrogen, methyl, alkyl (C1 to C20), cyclic alkyl (C3 to C15) aromatic ring, hydroxyl, alkyl carbonate, carbamate, ester, ether, thiol, amine, or amide. $R_1$ may be alkanoyl as in —C(O)Ak wherein Ak is an alkyl chain (C1 to C20). $R_{1-14}$ groups may contain one or more heteroatoms including, but not limited to boron, nitrogen, oxygen, phosphorous, sulfur, silicon or selenium. $R_{11}$ and $R_{12}$ may be connected as in the case of tiglianes, or may be disconnected as in the case of 12-deoxy tigliane compounds which are structural or functional analogs of the illustrated embodiments. Further exemplification of the present analogs is given in the Figures.

"Acid agent" refers to the usual definitions found in this art. Examples include but are not limited to Brønsted acids including perchloric acid, hydrochloric acid, hydrofluoric acid, hydrobromic acid, and toluenesulfonic acid; and Lewis acids including boron trifluoride.

"Base agent" refers to the usual definitions found in this art. Examples include but are not limited to lone pair donors and proton acceptors, including N,N-diisopropyl ethylamine (Hunig's base), and other amine bases, metal alkoxides, and alkyllithiums.

"Derivatizing agent" refers to the usual definitions found in this art for altering hydroxyl groups, ketones, and/or enol ethers. These typically consist of electrophilic species. Examples include, but are not limited to mesyl chloride, thiocarbonyl diimidazole, toluenesulfonyl chloride, etc.

"Hydrazine equivalent" refers to the usual definitions found in this art. Examples include but are not limited to hydrazine hydrate, tosyl hydrazide, silyl hydrazides, carbomethoxy hydrazide, tert-butyl carbazate, etc.

"Metal or metal salt" refers to the usual definitions found in this art. Examples include but are not limited to Ytterbium (III) triflate, Wilkinson's catalyst, Ruthenium (IV) chloride, etc.

"Nucleophilic agent" refers to the usual definitions found in this art. Examples include, but are not limited to alkyl alcohols such as methanol or ethanol, methoxide, carboxylic acids such as phenylacetic acid, carboxylates, thiols, selenols, etc.

"Oxidizing agent" refers to the usual definitions found in this art. Typically refers to agents that can take electrons from other molecules. Examples include but are not limited to, metal oxides such as $Ag_2O$, metal salts such as $Pb(OAc)_4$, hypervalent halogen reagents such as $PhI(OAc)_2$, an electrochemical anode, molecular oxygen or ozone, peroxides such as benzoyl peroxide, molecular halogen, molecular halogen equivalents such as N-bromosuccinimide.

"Protecting agent" refers to the usual definitions found in this art for modifying a functional group to prevent an undesired transformation. The modification can then later be removed to restore the original functionality.

"Sensitizer" refers to the usual definitions found in this art. Examples include but are not limited to chemical compounds, which can absorb light and transfer the resultant excitation to the ground state of another molecule. Examples include, but are not limited to benzophenone, acetophenones, DMAB, and polyarenes.

"Wavelength of light" refers to the light used for the reaction of step h) in Claim 1. Examples of suitable wavelength ranges include, but are not limited to: about 200 and 800 nm; preferably between about 300 and 400 nm; most preferably between about 300 and 370 nm.

Semi-Synthesis of Prostratin and Related Analogs

Figure 1:
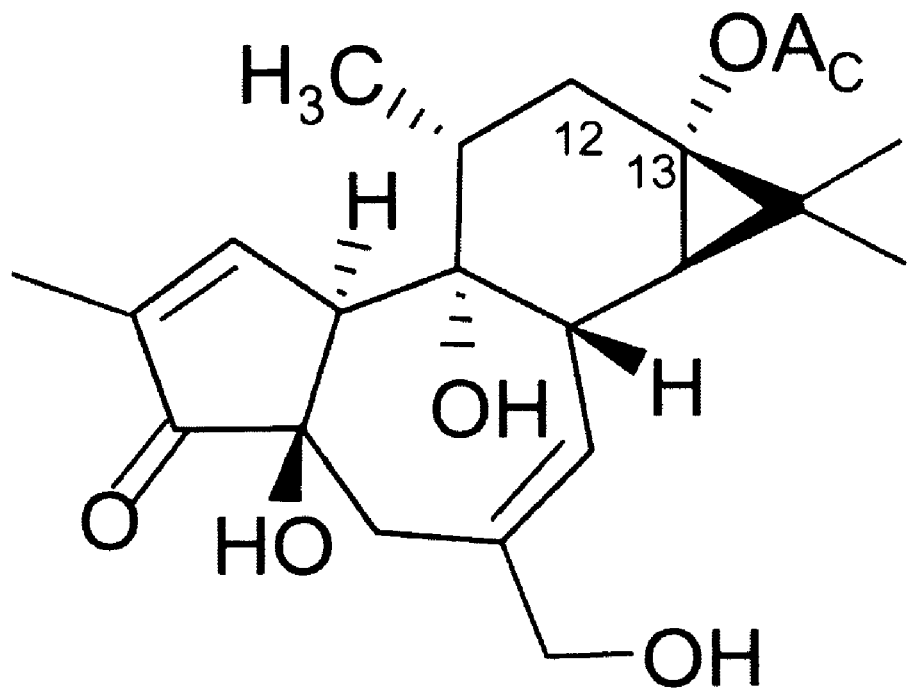
FIG. 1 is a schematic representation of prostratin.
Figure 2:
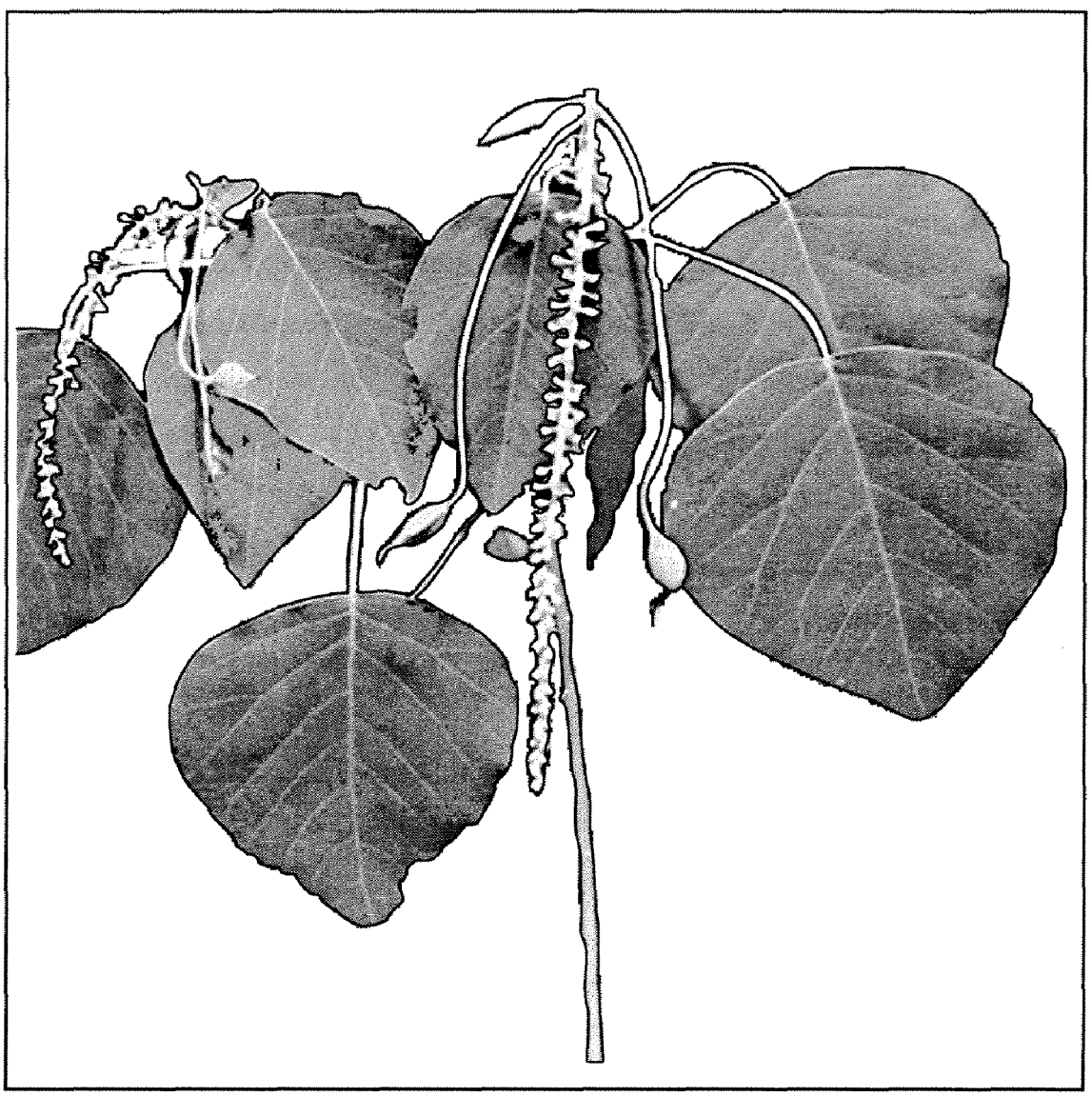
FIG. 2 is a photograph of *Homalanthus nutans*. (Source: Sanders, R., "Landmark agreement between Samoa and UC Berkeley could help search for AIDS cure."
Figure 3:
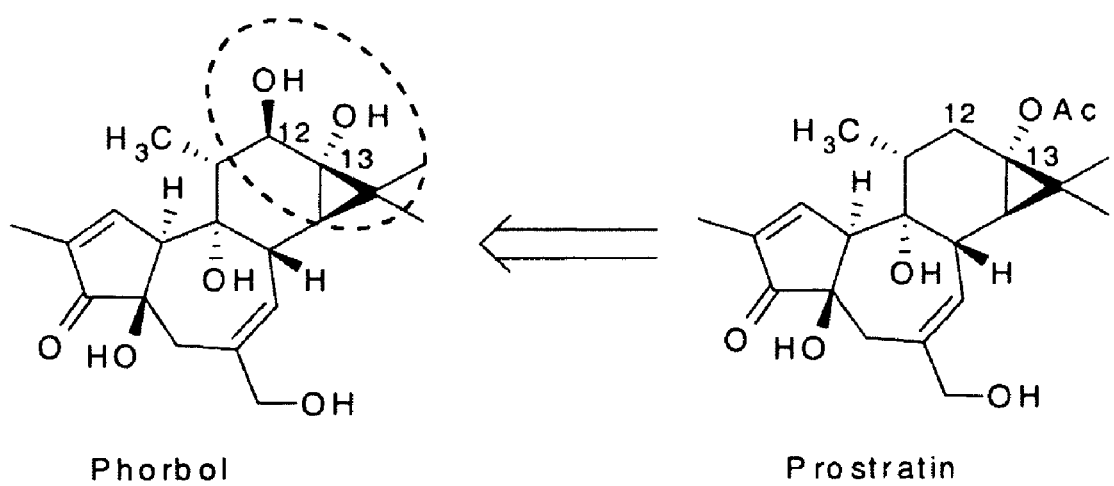
FIG. 3 is a schematic representation of the theoretical deoxygenation of tigliane scaffold. This outlines the overall process to produce prostratin from phorbol, and representation of intermediates that complicate direct interconversion.
Figure 3:
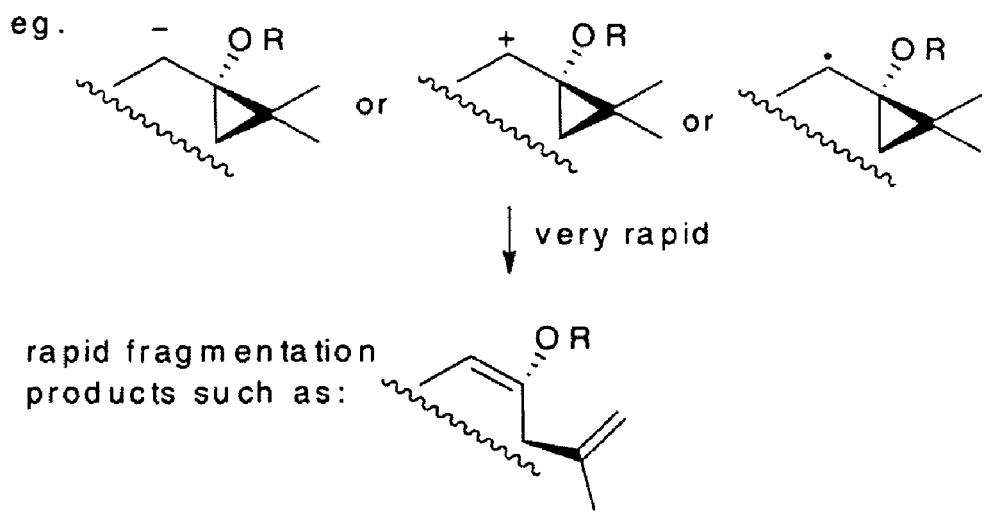

On paper, the desired transformation of the phorbol skeleton to 12-deoxyphorbols involves only the removal of an oxygen at C-12 (FIG. 3). However, selective transformation adjacent to reactive functionalities including strained rings like that in phorbol is a major synthetic challenge. With the specific example of phorbol esters, de-oxygenation of phorbol at the C-12 position is complicated by the adjacent cyclopropyl group. The inherent ring strain of the cyclopropane ring adjacent to C-12 makes a selective de-oxygenation of C-12 exceedingly difficult, as any reactive intermediate formed in this position (cationic, radical, anionic, radical anion, radical cation, carbene, metal carbenoid) could result in opening of the ring (FIG. 3). For example, cyclopropyl methylradicals open at near diffusion control rates with rate constants on the order of 108 s-1.25 Alternatively, the C-12 hydroxyl group of phorbol could be converted to a carbonyl group and the latter reduced to a methylene group. However, such oxidation and reduction processes are incompatible with other functionality in the molecule. Protecting these other functionalities and subsequent deprotection after C-12 reduction would require additional synthetic operations. It is then non-obvious how one can convert phorbol into tiglianes lacking C-12 oxygenation in a practical fashion and more specifically how this would be done to make prostratin and structural analogs thereof. We have been able to accomplish this feat in our laboratory.

Our short synthetic route has advantages and improvements over the current supply (natural extraction) in that not only are we able to convert a cheap and renewable starting material (phorbol) into prostratin, related 12-deoxyphorbol-phenylacetate, and analogs thereof, we are also able to access non-oxygenated derivatives, possessing different functionalities at C-13. These analogs are both present in nature, but only from rare isolates; and in materials that have not been isolated from nature but may possess important medicinal activities that are even better than any of the natural isolates. In short, our route allows for the practical synthesis of prostratin and structural and functional analogs thereof and can be used to tune the performance of such compounds to achieve optimal therapeutic value.

The following description pertains to our synthesis of prostratin but can be applied to structural and functional analogs because of its flexibility and generality. Our synthesis of prostratin commences from either phorbol, phorbol-20-trityl ether, or crotophorbolone. Phorbol is a tigliane diterpene isolated from croton oil (~1% yield).21 Croton oil is obtained from the seed of *Croton tiglium*, a renewable source, and it is readily available in kilogram quantities ($460/kg from LC labs). Croton oil is sufficiently abundant (45% of seed kernel in *croton tiglium*) to be considered along with palm, coconut, jatropha, rapeseed, and neem oils to be a source of biodiesel fuel 22. Phorbol and phorbol-20-trityl ether are also commercially available ($750/g from LC Labs, Woburn, Mass.). Crotophorbolone may be produced from acid hydrolysis of phorbol. Alternatively, crotophorbolone may be obtained by the hydrolysis of 12-deoxy-16-hydroxyphorbol esters, which are available from Jatropha curcas seed oil, an abundant renewable feedstock being developed as biodiesel.

Figure 4:
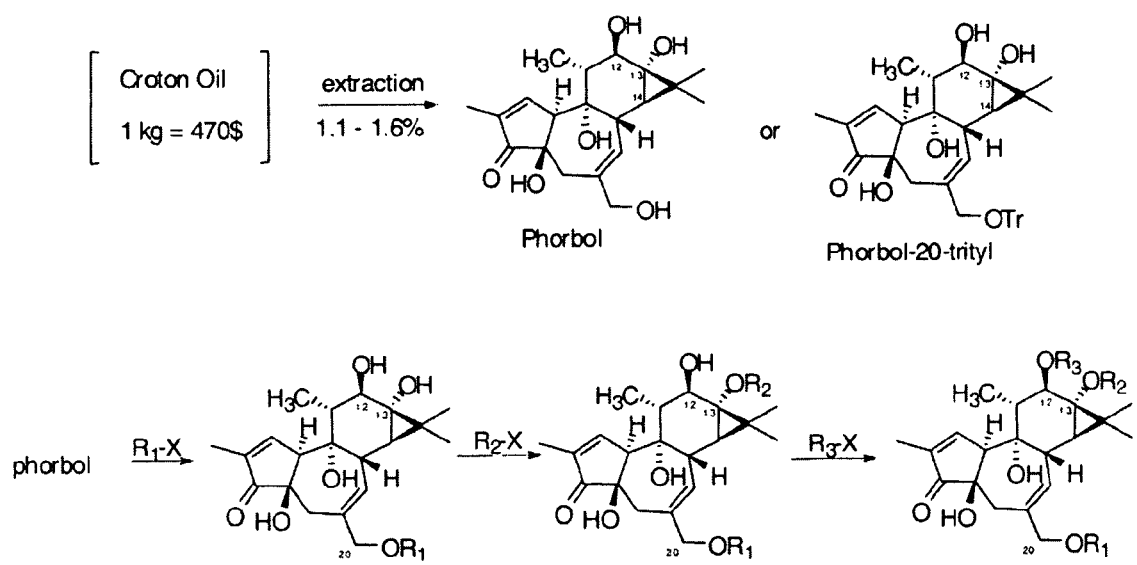
FIG. 4 is a schematic representation of the isolation of phorbol and an alcohol derivation order.

While formally a penta-ol, the phorbol alcohols can be differentiated readily by their different reactivities (FIG. 4). The alcohols are derivatized in the order: C-20, C-13, C-12, followed by typically difficult derivatization at C-4 and C-9 (not depicted).

Figure 5:
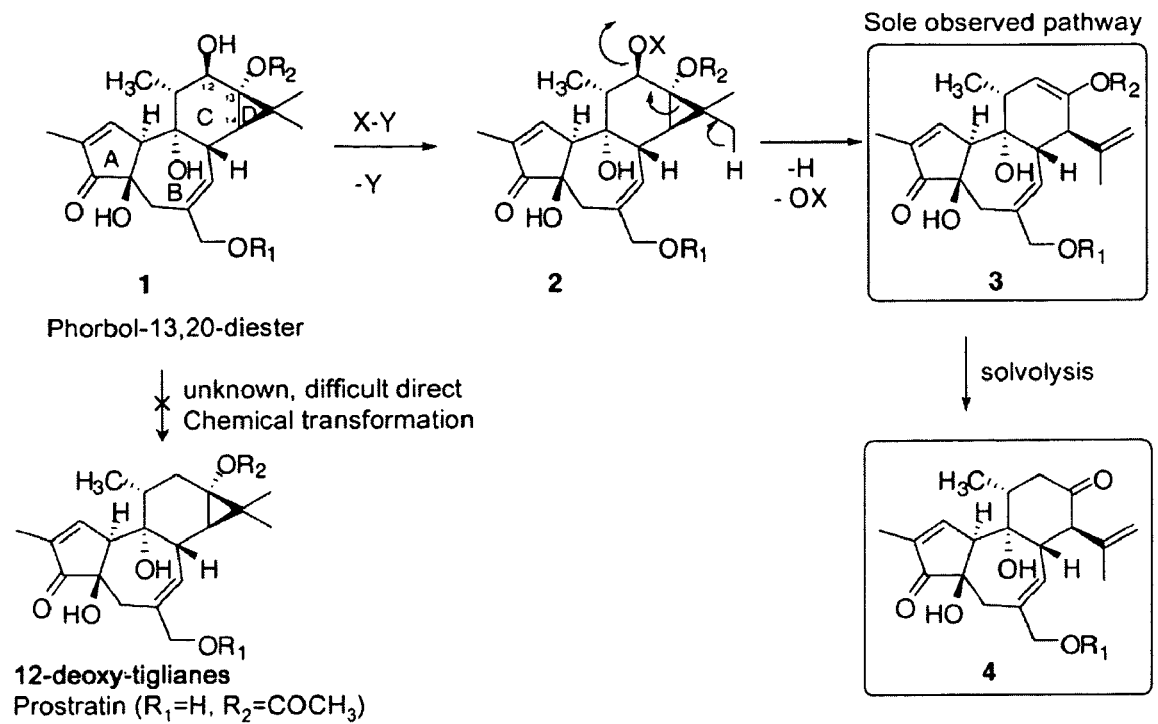
FIG. 5 is a schematic representation of the ring-opening elimination to yield isopropenyl enol esters and ketones.

The derivitization of phorbol-13, 20-diesters (1) at the C-12 position is frequently attended by fragmentation to yield enol 3 (FIG. 5), as originally noted by Bartsch26 and more recently reported by others using carbonyl diimidazole28. Hydrolysis of the initial enol derivative gives the C13 ketone 4. The strain-induced cleavage of the cyclopropane bond in this reaction giving 3 illustrates the problem associated with direct deoxygenation of C12.

Figure 6:
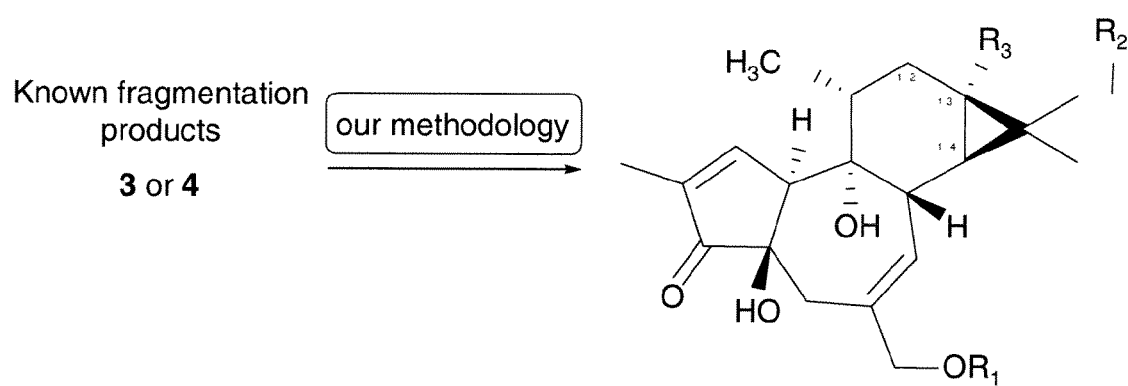
FIG. 6 is a schematic representation of other analogs that can be accessed with this invention.

Given that the C12 oxygen in the starting phorbol has been removed in the above process leading to 3 or 4, the challenge now lies in reestablishment of the cyclopropane "D" ring. The following pages provide a discussion of a technology that not only enables re-establishment of the D ring and thereby enables the conversion of phorbol into prostratin and 12-deoxyphorbol-13-phenylacetate (DPP), but also allows for rapid structural diversification of the C-13 and cyclopropane substituents (R2, R4 respectively). (FIG. 6)

Phorbol can be converted to prostratin in a variety of ways. In one embodiment, the synthesis occurs as shown in FIG. 7. First, phorbol is converted to a phorbol-13, 20-diester. In particular, the alcohol at C13 is converted to an acetate and the alcohol group at C20 is protected by a trityl protecting group, thus producing phorbol-12-acetate-C-20 trityl ether S1. Next, phorbol-12-acetate-C-20 trityl ether is converted to an enol acetate S2. This product is then used to generate a hydrazone intermediate S4, followed by conversion to a pyrazoline S5. The pyrazoline S5 is then converted to an acetoxypyrazoline S6. The trityl protecting group is then removed, forming cyclic diazene S7, followed by formation of the cyclopropane 12-deoxyphorbol-13-acetate (prostratin). Details of this embodiment are described below in EXAMPLES 1-4. A similar process may be used to produce DPP, as described below in EXAMPLES 8-10.

In an alternative embodiment, the acetoxypyrazoline S6 is first converted into cyclopropane S8, followed by removal of the trityl-protecting group, thus generating prostratin. Details of this embodiment are described below in EXAMPLES 5 and 6.

Another embodiment is shown in FIG. 8. In this embodiment, the acidic hydrolysis of phorbol produces crotophorbolone, which is then used as the starting material. First, treatment of crotophorbolone with hydrazine in the presence of acetic acid selectively affords the C13 hydrazone (not shown), which without isolation is cyclized to pyrazoline S5a. Oxidation of pyrazalone S5a with lead (IV) tetraacetate gives cyclic diazene S7a, allowing for concomitant direct introduction of a C13 acetate group and a diazene bridge between C13 and C15. Other C13 esters can also be directly introduced with this procedure by using the corresponding lead (IV) carboxylate or related oxidants. Photolysis of cyclic diazene S7a results in the extrusion of nitrogen and reestablishment of the C13-15 cyclopropane bond, providing prostratin in high yield and in a remarkably concise four-step sequence from crotophorbolone, or five steps from phorbol with a 12-16% overall yield, producing over 100 mg of prostratin from a single run. DPP can be made in a similar manner. In this case, the acetate ligands of lead tetraacetate are exchanged by premixing with an excess of phenylacetic acid. The resulting salt induces the oxidative conversion of pyrazoline S5a to diazene S7b. (in 36% yield for three steps from crotophorbolone). Subsequent photolysis affords the natural product and therapeutic lead DPP in 90% yield, or 13% overall yield from phorbol. Details of this embodiment are described below in EXAMPLES 7 and 11.

In addition to allowing for introduction of various groups at the C13 position, the enabling methodology can also be used to access a wide range of varied structures of the tigliane, daphnane and ingenanes families and structural and functional analogs thereof. There are a myriad of A- B- and C/D ring modifications that one could access, that are either known, or would represent new entities (FIG. 9). The combination of our 12-deoxy tigliane strategy with one or more of these suggested modifications gives an enormous array of structural possibilities, with the ability to generate a large library of bioactive molecules. This could also potentially lead to substrates, which would enable the testing of the biosynthetic daphnane formation (FIG. 10).

The conversion of phorbol to 12-deoxy-tiglianes thus proceeds from D-ring fragmented products 3 or 4 (FIG. 11). The opening of the D-ring also provides the opportunity to derivatize the isopropenyl unit in 7, prior to mono-hydrazone formation with 8 while leaving the unsaturated A-ring ketone intact. Then, upon modest heating (130° C.) in the presence of base, hydrazone 8 can be isomerized to 9 and converted to pyrazoline 10.30

Pyrazoline 10 provides a key intermediate for the introduction of many different groups at C13. (FIG. 12)

For example, pyrazoline 10 reacts very rapidly upon exposure to lead (IV) carboxylate salts, and rapidly (generally <30 sec. at 0° C.) forms carboalkoxypyrazolines (11). These compounds (11) readily lose nitrogen upon exposure to 300 nm light in regular Pyrex glassware to form high yields of 12-deoxy tigliane esters (12).31 An intra- or inter-molecular sensitizer could also be employed to achieve the desired excitation and extrusion of nitrogen.

Alternatively, this transformation could also be done thermally at temperatures of about 220° C., or exposure to metal salts such as Yb(Otf)3.32

A similar technique can be employed in the formation of ethers (13, 14) by dissolution of lead tetraacetate or iodobenzene diacetate in the desired alcohol prior to reaction.33 Pyrazolines can also be oxidized by mild treatment with N-halo-succinimides or halogens34 to yield the halo pyrazolines (15), which can be fragmented to produce the halo-tiglianes (16). The halogen functionality is then reduced by exposure to reducing agents such as tin hydrides27 to produce novel 12,13-dideoxytiglianes (17)—which like the analogous ingenanes lacking oxygen at C12 and C13 are of interest for their anticancer activity. The pyrazolines have also been known to undergo reaction with selenyl chlorides, to produce selenyl pyrazoles 19, and ultimately lead to 13-selenyl tiglianes 19. Pyrazoline oxidation can also be effected with alkyl peroxides, or peroxy acids.

The same methodology could be applied to the formation of tosyl pyrazolines 21 (FIG. 13), which upon reaction with trialkylaluminum reagents, 27 would lead to alkyl pyrazolines35 and subsequently to 13-alkyl tiglianes. The methodology could be expanded to include other heteroatom nucleophiles, including sulfur, nitrogen or selenium to give access to other 13-heteroatom-substituted tiglianes.37 Hydrocyanation can also be affected, ultimately giving rise to 13-alkyl tiglianes.

The intermediate substituted, kinetically stable pyrazolines (such as 11, in FIG. 12) upon deprotection at C-20 could be used as photo-activatable prodrugs. The pyrazoline is not biologically active but can be converted to the biologically active C13 substituted tiglianes upon exposure to UV light (FIG. 14). In addition to direct medicinal applications, attachment of fluorescent probes to these photo-activatable compounds may lead to the discovery of new tools for probing signaling pathways related to HIV and other diseases.

The above described methodology can be readily applied to the synthesis of various biologically active compounds as exemplified by the semisynthesis of prostratin from phorbol (FIG. 7) or crotophorbolone (FIG. 8). The synthetic material so obtained is identical spectroscopically to an authentic sample of the natural product obtained from natural sources. (See EXAMPLE 4 below). We have also applied this synthesis to a number of other analogs, including 12-deoxyphorbol-13-phenylacetate (DPP).

This methodology provides a new and scalable procedure to supply agents, e.g., prostratin, related 12-deoxyphorbol-13-phenylacetate, and many other structural and functional analogs, as needed for preclinical and clinical development and eventual human therapeutic use. In addition, this methodology provides access to compounds that cannot be accessed by natural product isolation, allowing for control and optimization of the factors that would provide for superior therapeutic activity.

Table 1 shows a comparison of the current isolation method of prostratin to the inventive semi-synthetic methods to obtain prostratin.

TABLE 1

Two methods to obtain prostratin and its analogs

| | Current isolation method | New semi-synthetic method |
|---|---|---|
| Natural source | Stemwood of *Homalanthus nutans* (Samoan mamala tree) | Croton oil (from the seed of *Croton tiglium*) |
| Availability of the source | Only in Samoa | *Croton tiglium* is widely available in India, China, and Sri Lanka<br>Croton oil is commercially available in multi-kilogram quantities |
| Process | 1 extraction from natural source | 5-7 steps from Croton oil |
| Yield | 3 chromatographic purifications<br>0.0013% (15 mg from 1.05 kg of stemwood, varies significantly between samples) | 3 chromatographic purifications<br>~0.1% from Croton oil (~10-20% from phorbol) |
| Sustainability | The tree is harvested and sacrificed | *Croton tiglium* seed can be harvested annually without sacrificing the organism[14] (900 kg seeds/ha) |
| Flexibility | Only prostratin is available | Amenable to many other natural and unnatural phorbol esters |

Utility and Administration

Administration of the active compounds and salts described herein can be via any of the accepted modes of administration for therapeutic agents. These methods include oral, parenteral, transdermal, subcutaneous and other systemic modes. In some instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, skin patch, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the severity of the affliction, the manner of administration and the judgment of the prescribing physician. However, an effective dosage is in the range of 0.001-100 mg/kg/day, preferably 0.005-5 mg/kg/day. For an average 70 kg human, this would amount to 0.007-7000 mg per day, or preferably 0.05-350 mg/day. Alternatively, the administration of compounds as described by L. C. Fritz et al. in U.S. Pat. No. 6,200,969 is followed. One of skill in the art with this disclosure can create an effective pharmaceutical formulation.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 17th Edition, 1985. The composition or formulation to be administered will, in any event, contain a quantity of the active compound(s), a therapeutically effective amount, i.e., in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 1-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation or skin patch for a slow-release or sustained-release system, such that a constant level of dosage is maintained. See. e.g., U.S. Pat. No. 3,710,795, which is incorporated herein by reference.

The following preparations and examples serve to illustrate the invention. They should not be construed as narrowing it, or limiting its scope in any way.

EXPERIMENTAL

General Methods

Unless otherwise specified, all reactions were carried out in an oven-dried (>110° C.) round-bottom flask equipped with a Teflon™ coated magnetic stir bar and a rubber septum under a positive pressure of argon. Sensitive solvents and reagents were transferred by syringe or stainless steel cannula. Reactions were run at 20° C. unless otherwise noted.

Unless otherwise specified, reaction temperatures refer to the external temperatures of the bath in which the reaction vessel was partially immersed. The term "0° C." refers to an ice water bath.

The terms "removal of the solvent in vacuo" and "concentration" refer to evaporation of solvent using a Buchi rotary evaporator equipped with a vacuum pump. Residual solvents were removed from nonvolatile samples using a vacuum line held at 0.1-1.0 mg.

Reagents and Solvents

The starting material compounds, solvents, reagents, etc. described herein are available from commercial sources or are easily prepared from literature references by one of skill in the art. See Chem Sources USA, published annually by Directories Publications, Inc. of Boca Raton, Fla. Also see The Aldrich Chemical Company Catalogue, Milwaukee, Wis. The starting materials are used as obtained unless otherwise noted. Dichloromethane and toluene were passed through an alumina drying-column (Solvtek, Inc.). Pyridine and diisopropylmethane were distilled from calcium hydride under nitrogen. Denatured chloroform was passed through a pad of basic alumina and stored over anhydrous potassium.

Chromatography

Analytical thin-layer chromatography (TLC) was performed by using glass or aluminum-backed silica plates coated with a 0.25 mm thickness of silica gel 60 $F_{254}$ (Merck), visualized with an ultraviolet light, followed by exposure to p-anisaldehyde solution, potassium permanganate solution, or ceric ammonium molybdate solution and heating.

The term "flash column chromatography" refers to column chromatography using Merck silica gel 60 (230-400 mesh) as described by Still et al., "Rapid chromatographic technique for preparative separations with mrioderate resolution", *J. Org. Chem.*, 43, 2923-2925 (1978). The eluent composition is indicated following the description of purification (percentage of the more polar solvent in the less polar solvent). The size of the column, the amount of silica gel loaded and the volume of eluent required for packing and elution were chosen based on the method described by Still.

Physical and Spectroscopic Data

Optical rotations were measured on a JASCO DIP-360 digital polarimeter using solutions in indicated solvents. All values are reported in the following format: $[\alpha]_D$ (temperature of measurement)=specific rotation (concentration of the solution reported in units of 10 mg sample per 1 mL solvent, solvent used).

Proton and Carbon NMR spectra were measured on either a Varian Mercury-400 ($^1$H at 400 MHz, $^{13}$C at 100 MHz) or a Varian INOVA-500 ($^1$H at 500 MHz, $^{13}$C at 125 MHz) magnetic resonance spectrometer. $^1$H chemical shifts are reported in parts per million (ppm) using residual $CHCl_3$ ($\delta$ 7.24) as the internal standard, coupling constants are reported in Hertz (Hz). Proton ($^1$H) NMR information is tabulated in the following format: multiplicity, number of protons, coupling constant, and structural assignments (in the format of "carbon-numbering-H" (the natural product numbering system is used)). Multiplicities are reported as follows: s=singlet, d=doublet, t=triplet, q=quartet, sept=septet, dd=doublet of doublets, td=triplet of doublets, ddd=doublet of doublet of doublets, m=multiplet. Proton decoupled $^{13}$C NMR spectra are reported in ppm ($\delta$) relative to residual $CHCl_3$ ($\delta$ 77.0) unless noted otherwise.

Infrared spectra were recorded on a Perkin-Elmer Spectrum BX Fourier Transform Spectrometer using neat material on a NaCl plate. All values are reported in wavenumbers ($cm^{-1}$) and are externally referenced to polystyrene film (1601 $cm^{-1}$). High-resolution mass spectra (HRMS) were recorded at the NIH regional mass spectrometry facility at the

Example 1

Generation of Enol Acetate

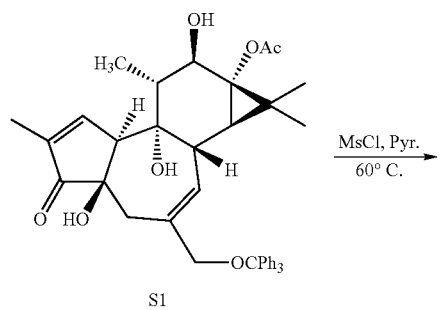

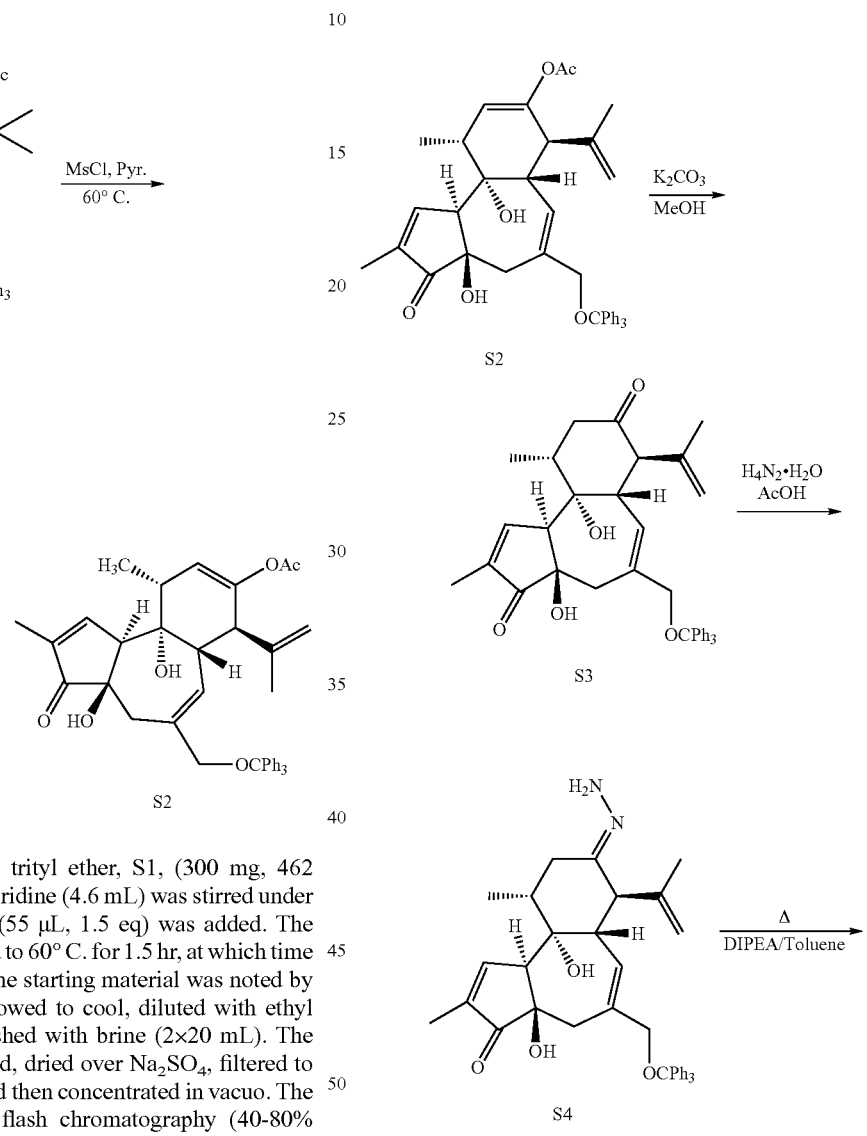

Phorbol-12-acetate-C-20 trityl ether, S1, (300 mg, 462 μmol) in freshly distilled pyridine (4.6 mL) was stirred under argon and mesyl chloride (55 μL, 1.5 eq) was added. The reaction mixture was heated to 60° C. for 1.5 hr, at which time complete consumption of the starting material was noted by TLC. The mixture was allowed to cool, diluted with ethyl acetate (100 mL), and washed with brine (2×20 mL). The organic phase was separated, dried over $Na_2SO_4$, filtered to remove the drying agent and then concentrated in vacuo. The residue was subjected to flash chromatography (40-80% EtOAc/pentane, ~25 g silica, ID 25 mm) to give the product S2 as an off-white foam (220 mg, 76%).

TLC $R_f$=0.76 (40% EtOAc/Pentane), one black spot in p-anisaldehyde (visible under UV lamp);

$[\alpha]_D^{23.5}$=+61.3° (c 0.61, $CHCl_3$)

$^1$H NMR (500 MHz, $CDCl_3$): δ 7.56 (br s, 1H, C1-H), 7.42-7.20 (m, 15H, Ar—H), 5.66 (br s, 1H, C7-H), 5.04 (s, 1H), 5.00 (s, 1H), 4.96 (s, 1H), 3.41 (m, 3H), 3.26 (m, 1H), 3.20 (br s, 1H), 2.42 (d, J=19 Hz, 1H), 2.36 (s, 1H), 2.17 (br s, 1H), 2.14 (br s, 1H), 2.10 (s, 3H), 1.80 (dd, J=1.2, 2.7 Hz, 3H), 1.65 (s, 3H), 1.06 (d, J=7.32 Hz, 3H) ppm.

$^{13}$C NMR (125 MHz, $CDCl_3$): δ 208.9, 169.8, 159.7, 147.4, 144.1 (3), 142.5, 136.8, 135.4, 128.6 (6), 127.8 (6), 126.9 (3), 124.8, 121.2, 116.6, 86.8, 76.7, 73.5, 68.8, 55.0, 48.9, 42.8, 39.4, 37.1, 20.6, 17.9, 16.8, 10.2

FT-IR (thin film): ν 3425, 3058, 2921, 1704 (br), 1448, 1372, 1218, 758 $cm^{-1}$.

HRMS: Calcd.: 653.2879 (for $C_{41}H_{42}O_6Na$). found: 653.2878

Example 2

Production of the Intermediate Acetoxypyrazoline

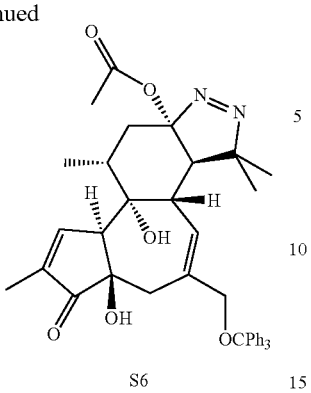

S6

The enolacetate S2 (92 mg, 146 µmol) in methanol (1.5 mL) was stirred while K$_2$CO$_3$ (30 mg, 1.5 eq.) was added in a single portion. After 30 minutes of vigorous stirring consumption of the starting material and complete conversion to ketone S3 was noted. Acetic acid (33 µL, 4 eq) and hydrazine hydrate (11 µL, 1.5 eq.) were added. The reaction was allowed to stir for an additional 1 hour and monitored by TLC (100% EtOAc). Generation of the hydrazone intermediate S4 is indicated by the formation of a large, green baseline spot (PA Stain). Once the formation of the hydrazone is complete, basic alumina (500 mg) and EtOAc (15 mL) were added to the reaction mixture. The mixture was filtered through a pad of CELITE® and concentrated. The off-white hydrazone solid was redissolved in toluene (2.0 mL) and DIPEA (200 µL) in a sealed tube. The solution was degassed (freeze-pump-thaw, 3 times) and flushed with argon. The reaction vessel was capped and heated to 150° C. for 13 hours and allowed to cool. The volatiles were removed under reduced pressure, and the vessel was back-filled with argon. (The pyrazoline S5 must be handled under inert atmosphere to avoid rapid oxidation by air). The crude was redissolved in dichloromethane (1.5 mL) and cooled to 0° C. Lead (IV) acetate (67 mg, 1.1 eq.) was added in a single portion. The reaction was allowed to stir 30 minutes, quenched with NaHCO$_3$ (aq., sat., 3 mL), and extracted with dichloromethane (5×5 mL). The combined organic layers were dried over Na$_2$SO$_4$, filtered to remove the drying agent, and concentrated. The residue was subjected to flash chromatography (0 to 40% EtOAc in pentane, ID 25 mm, ~25 g silica) and concentrated to give the product S6 as a light yellow oil (38.7 mg, 40.2%). Physical analysis showed:

TLC R$_f$=0.47 (50% EtOAc/Pentane), one purple spot in p-anisaldehyde (visible under UV lamp); [α]$_D^{23.5}$=+60.7° (c 1.00, CH$_2$Cl$_2$)

$^1$H NMR (500 MHz, CDCl$_3$): δ 7.52 (t, J=1.8 Hz, 1H C1-H), 7.40-7.43 (m, 5H, Ar—H), 7.26-7.31 (m, 5H, Ar—H), 7.22-7.25 (m, 5H, Ar—H), 5.62 (d, J=3.4 Hz, 1H, C7-H), 3.50 (s, 2H, C20-H), 3.28 (dd, 1H, J=4.9 Hz, 12.1 Hz, 1H, C8-H), 2.95 (s, 1H, C10-H), 2.47-2.53 (m, 2H, C11-H and C5-H), 2.36 (d, 1H, C14-H), 2.18 (d, 1H, J=19.3 Hz, C5-H), 2.14 (d, 1H, J=16.1 Hz, C12-H), 2.13 (s, 3H, OCOCH$_3$), 2.09 (s, 1H, OH), 2.07 (s, 1H, OH), 1.80 (dd, 3H, J=1.4 Hz, 2.8 Hz, C19-H), 1.68 (s, 3H, gem-Me), 1.52 (dd, 1H, 8.9 Hz, 14.5 Hz, C12-H), 1.34 (s, 3H, gem-Me), 1.23 (d, 3H, J=7.3 Hz) ppm.

$^{13}$C NMR (125 MHz, CDCl$_3$): δ 208.41, 168.80, 157.07, 144.02, 138.42, 136.97, 128.64 (6C), 127.94 (6C), 127.20 (3C), 125.89 (3C), 119.40, 92.94, 87.03, 77.85, 73.76, 68.72, 57.33, 45.10, 40.20, 39.36, 35.93, 31.66, 27.89, 22.57, 22.09, 18.13, 10.46 ppm.

FT-IR (thin film): ν 3411, 2972, 2933, 1746, 1705, 1650, 1596, 1448, 1236, 1030, 910, 732 cm$^{-1}$.

HRMS: Calcd.: 683.3097 (for C$_{41}$H$_{44}$N$_2$O$_6$Na). found: 683.3093

Example 3

Removal of Trityl Protecting Group

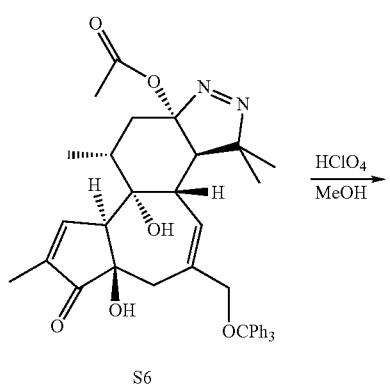

S6

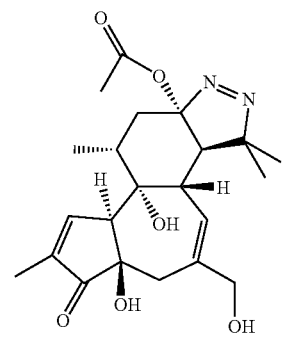

S7

A solution of S6 (5.0 mg, 7.6 µmol) in methanol (750 µL) was stirred at room temperature under air. HClO$_4$ (70% in H$_2$O, 7.5 µL) was added, and the reaction was allowed to stir for 20 min. The mixture was neutralized by the addition of NaHCO$_3$ (solid, 20 mg) and stirred for 10 minutes. The crude mixture was filtered through CELITE® and the volatiles were removed under reduced pressure. The residue was subjected to flash chromatography (100% ethyl acetate, ID 8 mm, ~1 g silica) to give S7 as a white solid (2.9 mg, 90%). Physical measurement showed:

TLC R$_f$=0.08 (100% EtOAc), one black spot in p-anisaldehyde (visible under UV lamp); [α]$_D^{23.5}$=+45.6° (c 0.34, CHCl$_3$)

$^1$H NMR (500 MHz, CDCl$_3$): δ 7.51 (s, 1H, C1-H), 5.50 (d, J=3.9 Hz, 1H, C7-H), 4.04 (d, J=12.8 Hz, 1H, C20-H), 4.02 (d, J=13.1 Hz, 1H, C20-H), 3.25 (dd, J=4.9, 11.7 Hz. 1H, C8-H), 3.03 (br s, 1H, C10-H), 2.55-2.49 (m, 2H, C11-H and C5-H), 2.42 (d, J=19.2 Hz, 1H, C5-H), 2.34 (d, J=12.0 Hz, 1H, C14-H), 2.16 (br s, 1H, OH), 2.12 (s, 3H, CH3COO), 1.83 (dd, J=1.5, 2.8 Hz, 3H, C19-H), 1.80 (br s, 1H, OH), 1.62 (s, 3H, gem-Me), 1.56 (dd, J 8.9, 14.5 Hz, 1H, C12-H), 1.27 (s, 3H, gem-Me), 1.23 (d, J=7.3 Hz, 3H, C18-H).

$^{13}$C NMR (125 MHz, CDCl$_3$): δ208.6, 169.0, 157.3, 140.7, 137.1, 127.0, 119.3, 93.1, 78.2, 73.9, 68.3, 57.3, 45.3, 40.3, 38.9, 36.0, 32.0, 28.1, 22.8, 22.2, 18.3, 10.6 ppm.

FT-IR (thin film): ν 3405, 1969, 2924, 1737, 1705, 1381, 1366, 1432, 1030, 755 cm$^{-1}$.

HRMS: Calcd.: (for $C_{22}H_{30}N_2O_6Na$): 441.2002. Found: 441.2008

Example 4

Formation of Cyclopropane Ring Structure

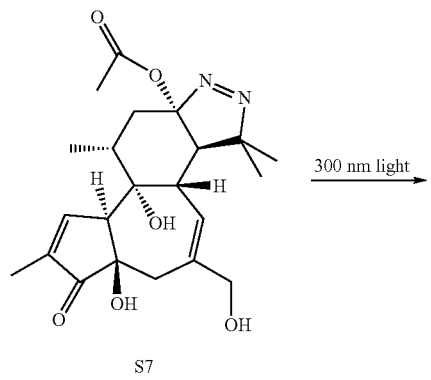

S7

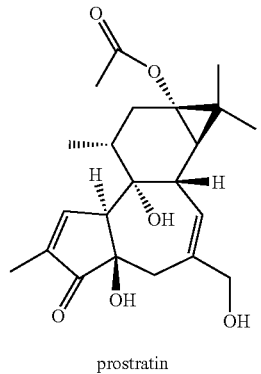

prostratin

A solution of the S7 (2.9 mg, 6.9 μmol) in benzene/EtOAc (1:1, 600 μL) was placed in a disposable glass vial under argon atmosphere. The solution was irradiated with UV light (300 nm) using a Rayonet photochemical reactor at room temperature for 20 min until TLC indicated complete consumption of the starting material. The reaction mixture was concentrated under reduced pressure and the resultant syrup was purified by silica gel column chromatography (80% ethyl acetate/pentane, ID 8 mm, ~1 g silica) to afford 12-deoxyphorbol-13-acetate (prostratin) as a white powder (2.5 mg, 92%).

On a preparative scale, a solution of S7 (142 mg, 0.387 mmol) in methanol (76 mL) was placed in a round-bottom flask under argon atmosphere. The solution was irradiated with UV light (300 nm) using a Rayonet photochemical reactor at room temperature for 11 h. The reaction mixture was concentrated under reduced pressure and the resultant syrup was purified by flash column chromatography (100% ethyl acetate) to afford prostratin (69 mg) and recovered S7 (49 mg). The recovered material was subjected to the previously described photolysis condition to afford addition 32 mg of prostratin and recovered S7 (15 mg) after flash chromatography. The total amount of obtained prostratin is 101 mg (67% yield, 74% based on the recovered starting material). The analysis of the product showed the following properties:

TLC $R_f$=0.27 (60% EtOAc/Pentane), one black spot stained with p-anisaldehyde (visible under UV lamp);

$[\alpha]D^{23.5}$=+69.0° (c 0.16, MeOH)

$^1$H NMR (500 MHz, in 0.75 ml of CDCl$_3$ exchanged with 10 μl of D$_2$O): δ7.59 (s, 1H, C1-H), 5.66 (d, 1H, J=5.0 Hz, C7-H), 4.02 (d, 1H, J=12.6 Hz, C20-H), 3.96 (d, 1H, J=12.5 Hz, C20-H), 3.26 (t, 1H, J=2.6 Hz, C10-H), 2.99 (t, 1H, J=5.3 Hz, C8-H), 2.51 (d, 1H, J=9.5 Hz, C5-H), 2.45 (d, 1H, J=8.9 Hz, C5-H), 2.07 (dd, 1H, J=7.1 Hz, 14.5 Hz, C12-H), 2.06 (s, 3H, OCOCH$_3$), 1.95-1.99 (m, 1H, C11-H), 1.77 (dd, 3H, J=2.3 Hz, 3.8 Hz, C19-H), 1.56 (dd, 1H, J=11.3 Hz, 14.6 Hz, C12-H), 1.19 (s, 3H, C16-H), 1.06 (s, 3H, C17-H), 0.88 (d, 3H, 6.4 Hz, C18-H), 0.84 (d, 1H, J=5.3 Hz, C14-H) ppm.

$^{13}$C NMR (125 MHz, d$_6$-benzene): δ208.4, 172.7, 160.7, 140.5, 132.9, 129.8, 76.1, 73.9, 68.0, 63.8, 56.2, 39.5, 38.8, 36.7, 32.9, 32.4, 23.3, 22.7, 20.7, 18.9, 15.5, 10.1 ppm.

FT-IR (thin film): ν 3391, 2921, 1708, 1262 cm$^{-1}$.

HRMS: Calcd.: 413.1940, (for $C_{22}H_{30}O_6Na$). Found: 413.1946

The analytical data for the synthetic material described below matches those for an authentic sample of prostratin. (An authentic sample of prostratin (cat. No. P-4462, Lot BS-112) was purchased from LC laboratories, Woburn, Mass.)

Characterization was obtained as described above. See Table 2.

TABLE 2

Comparison Chart for Prostratin characterization data

| Carbon | $^1$H-NMR (500 MHz) | | $^{13}$C-NMR (125 MHz) | |
| --- | --- | --- | --- | --- |
| | Synthetic | Authentic | Synthetic | Authentic |
| 1 | 7.59 (br s) | 7.59 (br s) | 160.7 | 160.7 |
| 2 | | | 132.9 | 132.9 |
| 3 | | | 208.4 | 208.4 |
| 4 | | | 73.9 | 73.9 |
| 5 | 2.51 (d, J = 9.5 Hz) 2.45 (d, J = 8.9 Hz) | 2.51 (d, J = 8.9 Hz) 2.45 (d, J = 8.9 Hz) | 38.8 | 38.8 |
| 6 | | | 140.5 | 140.4 |
| 7 | 5.66 (d, J = 5.0 Hz) | 5.66 (d, J = 5.0 Hz) | 129.8 | 129.8 |
| 8 | 2.99 (t, J = 5.3 Hz) | 3.00 (t, J = 5.3 Hz) | 39.5 | 39.5 |
| 9 | | | 76.1 | 76.1 |
| 10 | 3.26 (t, J = 2.6 Hz) | 3.26 (t, J = 2.7 Hz) | 56.2 | 56.2 |
| 11 | 1.95-1.99 (m) | 1.95-1.99 (m) | 36.7 | 36.7 |
| 12 | 1.56 (dd, J = 11.3 Hz, 14.6 Hz) 2.07 (dd, J = 7.1 Hz, 14.5 Hz) | 1.56 (dd, J = 11.3 Hz, 14.7 Hz) 2.07 (dd, J = 6.8 Hz, 14.5 Hz) | 32.4 | 32.4 |
| 13 | | | 63.8 | 63.8 |
| 14 | 0.84 (d, J = 5.3 Hz) | 0.84 (d, J = 5.2 Hz) | 32.9 | 32.9 |
| 15 | | | 22.7 | 22.7 |
| 16 | 1.19 (s, 3H) | 1.19 (s, 3H) | 23.3 | 23.3 |
| 17 | 1.06 (s, 3H) | 1.06 (s, 3H) | 15.5 | 15.5 |
| 18 | 0.88 (d, 3H, 6.4 Hz) | 0.88 (d, 3H, 6.5 Hz) | 18.9 | 18.9 |
| 19 | 1.77 (dd, 3H, J = 1.3 Hz, 2.8 Hz) | 1.77 (dd, J = 1.2 Hz, 1.7 Hz) | 10.1 | 10.1 |
| 20 | 4.02 (d, J = 12.6 Hz) 3.96 (d, J = 12.5 Hz) | 4.02 (d, J = 12.7 Hz) 3.96 (d, J = 12.6 Hz) | 68.0 | 68.0 |
| 21 | | | 172.7 | 172.7 |
| 22 | 2.06 (s, 3H) | 2.06 (s, 3H) | 20.7 | 20.7 |

Example 5

Phorbol to Prostratin, Alternate Route

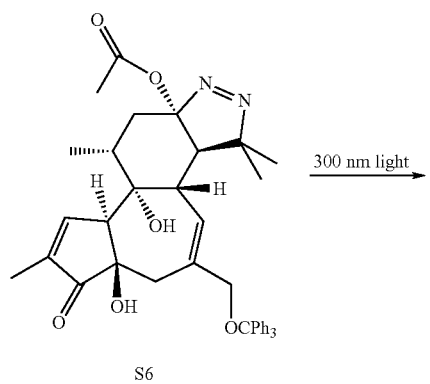

The acetoxypyrazoline S6 (10 mg, 0.015 mmol) was dissolved in $d_6$-benzene (0.75 ml) in a septum-capped NMR tube under nitrogen atmosphere. The solution was irradiated with UV light (300 nm) using a Rayonet photochemical reactor at room temperature for 20 min until TLC indicated complete consumption of the starting material. The reaction mixture was concentrated under reduced pressure and the resultant syrup was purified by silica gel column chromatography (10%→30% ethyl acetate/pentane, ID 25 mm, ~25 g silica) to afford S8 as a pale yellow film (7.7 mg, 81% yield). The product was identified by:

TLC $R_f$=0.75 (50% EtOAc/Pentane), one grey spot in p-anisaldehyde (visible under UV lamp); $[\alpha]_D^{23.5}$=+41.4° (c 0.77, $CH_2Cl_2$)

$^1$H NMR (500 MHz, $CDCl_3$): δ 7.59 (s, 1H, C10-H), 7.41-7.43 (m, 6H, Ar—H), 7.27-7.30 (m, 6H, Ar—H), 7.20-7.22 (m, 3H, Ar—H), 5.62 (d, 1H, J=4.0 Hz, C7-H), 5.23 (brs, 1H, OH), 3.51 (s, 2H, C20-H), 3.27 (brs, 1H, C10-H), 2.93 (t, 1H, J=5.1 Hz, C8-H), 2.51 (d, 1H, J=8.8 Hz, C5-H), 2.39 (d, 1H, J=8.8 Hz, C5-H), 2.06 (s, 3H, $OCOCH_3$), 2.05 (s, 1H, OH), 2.02-2.08 (m, 1H, C12-H), 1.99 (d, 1H, J=1.0 Hz, C20-OH), 1.92-1.97 (m, 1H, C11-H), 1.77 (dd, 3H, J=1.2 Hz, 2.8 Hz, C19-H), 1.56 (m, 1H, C12-H), 1.19 (s, 3H, gem-diMe), 1.07 (s, 3H, gem-diMe), 0.87 (d, 3H, J=6.4 Hz, C18-H), 0.82 (d, 1H, J=5.2 Hz, C14-H) ppm.

$^{13}$C NMR (125 MHz, $CDCl_3$): δ 209.5, 173.4, 161.6, 144.3, 137.7, 132.9, 130.9, 129.0, 128.0, 127.2, 87.1, 76.0, 74.2, 69.6, 63.9, 56.0, 39.6, 39.5, 36.6, 32.6, 32.1, 23.5, 22.9, 21.6, 18.8, 15.61, 10.4 ppm.

FT-IR (thin film): ν 3417, 2917, 1709, 1626, 1448, 1259, 1051, 705 $cm^{-1}$.

HRMS: Calcd.: (for $C_{41}H_{44}O_6Na$): 655.3036. Found: 655.3033

Example 6

Removal of Trityl Protecting Group, Alternate Route

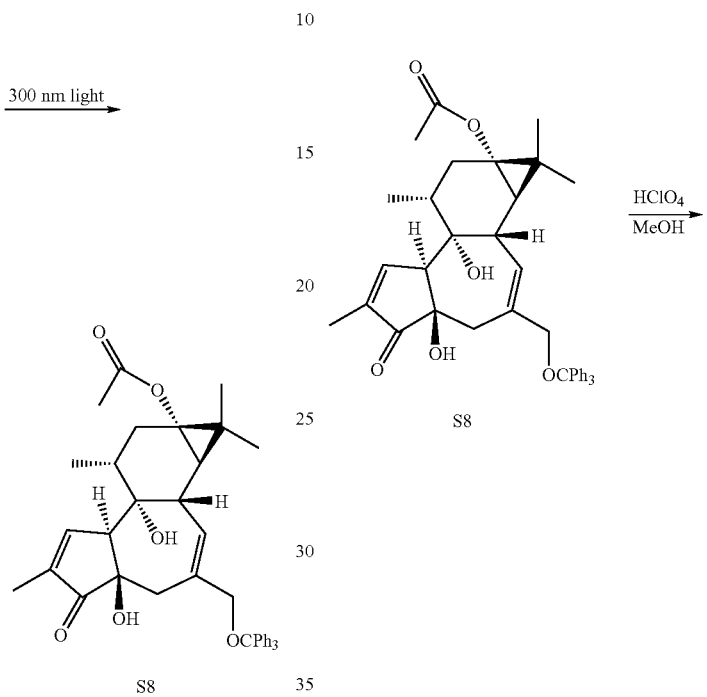

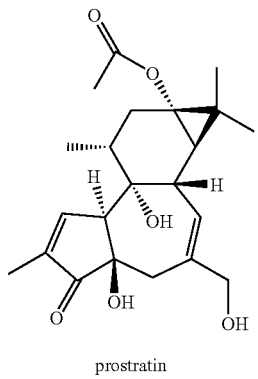

prostratin

The trityl ether (7.0 mg, 0.011 mmol) was dissolved in methanol (1.0 ml) in a Teflon-capped vial equipped with a magnetic stir bar under nitrogen atmosphere. Perchloric acid (10 μl) was added via a syringe dropwise over 5 sec, and the mixture was stirred at room temperature for 15 min until TLC indicated complete consumption of the starting material. Solid sodium bicarbonate (100 mg) was added to neutralize the reaction mixture, and the resultant suspension was stirred at ambient temperature for 5 min. Ethyl acetate (10 ml) was added to the reaction mixture, and the mixture was filtered through CELITE® to remove the solid residue. The filtrate was concentrated under reduced pressure, and the resultant syrup was purified by silica gel flash chromatography (40%→60% ethyl acetate/petroleum ether) to obtain a colorless film. For characterization purposes, this product was further purified by reverse-phase HPLC and lyophilized to

Example 7

An Alternative Protecting Group-Free Route to Prostratin

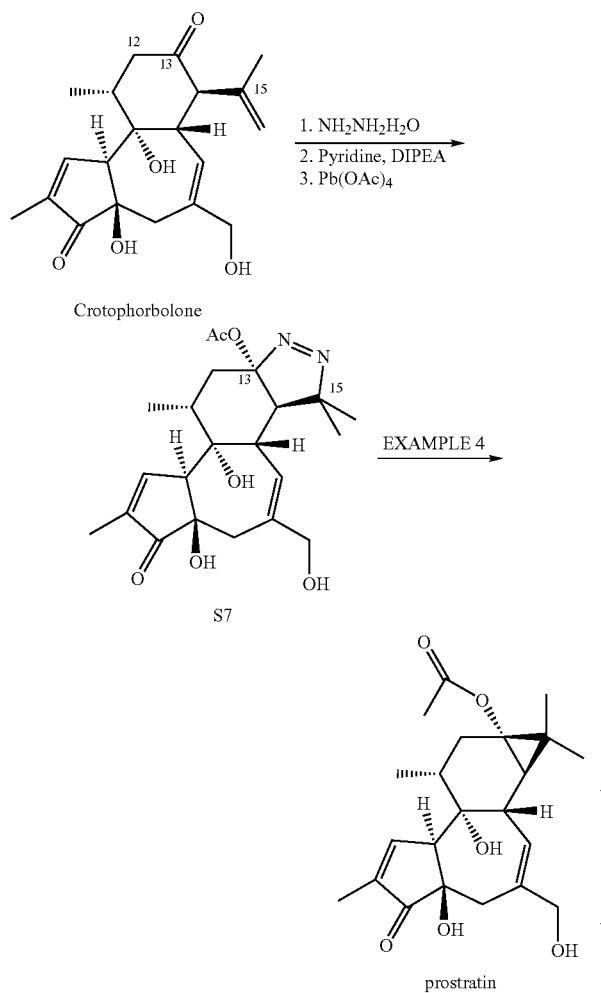

A solution of crotophorbolone (21.2 mg, 54.3 μmol) in methanol (5 mL) was stirred at room temperature under air. Acetic acid (18 μL, 5 equiv.) and hydrazine hydrate (6 μL, 2 equiv.) were added. The reaction was allowed to stir until the consumption of starting material was noted by TLC (100% Ethyl Acetate), 1 hour. Basic alumina (1 g) and ethyl acetate (10 mL) were added. The slurry was allowed to stir for 10 minutes at ambient temperature. The crude was passed through a pad of celite (1 g) and concentrated in vacuo. The crude was redissolved in pyridine (900 μL) and DIPEA (100 μL) and transferred to a Teflon-capped resealable pressure tube. The solution was sparged with bubbling argon for 10 minutes and the tube was sealed. The mixture was heated to 150° C. for 48 hr. Once the reaction was deemed complete by TLC (30% MeOH in EtOAc), the solvent was removed in vacuo, and the vessel was backfilled with argon to avoid air oxidation of the sensitive pyrazoline (S) (A. L. Baumstrak, M. Dotrong, P. C. Vasquez, *Tetrahedron Lett.* 28, 1963-1966 (1987)). The crude was redissolved in CH$_2$Cl$_2$ (5 mL) and cooled to 0° C. A solution of Pb(OAc)$_4$ (30 mg, 1.1 equiv.) in CH$_2$Cl$_2$ (5 mL) was added to the pyrazoline at 0° C., and allowed to stir for 30 minutes. The reaction was stopped by addition of NaHCO$_3$ (3 mL), and extracted with EtOAc (4×10 mL). The combined organic layers were dried over Na$_2$SO$_4$ (s) and concentrated. The crude was subjected to flash chromatography to give diazene S7 as an off white foam (10.9 mg, 43%). The analytical data match those given in EXAMPLE 3.

Example 8

Phorbol to DPP

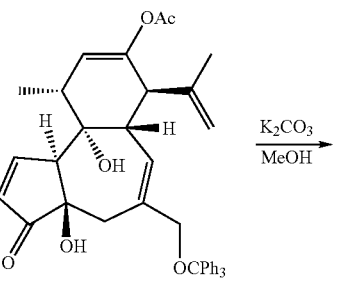

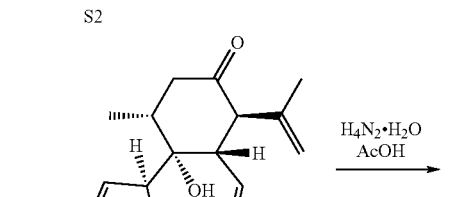

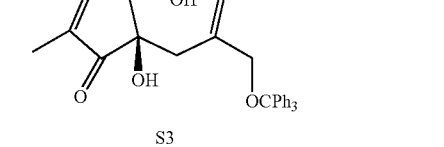

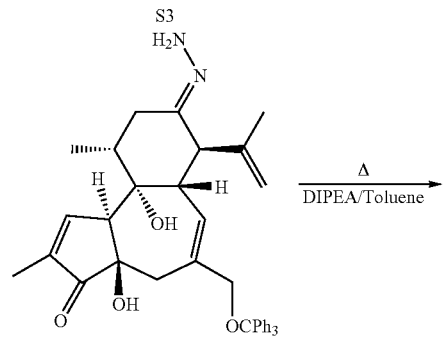

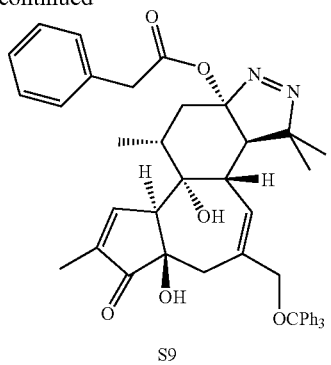

S9

A solution of substrate S2 (15.2 mg, 24 μmol) was stirred in methanol (240 μL) under air at room temperature. K$_2$CO$_3$ (6 mg, 2 eq.) was added in a single portion. After stirring vigorously for 30 min, complete conversion to ketone S3 was observed by TLC. Acetic acid (5 μL, 5 eq) and hydrazine hydrate (4 μL, 5 eq.) were added, and the reaction was allowed to stir for 1 hour and monitored by TLC (100% ethyl acetate, PA Stain). Following complete consumption of the starting material, basic alumina (100 mg) was added, and the reaction was diluted with ethyl acetate (5.0 mL). The mixture was passed through a pad of CELITE® with ethyl acetate rinse (5 mL). The organic solvent was removed under reduced pressure to give the crude hydrazone S4 as an off-white solid. The solid was resuspended in a mixture of toluene/DIPEA (9:1, 2 mL) in a Teflon-capped sealed tube under argon. The mixture was heated to 150° C. for 16 hours. After cooling, the solvent was removed under reduced pressure, and the vessel backfilled with argon. Exposure of the crude pyrazoline S5 to air must be avoided. The crude was redissolved in dichloromethane (1 mL), and a pre-mixed solution of Pb(OAc)$_4$ (1.2 eq.) and phenylacetic acid (20 eq.) in dichloromethane (3 mL, pre-mixed for 30 min at ambient temperature) was added at 0° C. The reaction was allowed to warm to room temperature over one hour, quenched with aqueous NaHCO$_3$ (sat., 3 mL), and extracted with ethyl acetate (3×5 mL). The combined organic layers were dried over Na$_2$SO$_4$, filtered to remove drying agent, and concentrated. The residue was subjected to flash chromatography (60% ethyl acetate in pentane, ID 25 mm, ~25 g silica) to give S9 as a white foam (8.1 mg, 46%). The product was identified by:

TLC R$_f$=0.25 (50% EtOAc/Pentane), one purple spot in p-anisaldehyde (visible under UV lamp); [α]$_D^{2.35}$=+25.6° (c 0.53, CHCl$_3$)

$^1$H NMR (500 MHz, CDCl$_3$): δ 7.43-8.46 (m, 17H, Ar—H, C1-H), 7.24-7.20 (m, 4H, Ar—H), 5.56 (d, J=3.5 Hz, 1H, C7-H), 3.71 (s, 2H PhCH2COO—), 3.47 (s, 2H, C20-H), 3.23 (dd, J=5, 12.2 Hz, 1H, C8-H), 2.90 (br s, 1H, C10-H), 2.52-2.42 (m, 2H, C11-H, C5-H), 2.33 (d, J=11.6 Hz, 1H, C14-H), 2.16 (d, J=19.2 Hz, 1H, C5-H), 2.05 (br d, J=14.5 Hz, C12-H), 2.00 (s, 1H, OH) 1.79 (dd, J=1.3, 2.7 Hz, 3H, C19-H), 1.72 (s, 1H, OH), 1.65 (s, 3H, gem-Me), 1.45 (dd, J=8.9, 14.4 Hz, 1H, C12-H), 1.31 (s, 3H, gem-Me), 0.92 (d, J=7.5 Hz, 3H, C18-H) ppm.

$^{13}$C NMR (125 MHz, CDCl$_3$): δ 208.4, 169.1, 157.0, 143.9, 138.1, 136.8, 133.2, 129.3 (2), 128.9 (2), 128.5 (6), 127.8 (6), 127.4, 127.1 (3), 125.9 (3), 93.0, 86.9, 77.7, 73.6, 68.7, 57.1, 44.8, 42.3, 40.0, 39.3, 35.8, 31.3, 27.8, 22.5, 17.5, 10.3 ppm.

FT-IR (thin film): ν 3418, 2967, 2923, 1745, 1708, 1448, 1222, 1051, 706 cm$^{-1}$.

HRMS: Calcd.: (for C$_{47}$H$_{48}$N$_2$O$_6$Na): 759.3410. Found: 759.3415

Example 9

Removal of Trityl Protecting Group

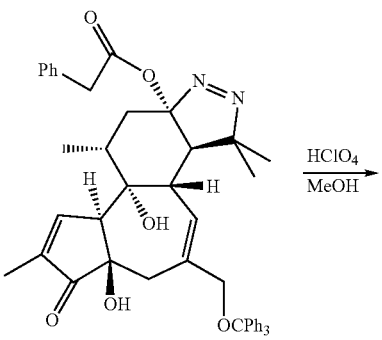

S9

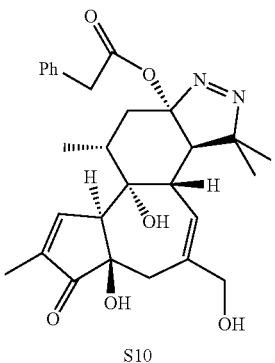

S10

A solution of S9 (12.2 mg, 16.6 μmol) in MeOH (1.0 mL) was stirred at room temperature, and HClO$_4$ (70% in H$_2$O, 10 μL) was added. The reaction was allowed to stir at ambient temperature for 1 hr until TLC indicated complete consumption of the starting material. The mixture was neutralized by addition of solid NaHCO$_3$ (20 mg), diluted with EtOAc (5 mL) and filtered through a pad of CELITE®. The crude filtrate was concentrated under reduced pressure, and subjected to flash chromatography (100% EtOAc, ID 8 mm, ~1 g silica) to provide the S10 as a white powder (6.5 mg, 80%). The product was identified by:

TLC R$_f$=0.20 (100% EtOAc), one black spot in p-anisaldehyde (visible under UV lamp); [α]$_D^{23}$=5+30.9° (c 0.29, CHCl$_3$)

$^1$H NMR (500 MHz, CDCl$_3$): δ 7.44-7.27 (m, 6H, Ar—H, C1-H), 5.47 (d, J=3.8 Hz, 1H, C7-H), 4.01 (dd, J=13, 22 Hz, 2H, C20-H), 3.65 (s, 2H, PhCH$_2$COO), 3.21 (dd, J=4.1, 11.4 Hz, 1H, C8-H), 2.98 (br s, 1H, C10-H), 2.53-2.39 (m, 2H, C11-H and C5-H), 2.32 (d, J=11.9 Hz, 1H, C5-H), 2.11 (br s, 1H, C14-H), 2.05 (d, J=14.5 Hz, C12-H), 1.92 (br s, 1H, OH), 1.81 (s, 3H, C19-H), 1.59 (s, 3H, gem-Me), 1.46 (dd, J=9.2, 14.7 Hz, C12-H), 1.23 (s, 3H, gem-Me), 0.91 (d, J=7.5 Hz, 3H, C18-H) ppm.

$^{13}$C NMR (125 MHz, CDCl$_3$): δ 216.7, 208.3, 169.1, 156.9, 140.2, 136.8, 133.1, 129.3 (2), 128.9 (2), 127.5, 126.8, 119.5, 93.0, 77.8, 73.6, 68.1, 56.9, 44.8, 42.4, 40.0, 38.6, 35.8, 31.4, 27.8, 22.5, 17.4, 10.3 ppm.

FT-IR (thin film): ν 3400, 2972, 2928, 1707 (br), 1630, 1253, 1148, 1020 cm$^{-1}$.

HRMS: Calcd.: (for $C_{28}H_{34}N_2O_6Na$): 517.2315. Found: 517.2309

Example 10

Formation of Cyclopropane Ring Structure

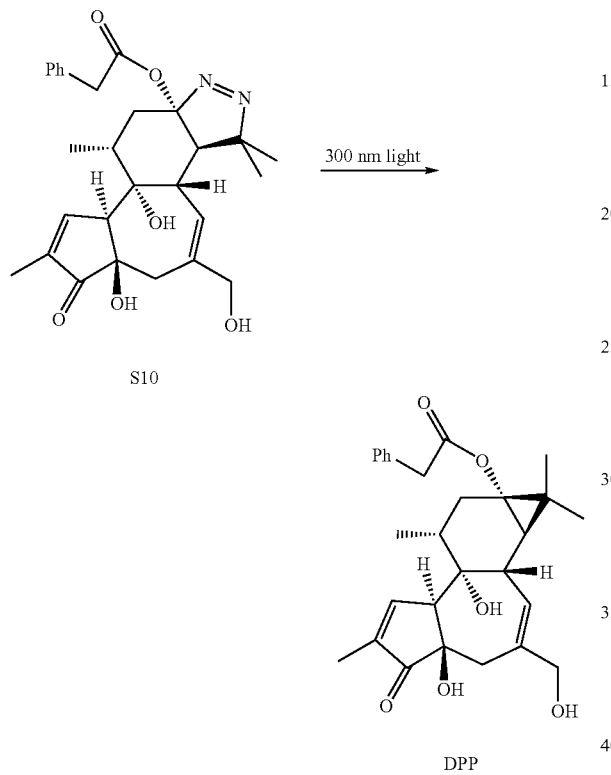

A solution of S10 (5.4 mg, 10.9 μmol) in benzene/EtOAc (1:1, 1 mL) was stirred at room temperature in a disposable glass vial flushed with argon. The solution was irradiated with UV light (300 nm) using a Rayonet photochemical reactor at room temperature for 45 min. until TLC indicated complete consumption of the starting material. The reaction mixture was concentrated under reduced pressure, and subjected to flash (100% EtOAc, ID 8 mm, ~1 g silica) to give 12-deoxy-phorbol-13-phenylacetate (DPP) as a white powder (4.4 mg, 87%). The product was characterized by:

TLC $R_f$=0.45 (100% EtOAc), one black spot in p-anisaldehyde (visible under UV lamp)

$[α]_D^{23}$=5+35.7° (c 0.44, CHCl$_3$)

$^1$H NMR (500 MHz, CDCl$_3$ after D$_2$O shake): δ 7.57 (br s, 1H, C1-H), 7.35-7.24 (m, 5H, Ar—H), 5.63 (d, J=4.5 Hz, 1H, C7-H), 4.02 (d, J=12.8 Hz, 1H, C20-H), 3.94 (d, J=12.8 Hz, 1H, C20-H) 3.62 (d, J=14.7 Hz, 1H, CH2Ph), 3.58 (d, J=14.7 Hz, 1H, CH2Ph), 3.24 (dd, J=2.7, 2.7 Hz, 1H, C10-H), 2.94 (m, 1H, C8-H), 2.50 (d, J=19 Hz, 1H, C5-H), 2.43 (d, J=19 Hz, 1H, C5-H), 3.07 (dd, J=7.0, 14.0 Hz, 1H, C12-H), 1.99-1.95 (m, 1H, C11-H), 1.76 (dd, J=1.4, 2.9 Hz, 3H, C19-H), 1.54 (dd, J=11.1, 14.5 Hz, 1H, C12-H), 1.03 (br s, 6H, C16-H and C17-H), 0.86 (d, J=6.5 Hz, 3H, C18-H), 0.75 (d, J=5.4 Hz, 1H, C14-H) ppm.

$^{13}$C NMR (125 MHz, CDCl$_3$): δ 209.4, 173.6, 161.4, 139.8, 133.2, 132.8, 130.2, 129.3 (2), 128.6 (2), 127.3, 76.1, 73.7, 68.2, 64.0, 55.7, 41.7, 39.1, 38.6, 36.3, 32.4, 31.7, 23.0, 22.9, 18.5, 15.3, 10.1 ppm.

FT-IR (thin film): ν 3399, 2921, 1707, 1625, 1455, 1246, 1133, 1015 cm$^{-1}$.

HRMS: Calcd.: (for $C_{28}H_{34}O_6Na$): 489.2253. Found: 489.2256

Example 11

An Alternative Protecting Group-Free Route from Phorbol to DPP

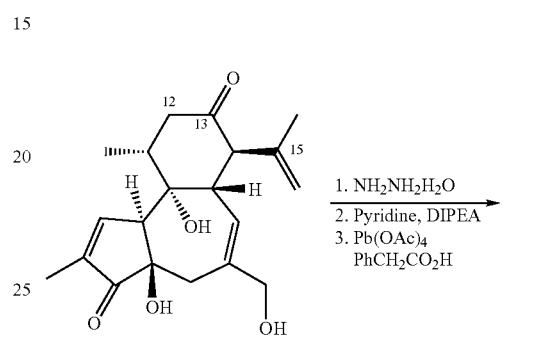

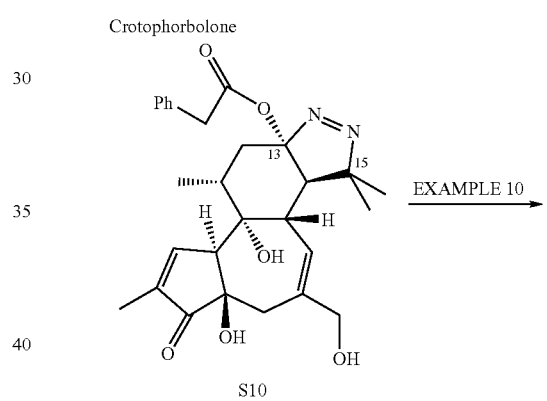

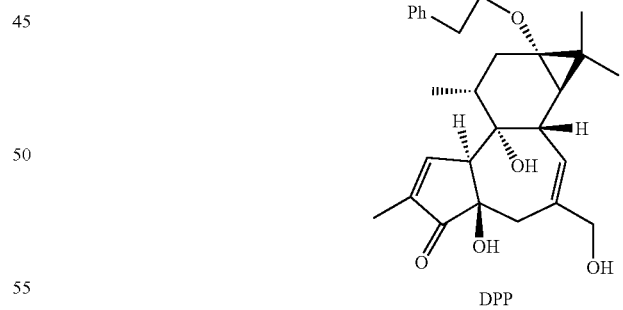

A solution of crotophorbolone (2) (18.8 mg, 54.3 μmol) in methanol (5 mL) was stirred at room temperature under air. Acetic acid (15 μL, 5 equiv.) and hydrazine hydrate (5 μL, 2 equiv.) were added. The reaction was allowed to stir until the consumption of starting material was noted by TLC (100% ethyl acetate), 1 hour. Basic alumina (1 g) and ethyl acetate (10 mL) were added. The slurry was allowed to stir for 10 minutes at ambient temperature. The reaction mixture was passed through a pad of celite (1 g) and concentrated in vacuo. The residue was redissolved in pyridine (2 mL) and DIPEA (200 μL) and transferred to a Teflon-capped resealable pressure tube. The solution was sparged with bubbling argon for 10 minutes and the tube was sealed. The mixture was heated to 160° C. for 48 h. Once the reaction was deemed complete by TLC (30% MeOH in EtOAc), the solvent was removed in vacuo, and the vessel was backfilled with argon to avoid air oxidation of the sensitive pyrazoline. The residue was redissolved in $CH_2Cl_2$ (5 mL) and cooled to 0° C. A pre-mixed solution of $Pb(OAc)_4$ (30 mg, 1.2 equiv.) and phenylacetic acid (370 mg, 50 equiv.) (mixed for 1 h prior to addition) in $CH_2Cl_2$ (5 mL) was added to the pyrazoline at 0° C., and allowed to stir for 30 minutes. The reaction mixture was diluted with ethyl acetate (80 mL) and washed with $NaHCO_3$ (sat.) (3×5 mL), and brine (1×5 mL). The organic layer was dried over $Na_2SO_4$ and concentrated. The residue was subjected to flash chromatography (90% ethyl acetate/pentane) to give diazene S10 as an off white foam (9.3 mg, 35%), and the C13 acetate derivative (1.1 mg, 5%). The analytical data for S10 match those given in EXAMPLE 9.

Example 12

Crotophorbolone to Ether Analogs

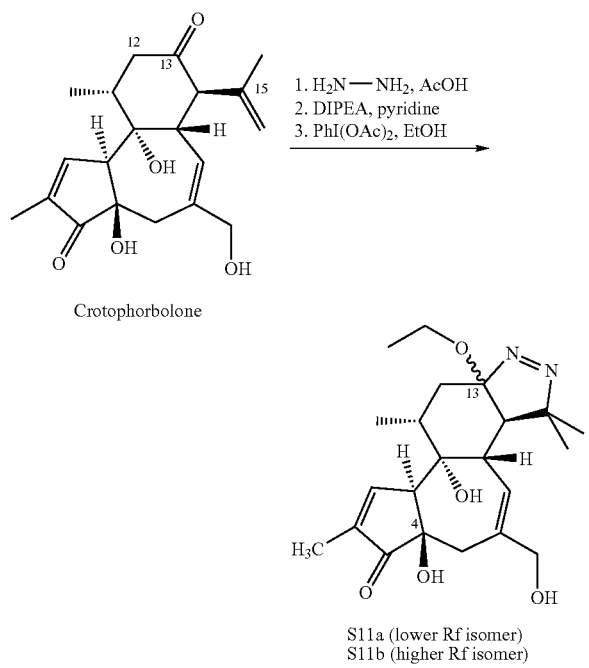

A solution of crotophorbolone (40 mg, 0.115 mmol) was dissolved in methanol (3 mL) under argon atmosphere in a round-bottom flask equipped with a magnetic stir bar. Acetic acid (32 μL, 5 equiv.) and hydrazine hydrate (11 μL, 2 eq) were added dropwise over 5 seconds respectively in this order, and the reaction mixture was stir for 1 h at room temperature. Additional AcOH (10 μL) and hydrazine hydrate (5 μL) were added respectively, and the mixture was stirred for 1 h until TLC indicated complete consumption of the starting material and the formation of a hydrazone (a green spot on the baseline, eluted with 100% EtOAc, stained with p-anisaldehyde). Basic alumina (400 mg) was added, and the heterogeneous mixture was vigorously stirred for 10 minutes. The mixture was filtered through a pad of celite, and the filtrate was concentrated under reduced pressure to give a crude hydrazone. The crude hydrazone was re-suspended in a mixture of pyridine/DIPEA (5 mL, 9:1, v/v) in a Teflon-capped sealed tube under argon and heated to 150° C. for 18 h. After cooling, the solvent was removed under reduced pressure, and the vessel was backfilled with argon. Exposure of the crude pyrazoline to air must be avoided. The crude residue was redissolved in dry ethanol (3 mL), and a pre-mixed solution of $PhI(OAc)_2$ (55 mg, 1.5 equiv.) in ethanol (1 mL, pre-mixed for 30 min at room temperature) was added dropwise over 30 seconds at 0° C. The mixture was stirred at 0° C. for 30 min until TLC indicated complete consumption of the pyrazoline. The reaction was quenched with aqueous $NaHCO_3$ (2 mL) and aqueous $Na_2S_2O_3$ (2 mL), and was extracted with ethyl acetate (3×3 mL). The combined organic layers were washed with brine, and the aqueous phase was back-extracted with ethyl acetate (2×2 mL). The combined organic phases were concentrated under reduced pressure and the residue was purified by silica gel flash chromatography (40→60% ethyl acetate/pentane) to give diazenes S11a (4.2 mg, 9%) and S11b (7.0 mg, 15%) as colorless foams.

Data for S11a (Lower Rf Isomer)

TLC $R_f$=0.43 (100% EtOAc/petroleum ether), one purple spot stained by p-anisaldehyde (visible under UV lamp)

$[α]_D^{23.5}$=+111.5° (c 0.11, MeOH)

$^1$H NMR (500 MHz, $CDCl_3$): δ 7.56 (s, 1H, C1-H), 5.75 (d, 1H, J=6.5 Hz, C7-H), 4.09 (d, 1H, J=13.0 Hz, C20-H), 4.03 (d, 1H, J=13.0 Hz, C20-H), 3.95 (dd, 1H, J=6.3 Hz, 12.4 Hz, C8-H), 3.74 (q, 1H, J=6.6 Hz, $OCH_2CH_3$), 3.07 (s, 1H, C10-H), 2.53-2.62 (m, 4H, 2×C5-H, C11-H, C12-H), 2.04 (s, 1H, OH), 1.84 (brs, 4H, C19-H and OH), 1.79 (d, 1H, J=13.4 Hz, C12-H), 1.70 (d, 1H, J=12.4 Hz, C14-Hz), 1.63 (brs, s, gem-Me and $H_2O$), 1.31 (s, 3H, gem-Me), 1.11 (d, 3H, J=6.7 Hz, C18-H), 1.05 (t, 3H, J=6.9 Hz, $OCH_2CH_3$) ppm.

$^{13}$C NMR (125 MHz, $CDCl_3$): 208.5, 158.3, 142.6, 134.2, 123.8, 110.9, 87.0, 78.4, 73.7, 67.5, 58.6, 58.2, 47.5, 40.1, 38.2, 35.3, 35.0, 29.2, 20.8, 17.6, 16.1, 10.4 ppm.

FT-IR (thin film): ν 3391, 2972, 1699, 1064, 732 $cm^{-1}$.

HRMS: Calcd.: 427.2209 (for [M+Na] $C_{22}H_{32}N_2O_5Na$). Found: 427.2208

Data for S11b (Higher Rf Isomer)

TLC $R_f$=0.50 (100% EtOAc), one purple spot stained by p-anisaldehyde (visible under UV lamp)

$[α]D^{23.5}$=+59.6° (c 0.28, $CH_2Cl_2$)

$^1$H NMR (500 MHz, $CDCl_3$): 7.57 (dd, 1H, J=1.4 Hz, 2.2 Hz, C1-H), 5.53 (d, 1H, J=3.5 Hz, C7-H), 4.06 (d, 1H J=13.9 Hz, C20-H), 4.00 (d, 1H, J=13.9 Hz, C20-H), 3.71 (m, 1H, $OCH_2CH_3$), 3.66 (m, 1H, $OCH_2CH_3$), 3.63 (brs, 1H, OH), 3.25 (dd, 1H, J=4.2 Hz, 11.7 Hz, C8-H), 3.03 (t, 1H, J=2.5 Hz, C10-H), 2.59 (m, 1H, C11-H), 2.52 (d, 1H, J=9.2 Hz, C5-H), 2.36 (d, 1H, J=9.2 Hz, C5-H), 2.19 (brs, 1H, OH), 2.10 (d, 1H, J=13.7 Hz, C12-H), 1.81 (m, 4H, C19-H and C14-H), 1.59 (s, 3H, gem-Me), 1.31 (d, 1H, J=9.8 Hz, C12-H), 1.28 (t, 3H, J=7.0 Hz, $OCH_2CH_3$), 1.20 (d, 3H, J=7.5 Hz, C18-H), 1.19 (s, 3H, gem-Me) ppm.

$^{13}$C NMR (125 MHz, $CDCl_3$): 208.7, 158.1, 140.0, 136.8, 126.9, 120.1, 91.2, 78.8, 73.6, 68.6, 59.7, 56.0, 46.5, 40.2, 39.1, 35.2, 31.7, 29.4, 22.0, 18.7, 15.6, 10.5 ppm.

FT-IR (thin film): ν 3404, 2973, 1705, 1061, 889, 737 $cm^{-1}$.

HRMS: Calcd.: 427.2209 (for [M+Na] $C_{22}H_{32}N_2O_5Na$). Found: 427.2204

Example 13

Formation of Cyclopropane Ring Structure

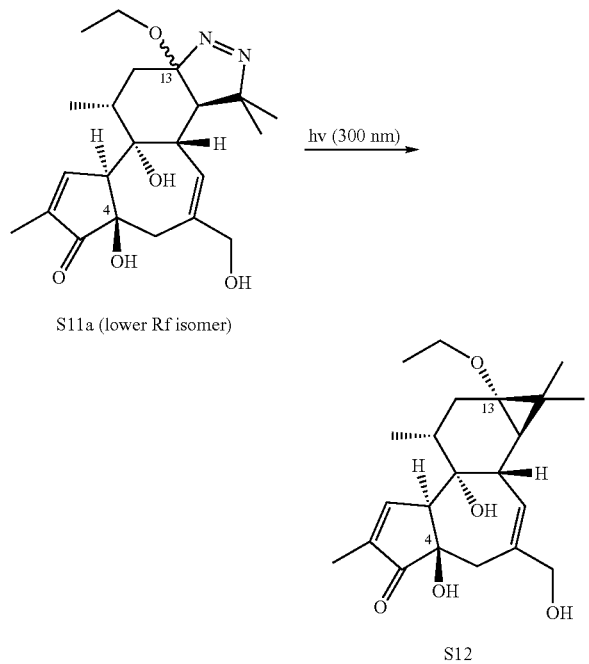

A solution of diazene S11a (1.2 mg, 2.9 μmol) in EtOAc (1 mL) was stirred at room temperature in a disposable glass vial and flushed with argon. The solution was irradiated with UV light (300 nm) using a Rayonet photochemical reactor at room temperature for 30 min until TLC indicated complete consumption of the starting material. The reaction mixture was concentrated under reduced pressure, and subjected to flash chromatography (100% EtOAc, ID 8 mm, ~1 g silica) to give 12-deoxy-13-ethoxyphorbol (S12) as a white powder (1.0 mg, 90%). The analytical data for the product are identical with those of the product obtained by photolysis of diazene S11b.

Example 14

Formation of Cyclopropane Ring Structure

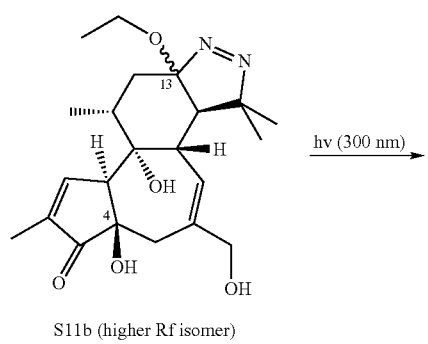

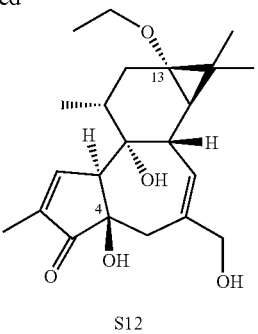

A solution of diazene S11b (3.0 mg, 7.4 μmol) in EtOAc (1 mL) was stirred at room temperature in a disposable glass vial and flushed with argon. The solution was irradiated with UV light (300 nm) using a Rayonet photochemical reactor at room temperature for 30 min until TLC indicated complete consumption of the starting material. The reaction mixture was concentrated under reduced pressure, and subjected to flash chromatography (100% EtOAc, ID 8 mm, ~1 g silica) to give 12-deoxy-13-ethoxyphorbol (S12) as a white powder (2.0 mg, 72%).

TLC $R_f$=0.60 (100% Ethyl acetate), one bluish grey spot stained by p-anisaldehyde (visible under UV lamp)

$[\alpha]D^{23.5}$=+52.2° (c 0.10, $CH_2Cl_2$)

$^1$H NMR (500 MHz, $CDCl_3$): δ 7.57 (s, 1H, C1-H), 5.66 (d, 1H, J=4.8 Hz, C7-H), 4.06 (dd, 1H, J=6.4 Hz, 12.6 Hz, C20-H), 4.01 (dd, 1H, J=6.4 Hz, 12.6 Hz, C20-H), 3.66 (dt, 1H, J=7.0 Hz, 15.8 Hz, $OCH_2CH_3$), 3.44 (dt, 1H, J=7.1 Hz, 15.6 Hz, $OCH_2CH_3$), 3.19 (brs, 1H, C10-H), 2.84 (t, 1H, J=5.2 Hz, C8-H), 2.54 (d, 1H, J=19.2 Hz, C5-H), 2.44 (d, 1H, J=19.1 Hz, C5-H), 2.20 (s, 1H, OH), 2.12 (s, 1H, OH), 2.03 (m, 1H, C11-H), 1.92 (dd, 1H, J=7.3 Hz, 14.8 Hz, C12-H), 1.82 (brs, 3H, C19-H), 1.69 (dd, 1H, J=8.8 Hz, 14.9 Hz, C12-H), 1.55 (t, 1H, J=6.0 Hz, C20-OH), 1.30 (s, 3H, gem-Me), 1.19 (t, 3H, J=7.1 Hz, $OCH_2CH_3$), 1.03 (s, 3H, gem-Me), 0.99 (d, 3H, J=6.6 Hz, C18-H), 0.76 (d, 1H, J=6.8 Hz, C14-H) ppm.

$^{13}$C NMR (125 MHz, $CDCl_3$): δ 209.2, 160.4, 139.7, 134.4, 130.4, 74.0, 68.7, 64.9, 62.7, 56.2, 39.1, 39.0, 36.6, 32.7, 31.1, 25.7, 22.5, 19.3, 16.9, 15.9, 10.5 ppm.

FT-IR (thin film): ν 3390, 2917, 1698, 1075, 908, 732 $cm^{-1}$.

HRMS: Calcd.: 399.2147 (for [M+Na] $C_{22}H_{32}O_5Na$). Found: 399.2148

Example 15

Crotophorbolone to Ether Analog

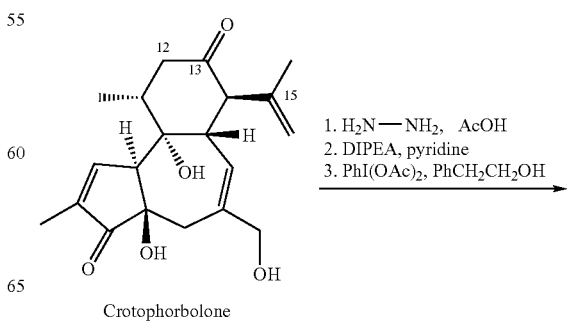

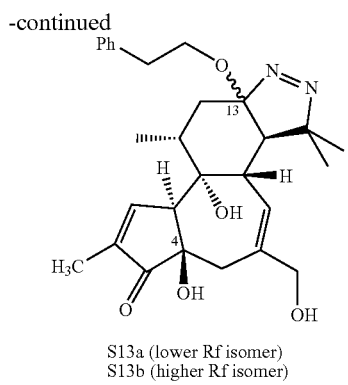

S13a (lower Rf isomer)
S13b (higher Rf isomer)

A solution of crotophorbolone (27.1 mg, 84 μmol) in methanol (5 mL) was stirred at room temperature under air. Acetic acid (23 μL, 5 equiv.) and hydrazine hydrate (8 μL, 2 equiv.) were added. The reaction was allowed to stir for 1 h until the consumption of starting material was noted by TLC (100% ethyl acetate). Basic alumina (1 g) and ethyl acetate (10 mL) were added. The slurry was allowed to stir for 10 minutes at ambient temperature. The crude was passed through a pad of celite (1 g) and concentrated in vacuo. The crude was redissolved in pyridine (1.80 mL) and DIPEA (0.20 mL) and transferred to a Teflon-capped resealable pressure tube. The solution was sparged with bubbling argon for 10 minutes and the tube was sealed. The mixture was heated to 150° C. for 16 h. Once the reaction was deemed complete by TLC (30% MeOH in EtOAc), the solvent was removed in vacuo, and the vessel was backfilled with argon to avoid air oxidation of the sensitive pyrazoline. The crude was redissolved in phenethyl alcohol (5 mL) and cooled to 0° C. In a separate flask, phenethyl alcohol (5 mL) and PhI(OAc)$_2$ (125 mg, 5 equiv.) were combined, and allowed to stir. The mixture was briefly warmed to 40° C. to aid in dissolution. The light yellow clear solution was cooled to 0° C. and added into the pyrazoline solution at 0° C. The reaction was allowed to stir for 1 h at 0° C. and 3 h at ambient temperature. A mixture of saturated aqueous NaHCO$_3$ and saturated aqueous Na$_2$S$_2$O$_3$ (5 mL, 1:1) were added. The organic layer was extracted with ethyl acetate (3×20 mL), dried over Na$_2$SO$_4$ and concentrated. The phenethyl alcohol was then distilled away from the product (150 mmHg, 70° C.), and the residue was subjected to flash chromatography. (1:1 EtOAc/Et$_2$O) to give two diastereomeric diazenes as hard off white foams (S13a—4.6 mg, 12%) and (S13b—2.3 mg, 6%).

Data for S13a (Lower Rf Isomer)

TLC R$_f$=0.60 (100% EtOAc), one black spot in p-anisaldehyde (visible under UV lamp);

$[\alpha]_D^{23.5}$=+88.1° (c 0.22, CH$_2$Cl$_2$)

$^1$H NMR (500 MHz, CDCl$_3$): δ7.47 (s, 1H, C1-H), 7.18-7.25 (m, 3H, Ar—H), 7.12 (d, 2H, 7.1 Hz, Ar—H), 5.67 (d, J=6.7 Hz, 1H, C7-H), 4.05 (dd, J=15.0, 22.8 Hz, 1H, C20-H), 3.96-4.01 (m, 2H, C20-H and OCH$_2$CH$_2$Ph), 3.86 (dd, J=8.1 Hz, 14.5 Hz, 1H, OCH$_2$CH$_2$Ph), 3.70 (dd, J=7.0, 12.1 Hz, 1H, C8-H), 2.95 (br s, 1H, C10-H), 2.65-2.76 (m, 2H, OCH$_2$CH$_2$Ph), 2.50 (d, J=18.5 Hz, C5-H), 2.48 (dd, J=3.9 Hz, 13.3 Hz, 1H, C12-H), 2.37-2.42 (m, 1H, C11-H), 2.38 (d, 1H, J=18 Hz, C5-H), 1.79 (m, 3H, C19-H), 1.75 (t, 1H, J=12.8 Hz, C12-H), 1.66 (d, 1H, J=12.4 Hz, C14-H), 1.64 (s, 1H, OH), 1.59 (s, 3H, gem-Me), 1.55 (t, J=5.7 Hz, C20-OH), 1.28 (s, 1H, OH), 1.19 (s, 3H, gem-Me), 1.03 (d, 3H, J=6.8 Hz, C18-H) ppm.

$^{13}$C NMR (125 MHz, CDCl$_3$): δ208.1, 157.8, 142.7, 139.2, 134.0, 129.2, 128.2, 125.9, 110.8, 87.0, 78.0, 73.3, 67.2, 63.8, 57.9, 47.3, 40.0, 37.7, 36.9, 35.2, 34.7, 30.3, 29.1, 20.5, 17.4, 10.3 ppm.

FT-IR (thin film): ν 3402, 2926, 1703 (br), 1453, 1257, 1066 cm$^{-1}$.

HRMS: Calcd. (for C$_{28}$H$_{36}$N$_2$O$_5$Na): 503.2522. Found: 503.2516

Data for S13b (Higher Rf Isomer)

TLC R$_f$=0.67 (100% EtOAc), one black spot in p-anisaldehyde (visible under UV lamp);

$[\alpha]_D^{23.5}$=+34.4° (c 0.10, CHCl$_3$)

$^1$H NMR (500 MHz, CDCl$_3$): δ7.51 (br s, 1H), 7.32-7.21 (m, 5H), 5.51 (s, 1H, C7-H), 4.08 (dd, J=4, 16 Hz, 1H), 4.01 (dd, J=4, 16 Hz, 1H), 3.96 (dd, J=7, 16 Hz, 1H), 3.76 (dd, J=7, 16 Hz, 1H), 3.23 (s, 1H), 3.21 (br s, 1H), 3.01-2.96 (m, 3H, CH$_2$Ph), 2.59-2.48 (m, 2H), 2.35 (d, J=19.5 Hz, 1H), 2.07 (d, J=8 Hz, 1H), 2.06 (d, J=8 Hz, 1H) 1.82 (s, 3H), 1.80 (s, 1H), 1.42 (dd, J=7, 7 Hz, 1H), 1.30-1.26 (m, 1H), 1.19 (s, 3H), 1.06 (d, J=7 Hz, 3H)

$^{13}$C NMR (125 MHz, CDCl$_3$): δ 208.7, 157.9, 139.8, 137.9, 136.6, 128.9 (2), 128.5 (2), 126.7, 126.5, 120.0, 91.3, 78.5, 73.5, 68.4, 64.9, 55.9, 46.2, 40.0, 39.0, 36.6, 35.0, 31.4, 29.4, 21.9, 18.3, 10.3 ppm.

FT-IR (thin film): ν 3400 (br), 2916, 1704, 1457, 1374, 1237, 1063 cm$^{-1}$.

HRMS: Calcd. for (C$_{28}$H$_{36}$N$_2$O$_5$+Na): 503.2622. Found 503.2516

Example 16

Formation of Cyclopropane Ring Structure

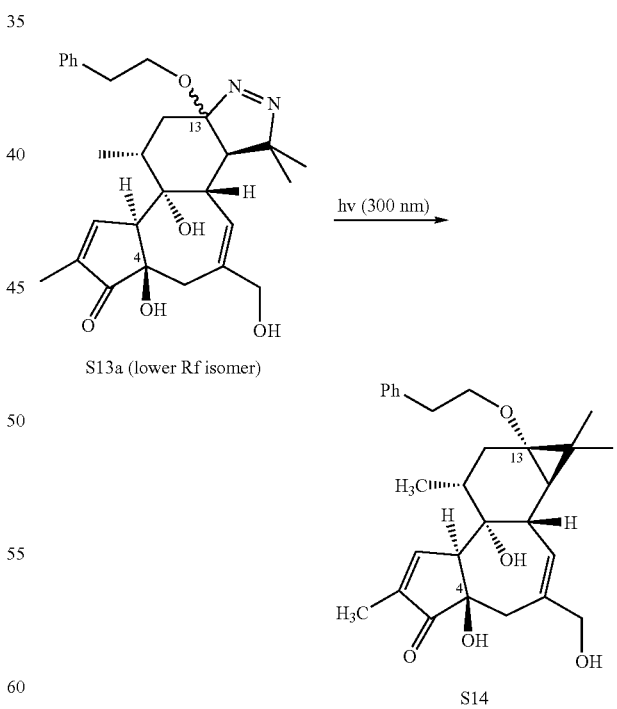

A solution of S13a (1.5 mg, 3.2 μmol) in EtOAc (1.0 mL) was stirred at room temperature in a disposable glass vial and flushed with argon. The solution was irradiated with UV light (300 nm) using a Rayonet photochemical reactor at room temperature for 30 min until TLC indicated complete consumption of the starting material. The reaction mixture was concentrated under reduced pressure, and subjected to flash chromatography (50% ethyl acetate/pentane, ID 8 mm, ~1 g silica) to give 12-deoxyphorbol-13-phenethyl ether (S14) as a white powder (1.2 mg, 81%). The product is identical with the photolysis product of S13b.

FT-IR (thin film): ν 3400 (br), 2916, 1702, 1452, 1077 cm$^{-1}$.

HRMS: Calcd. (for $C_{28}H_{36}O_5$+Na): 475.2460. Found: 475.2456.

Example 17

Formation of Cyclopropane Ring Structure

Example 18

Conversion of Tiglianes to Daphnanes

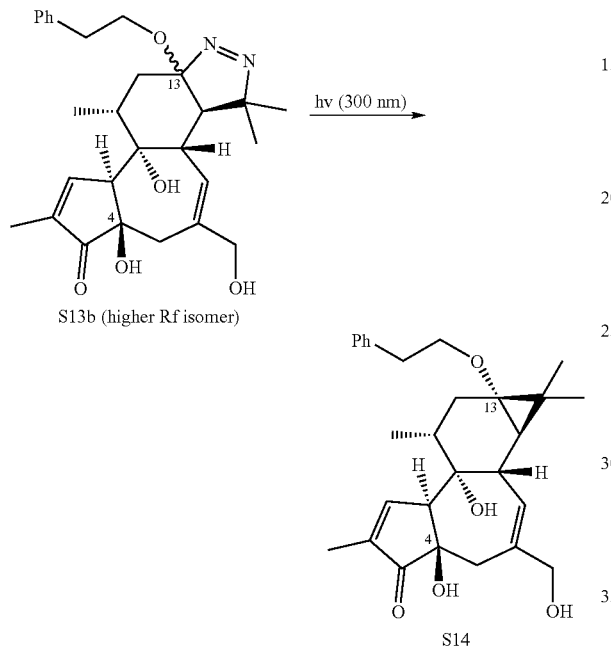

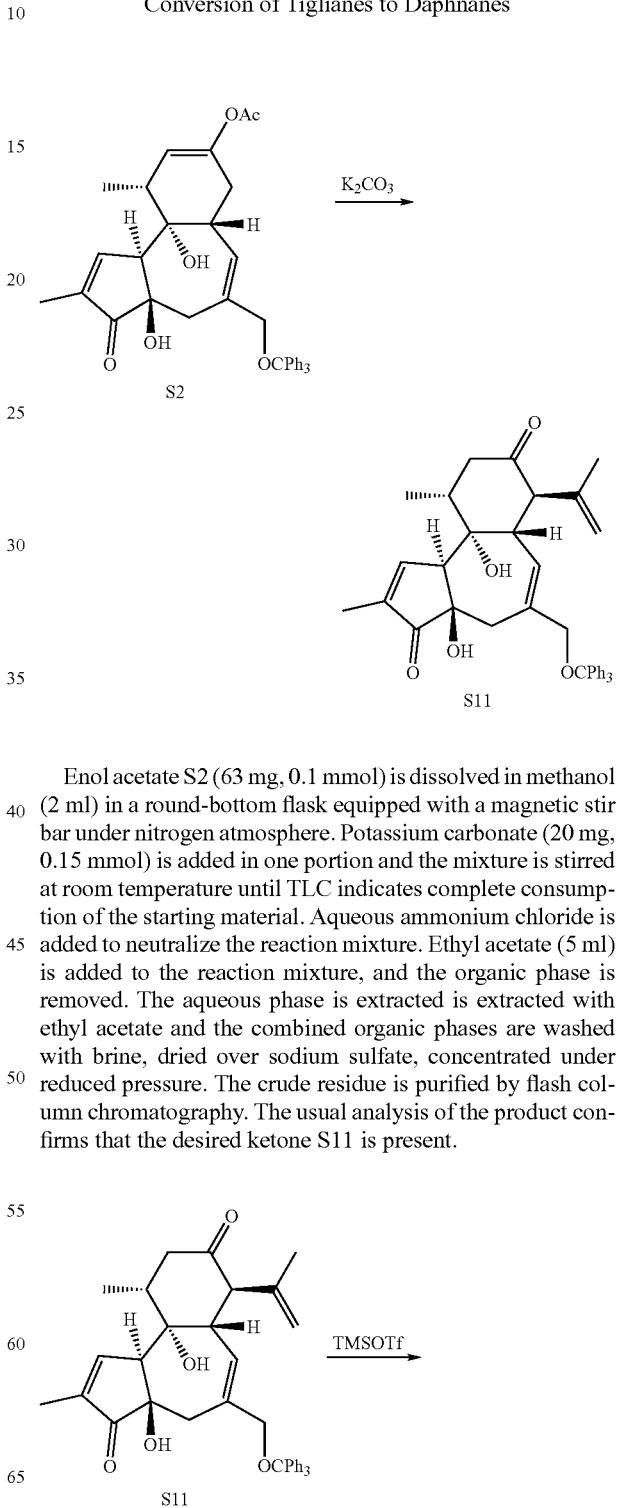

A solution of S13b (17 mg, 34 μmol) in EtOAc (7.6 mL) was stirred at room temperature in a disposable glass vial and flushed with argon. The solution was irradiated with UV light (300 nm) using a Rayonet photochemical reactor at room temperature for 45 min until TLC indicated complete consumption of the starting material. The reaction mixture was concentrated under reduced pressure, and subjected to flash chromatography (50% Et$_2$O:EtOAc, ID 8 mm, ~1 g silica) to give 12-deoxyphorbol-13-phenethyl ether (S14) as a white powder (14 mg, 87%). The product was characterized by:

TLC R$_f$=0.70 (100% EtOAc), one dark blue spot in p-anisaldehyde (visible under UV lamp);

[α]D$^{23.5}$+52.0° (c 0.12, CHCl$_3$)

$^1$H NMR (500 MHz, CDCl$_3$): δ 7.53 (brs, 1H, C1-H), 7.31-1.19 (m, 5H, Ar—H), 5.61 (d, 1H, J=3.8 Hz, C7-H), 4.04 (d, 1H, J=13.1 Hz, C20-H), 3.98 (d, 1H, J=13.1 Hz, C20-H), 3.74 (ddd, 1H, J=7.3, 7.3, 8.6 Hz, OCH$_2$CH$_2$Ph), 3.50 (ddd, 1H, J=7.3, 7.3, 8.6 Hz, OCH$_2$CH$_2$Ph), 3.15 (brs, 1H, C10-H), 2.84 (d, 1H, J=7.3 Hz, OCH$_2$CH$_2$Ph), 2.83 (d, 1H, J=7.3 Hz, OCH$_2$CH$_2$Ph), 2.78 (m, 1H, C8-H), 2.51 (d, 1H, J=19 Hz, C5-H), 2.41 (d, 1H, J=19 Hz, C5-H), 1.96 (q, 1H, J=7.5 Hz, C11-H), 1.86 (dd, 1H, J=7.5, 15 Hz, C12-H), 1.79 (d, 3H, J=1.4 Hz, C19-H), 1.58 (dd, 1H, J=9.0 Hz, 15.0 Hz, C12-H), 1.21 (s, 3H, gem-Me), 1.20-1.16 (m, 1H), 0.99 (s, 3H, gem-Me), 0.89 (d, 3H, J=6.7 Hz, C18-H), 0.72 (d, 1H, J=6.8 Hz, C14-H)

$^{13}$C NMR (125 MHz, CDCl$_3$): δ 208.8, 160.1, 139.4, 138.9, 134.1, 130.0, 129.0 (2), 128.3 (2), 126.2, 77.5, 73.7, 68.5, 68.2, 64.7, 56.0, 38.8, 38.7, 36.8, 36.3, 32.4, 30.8, 25.5, 22.2, 18.9, 16.6, 10.2 ppm.

Enol acetate S2 (63 mg, 0.1 mmol) is dissolved in methanol (2 ml) in a round-bottom flask equipped with a magnetic stir bar under nitrogen atmosphere. Potassium carbonate (20 mg, 0.15 mmol) is added in one portion and the mixture is stirred at room temperature until TLC indicates complete consumption of the starting material. Aqueous ammonium chloride is added to neutralize the reaction mixture. Ethyl acetate (5 ml) is added to the reaction mixture, and the organic phase is removed. The aqueous phase is extracted is extracted with ethyl acetate and the combined organic phases are washed with brine, dried over sodium sulfate, concentrated under reduced pressure. The crude residue is purified by flash column chromatography. The usual analysis of the product confirms that the desired ketone S11 is present.

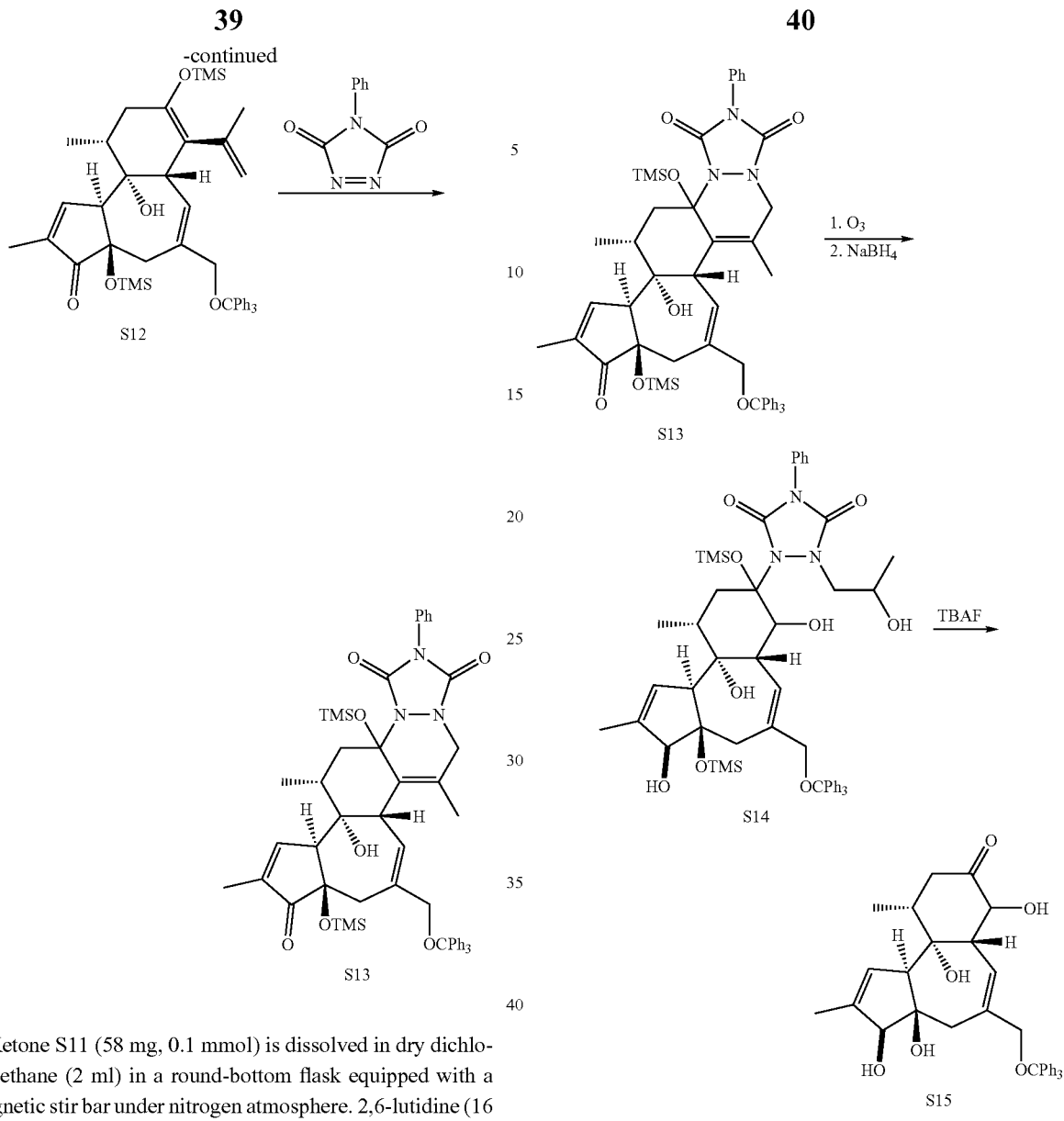

Ketone S11 (58 mg, 0.1 mmol) is dissolved in dry dichloromethane (2 ml) in a round-bottom flask equipped with a magnetic stir bar under nitrogen atmosphere. 2,6-lutidine (16 mg, 1.5 eq.) is added via a syringe dropwise at room temperature and the reaction mixture is cooled to 0° C. Trimethylsilyl trifluorosulfonate (2.5 µl, 1.1 eq.) is added via a syringe dropwise and the reaction mixture is stirred at 0° C. until TLC indicates complete consumption of S11.

The reaction mixture is cooled to −78° C. and then 4-phenyl-1,2,4-triazoline-3,5-dione (PTAD) (20 mg, 1.1 eq) in dichloromethane is added via a syringe dropwise. The reaction mixture is stirred at −78° C. until TLC indicates complete consumption of the starting material. Aqueous sodium bicarbonate is added to the reaction mixture and warmed up to room temperature. The organic phase is removed and the aqueous phase is extracted with dichloromethane. The combined organic phases are washed with brine, dried over sodium sulfate, and concentrated under reduced pressure. The crude residue is purified by flash column chromatography. The usual analysis of the product confirms that the desired product S13 is present.

Substrate S13 (90 mg, 0.1 mmol) is dissolved in a mixture (5 ml) of dry dichloromethane and methanol (1:10 mixture, v/v) in a round-bottom flask equipped with a magnetic stir bar. The solution was cooled to −78° C. in a dry ice/acetone bath and ozone is bubbled through the solution until a light blue color appeared. The residual ozone is removed from the reaction mixture by bubbling nitrogen through the solution until the blue color disappears. Sodium borohydride (4 mg, 1.1 eq) is added to the reaction mixture and the reaction mixture is warmed to 0° C. by replacing the cooling bath with an ice/water bath. The reaction mixture is stirred until TLC indicates complete conversion to the product. The reaction is quenched by addition of aqueous ammonium chloride and the organic phase is removed. The aqueous phase is extracted with ethyl acetate and the combined organic phase is washed with brine, dried over sodium sulfate (s) and concentrated under reduced pressure. Purification by flash chromatography provides the desired product S14. The usual analysis of the product confirms that the desired product S14 is present.

Compound S14 (95 mg, 0.1 mmol) is dissolved in dry THF (5 ml) in a round-bottom flask equipped with a magnetic stir bar under inert atmosphere and cooled to 0° C. Tetrabutylammonium fluoride solution in THF (0.11 ml, 1.0 M solution) is added dropwise via a syringe to the reaction mixture, and the mixture is stirred at 0° C. until TLC indicates complete consumption of the starting material S14. The reaction is diluted with ether and quenched by addition of aqueous ammonium chloride solution. The separated aqueous phase is extracted with ethyl acetate. The combined organic phase is washed with brine, dried over sodium sulfate (s), and concentrated under reduced pressure. The crude material is purified by flash column chromatography. The usual analysis of the product confirms that the desired product S15 is present.

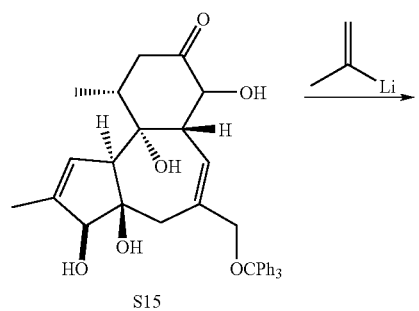

Ketone S15 (57 mg, 0.1 mmol) is dissolved in dry THF (2 ml) in a round-bottom flask equipped with a magnetic stir bar under inert atmosphere and cooled down to 78° C. Isopropenyllithium solution (0.5 ml, 1.0 M solution) (in dry THF) is added via a syringe dropwise and the mixture is stirred at −78° C. until TLC indicates complete consumption of S15. The reaction is diluted with diethyl ether (5 ml), quenched by addition of aqueous ammonium chloride solution, and warmed to room temperature. The organic phase is separated and the aqueous phase is extracted with ethyl acetate. The combined organic phases are washed with brine, dried over sodium sulfate, filtered, and concentrated under reduced pressure. The crude material is purified by flash column chromatography. The usual analysis of the product confirms that the desired product S16, a daphnane, is present.

Example 19

Route to C14-Oxy Tiglianes

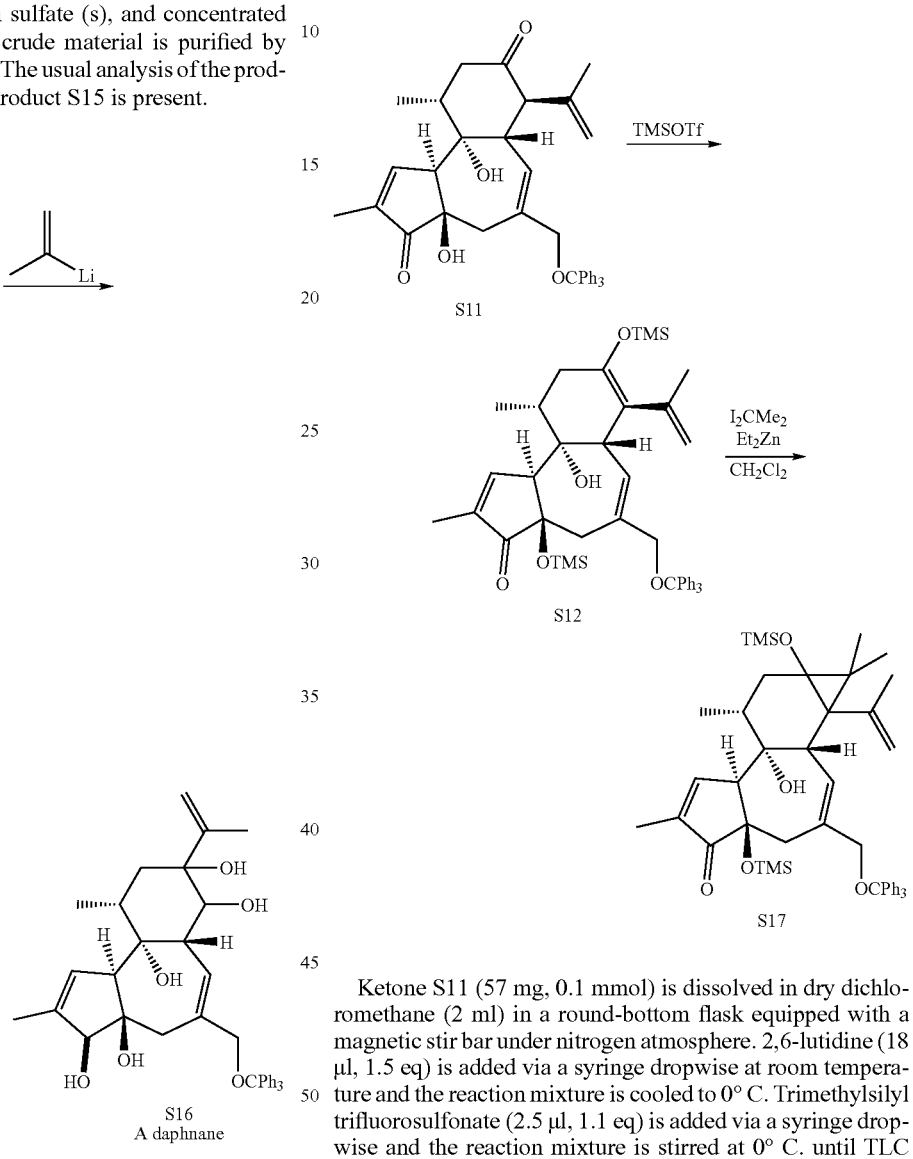

Ketone S11 (57 mg, 0.1 mmol) is dissolved in dry dichloromethane (2 ml) in a round-bottom flask equipped with a magnetic stir bar under nitrogen atmosphere. 2,6-lutidine (18 μl, 1.5 eq) is added via a syringe dropwise at room temperature and the reaction mixture is cooled to 0° C. Trimethylsilyl trifluorosulfonate (2.5 μl, 1.1 eq) is added via a syringe dropwise and the reaction mixture is stirred at 0° C. until TLC indicates complete consumption of S11. Aqueous ammonium chloride is added to neutralize the reaction mixture, and the organic phase is separated. The aqueous phase is extracted is extracted with dichloromethane and the combined organic phases are washed with brine, dried over sodium sulfate, concentrated under reduced pressure.

The crude residue is dissolved in dry dichloromethane (5 ml) in a round-bottom flask equipped with a magnetic stir bar under nitrogen atmosphere at −10° C. Diethylzinc (0.21 ml, 1.0M solution in THF) is added via a syringe and then diiodopropane (29 mg, 0.1-mmol) is added via a syringe dropwise. The reaction mixture is stirred at room temperature until TLC indicates complete consumption of the starting material. The reaction mixture is diluted with diethyl ether and aqueous HCl is added. The organic phase is removed and the aqueous phase is extracted with ether. The combined organic phases are washed with brine, dried over sodium sulfate, and concentrated under reduced pressure. The crude product is purified by silica gel flash chromatography. The usual analysis of the product confirms that the desired product S17 is present.

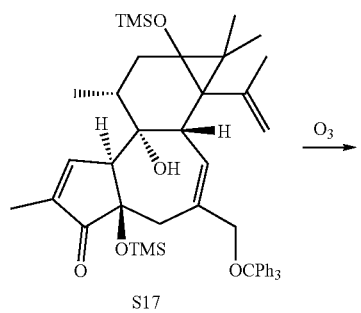
S17

Olefin S17 (77 mg, 0.1 mmol) is dissolved in a mixture (5 ml) of dichloromethane and methanol (1:10, v/v) in a round-bottom flask equipped with a magnetic stir bar and cooled to −78° C. Ozone is bubbled through the reaction mixture until light blue color appears. Repeat bubbling ozone until TLC indicates complete consumption of S17. The residual ozone is removed by bubbling nitrogen through the reaction mixture. The reaction is quenched by addition of excess thiourea and stirred at −78° C. for 30 min and subsequently warmed to room temperature. The residual thiourea is removed by filtration and the filtrated is concentrated under reduced pressure. The crude material is purified by flash column chromatography. The usual analysis of the product confirms that the desired product S18 is present.

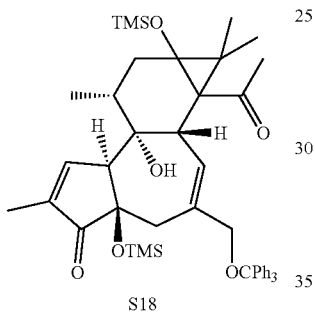
S18

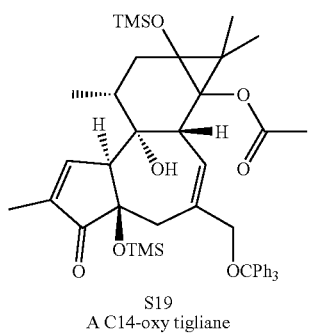
S19
A C14-oxy tigliane

Ketone S18 (78 mg, 0.1 mmol) is dissolved in dry dichloromethane (5 ml) in a round-bottom flask equipped with a magnetic stir bar under inert atmosphere at 0° C. One equivalent of m-chloroperbenzoic acid (m-CPBA) (0.105 mmol) is added in one portion and the reaction mixture is stirred at 0° C. until TLC indicates complete consumption of S18. The reaction is quenched by addition of aqueous sodium thiosulfate and the organic phase is removed. The aqueous phase is extracted with dichloromethane and the combined organic phases are washed with brine, dried over sodium sulfate (s), filtered, and concentrated under reduced pressure. The crude residue is purified by flash column chromatography, and the usual analysis of the product confirms that the desired product S19, a C14-oxy tigliane, is present.

Example 20

Production of Daphnanes

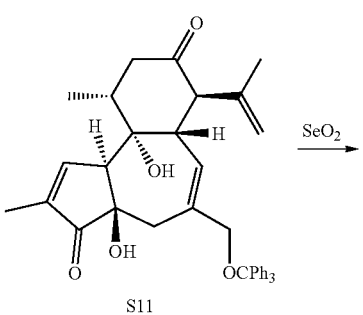
S11

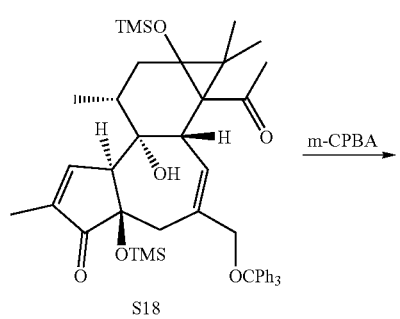
S18

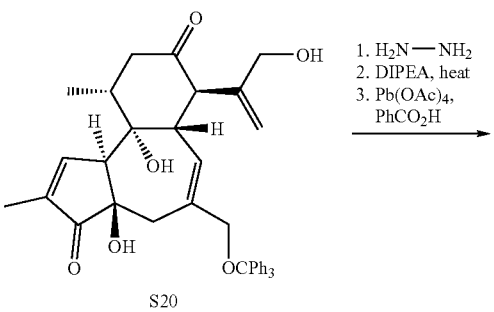
S20

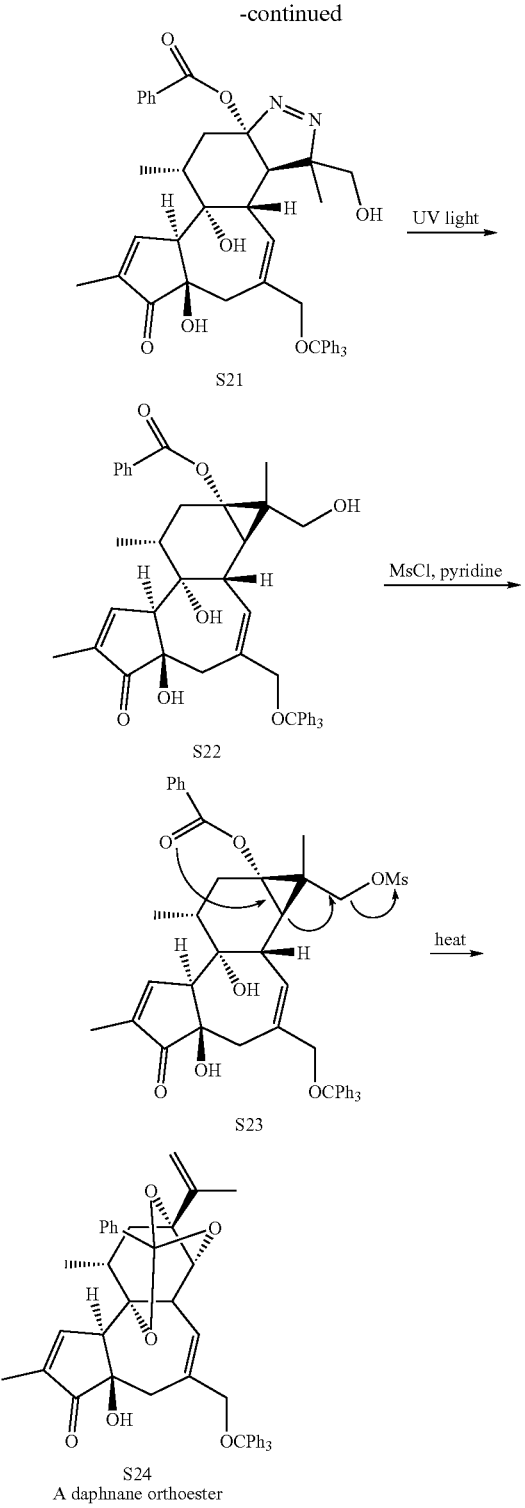

S21

S22

S23

S24
A daphnane orthoester

Ketone S11 (57 mg, 0.1 mmol) is dissolved in dry toluene (2 ml) in a round-bottom flask equipped with a magnetic stir bar. Selenium dioxide (22 mg, 2.0 eq) is added in one portion and the mixture is stirred at 80° C. until TLC indicates complete consumption of S11. The reaction mixture is filtered to remove residual selenium reagent. The filtrate is washed with aqueous sodium thiosulfate, dried over sodium sulfate (s), and concentrated under reduced pressure. The crude material is purified by flash column chromatography, and the usual analysis of the product confirms that the desired product S20 is present.

Alcohol S20 (59 mg, 0.1 mmol) is dissolved in dry ethanol (2 ml) in a round-bottom flask equipped with a magnetic stir bar under argon atmosphere. Hydrazine hydrate (0.15 mmol) and acetic acid (0.4 mmol) are added dropwise via a syringe respectively. The reaction mixture is stirred at room temperature until TLC indicates complete consumption of S20. Basic alumina is added to neutralize the acid, and the mixture is stirred for 10 min at room temperature. The mixture is filtered and the filtrate is concentrated under reduced pressure. The crude material is redissolved in a mixture of dry toluene and diisopropylethylamine (3 ml, 9:1, v/v), degassed by freeze-pump-thaw, and flushed with argon. The mixture is heated in a sealed vessel to 150° C. until TLC indicates complete consumption of the starting material. The crude product is concentrated by evaporating the solvent under argon atmosphere to avoid decomposition by reacting with oxygen. The volatiles are evaporated under argon atmosphere and the crude residue is re-dissolved in dry dichloromethane at 0° C. A mixture of lead (IV) acetate (0.12 mmol) and excess benzoic acid in dichloromethane (pre-mixed under inert atmosphere) is added dropwise and the reaction mixture is stirred at 0° C. until TLC indicates complete consumption of the starting material. The reaction is quenched by addition of aqueous sodium bicarbonate solution and the organic phase is separated. The aqueous phase is extracted with dichloromethane and the combined organic phases are washed with brine, dried over sodium sulfate (s), and concentrated under reduced pressure. The crude material is purified by flash column chromatography, and the usual analysis confirms that the desired pyrazoline S21 is present.

Pyrazoline S21 (74 mg, 0.1 mmol) is dissolved in dry benzene (2 ml) in a round-bottom flask under argon atmosphere. The mixture is irradiated with UV light (300 or 350 nm) until TLC indicates complete consumption of S21. The solvent is evaporated under reduced pressure and the crude residue is purified by flash column chromatography. The usual analysis confirms that the desired cyclopropane S22 is present.

S22 (71 mg, 0.1 mmol) is dissolved in dry dichloromethane (5 ml) in a round bottom flask equipped with a magnetic stir bar under argon atmosphere. Pyridine is added and the mixture is cooled to 0° C. Methanesulfonyl chloride (0.11 mmol) is added dropwise via a syringe and the mixture is stirred at 0° C. until TLC indicates complete consumption of S22. The reaction is quenched with aqueous ammonium chloride and the organic phase is separated. The aqueous phase is extracted with dichloromethane, and the combined organic phases are washed with brine, dried over sodium sulfate (s) and concentrated under reduced pressure. The crude residue S23 is used in the next step without further purification.

Crude S23 is dissolved in dry 2,4,6-trimethylpyridine (5 ml) in a round-bottom flask equipped with a magnetic stir bar. Molecular sieves (100 mg) are added and the suspension is refluxed under argon atmosphere until TLC indicates complete consumption of S23. The reaction mixture is cooled to room temperature and diluted with diethyl ether. The mixture is washed with aqueous ammonium chloride and 1 N hydrochloric acid solution to remove residual 2,4,6-trimethylpyridine, dried over sodium sulfate, filtered, and concentrated under reduced pressure. The crude residue is purified by flash column chromatography, and the usual analysis confirms that the desired orthoester S24 is present.

Example 21

Production of C13-Alkoxy Pyrazoline

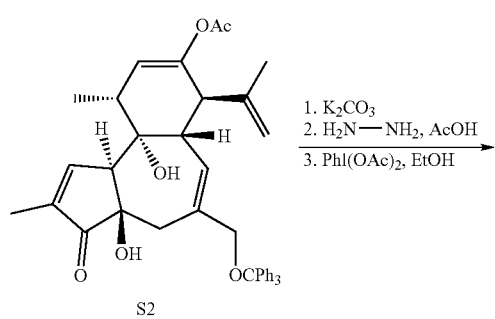

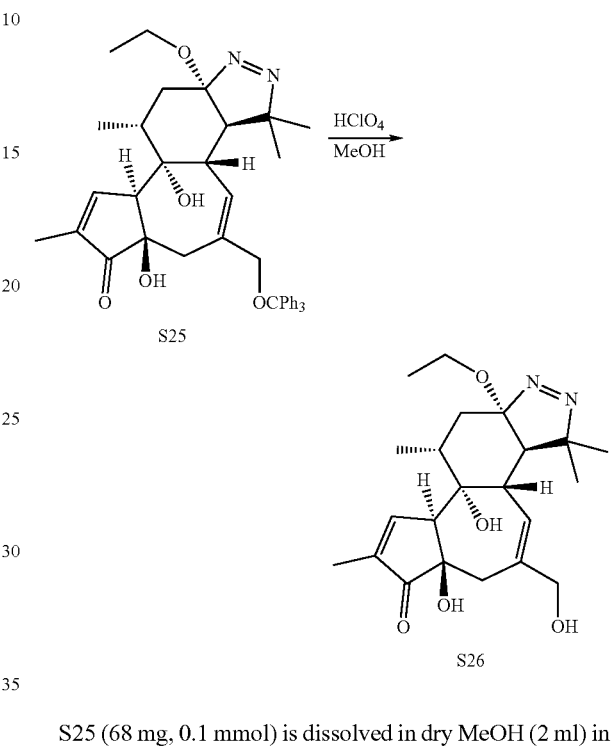

Enol acetate S2 (63 mg, 0.1 mmol) is dissolved in dry methanol (2 ml) in a round bottom flask equipped with a magnetic stir bar under air at room temperature. $K_2CO_3$ (1.5 eq.) is added in a single portion, and the mixture is stirred vigorously until complete conversion to ketone is observed by TLC. Acetic acid (5 eq) and hydrazine hydrate (5 eq.) are added, and the reaction is allowed to stir for 1 hour and monitored by TLC (100% ethyl acetate, PA Stain). Following complete consumption of the starting material, basic alumina is added, and the reaction is diluted with ethyl acetate. The mixture is passed through a pad of CELITE® with ethyl acetate rinse. The organic solvent is removed under reduced pressure to give the crude hydrazone. The crude hydrazone is resuspended in a mixture of toluene/DIPEA (3 ml, 9:1, v/v) in a Teflon-capped sealed tube under argon. The mixture is heated to 150° C. for 16 hours. After cooling, the solvent was removed under reduced pressure, and the vessel backfilled with argon. Exposure of the crude pyrazoline S5 to air must be avoided. The crude is redissolved in ethanol (3 ml), and a pre-mixed solution of $PhI(OAc)_2$ (1.5 eq.) in ethanol (pre-mixed for 10 min at ambient temperature) is added at 0° C. The mixture is stirred at 0° C. until TLC indicates complete consumption of the pyrazoline S5. The reaction is quenched with aqueous $NaHCO_3$ (saturated), and extracted with diethyl ether. The combined organic layers are washed with brine, dried over $Na_2SO_4$, filtered to remove drying agent, and concentrated under reduced pressure. The residue is purified by flash chromatography. The usual analysis of the product confirms that the desired product S25 is present.

Example 22

Removal of Trityl Protecting Group

S25 (68 mg, 0.1 mmol) is dissolved in dry MeOH (2 ml) in a round bottom flask equipped with a magnetic stir bar at room temperature, and $HClO_4$ (20 µl, 70% in $H_2O$) is added. The reaction is allowed to stir at ambient temperature until TLC indicates complete consumption of S25. The mixture is neutralized by addition of solid $NaHCO_3$, diluted with EtOAc and filtered through a pad of CELITE®. The crude filtrate is concentrated under reduced pressure, and subjected to flash chromatography to provide the product S26. The usual analysis of the product confirms that the desired product is present.

Example 23

Formation of Cyclopropane Ring Structure

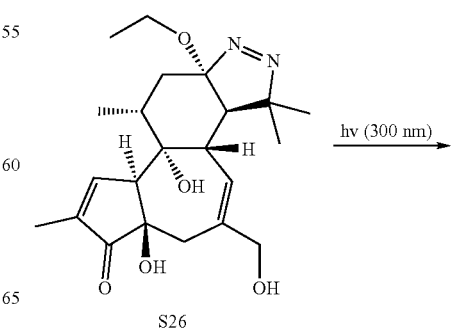

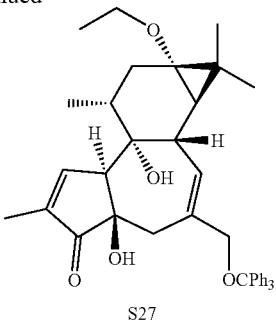

S10 (43 mg, 0.1 mmol) is dissolved in a mixture of benzene and ethyl acetate (2 ml, 1:1, v/v) in a round-bottom flask at room temperature under argon atmosphere. The solution is irradiated with UV light (300 nm) using a Rayonet photochemical reactor at room temperature until TLC indicates complete consumption of the starting material. The reaction mixture is concentrated under reduced pressure, and the crude residue is purified by flash column chromatography. The usual analysis confirms that the desired product S27 is present.

Example 24

Production of C13-Bromo Pyrazoline

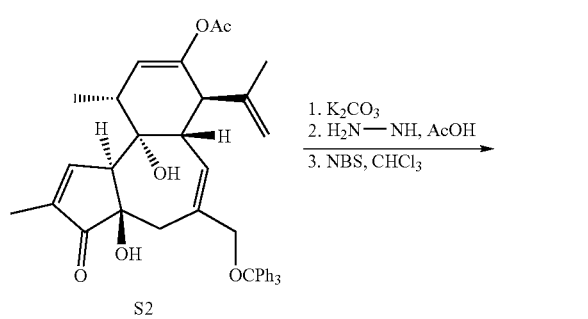

A solution of enol acetate S2 (20 mg, 0.031 mmol) is stirred in methanol (2 ml) under air at room temperature. $K_2CO_3$ (5 mg, 1.5 eq) is added in a single portion, and the mixture is stirred vigorously for 10 min until complete conversion to ketone is observed by TLC. Acetic acid (20 µl, 10 eq) and hydrazine hydrate (30 µl, 20 eq.) are added, and the reaction is allowed to stir for 15 min and monitored by TLC (100% ethyl acetate, PA Stain). Following complete consumption of the starting material, the reaction mixture was diluted with ethyl acetate (2 ml) and quenched by addition of aqueous $NaHCO_3$ (2 ml). The organic phase is removed and the aqueous phase is extracted with ethyl acetate (3×2 ml). The combined organic phase is washed with brine, dried over sodium sulfate (s), and concentrated under reduced pressure to give the crude hydrazone. The crude hydrazone is resuspended in a mixture of toluene/DIPEA (1 ml, 9:1, v/v) in a Teflon-capped sealed tube under argon. The mixture is heated to 150° C. for 16 hours. After cooling, the solvent was removed under reduced pressure, and the vessel backfilled with argon. Exposure of the crude pyrazoline to air must be avoided. The crude is redissolved in chloroform (2 ml), and a pre-mixed solution of N-bromosuccinimide (10 mg, 5 eq.) in chloroform (2 ml, pre-mixed for 10 min at ambient temperature) is added dropwise over 1 min at 0° C. The mixture is stirred at 0° C. for 10 min until TLC indicates complete consumption of the pyrazoline. The reaction is quenched with aqueous $NaHCO_3$ (saturated, 2 ml), and extracted with dichloromethane (3×2 ml). The combined organic layers are dried over $Na_2SO_4$, filtered to remove drying agent, and concentrated under reduced pressure. The residue is subjected to flash chromatography to give a colorless foam (10.1 mg, 47%) The product is characterized by:

TLC $R_f$=0.29 (20% EtOAc/petroleum ether), one purple spot stained by p-anisaldehyde (visible under UV lamp)

$[\alpha]_D^{23.5}$=−43.7° (c 0.50, $CH_2Cl_2$)

$^1$H NMR (500 MHz, $CDCl_3$): δ 7.52-7.55 (m, 6H, Ar—H), 7.12-7.13 (m, 6H, Ar—H), 7.03-7.06 (m, 4H, Ar—H and C1-H), 5.57 (d, 1H, J=4.0 Hz, C7-H), 3.51 (s, 2H, C20-H), 3.10 (dd, 1H, J=11.8 Hz, 5.0 Hz), 2.70 (s, 1H, C10-H), 2.56 (d, 1H, J=8.4 Hz, C14-H), 2.45 (dd, 1H, J=15.4 Hz, C12-H), 2.31 (m, 1H, C11-H), 2.10 (d, 1H, J=18.5 Hz, C5-H), 1.98 (dd, 1H, J=15.4 Hz, 8.5 Hz, C12-H), 1.92 (s, 1H, OH), 1.87 (d, 1H, J=19.0 Hz, C5-H), 1.58 (dd, 3H, J=2.8 Hz, 1.3 Hz, C19-H), 1.54 (s, 3H, gem-Me), 1.36 (s, 3H, gem-Me), 1.37 (s, 1H, OH), 1.17 (d, 3H, J=7.5 Hz, C18-H) ppm.

$^{13}$C NMR (125 MHz, $CDCl_3$): δ 207.0, 156.1, 144.4, 137.9, 136.4, 128.9, 128.5, 127.4, 126.3, 102.5, 92.9, 87.3, 77.6, 73.3, 68.6, 57.3, 52.7, 41.2, 41.1, 38.9, 32.8, 28.7, 23.4, 17.2, 10.1 ppm.

FT-IR (thin film): ν 3412, 2921, 1705, 1448, 1054, 706 $cm^{-1}$.

HRMS: Calcd.: 703.2142 (for [M+Na] $C_{39}H_{41}BrN_2NaO_4$). Found: 703.2147

Example 25

Removal of Trityl Protecting Group

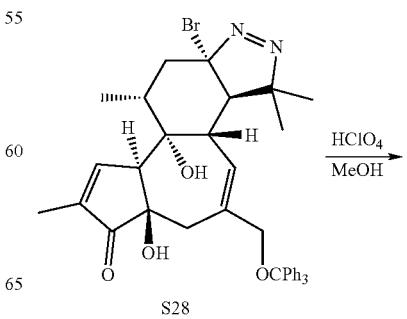

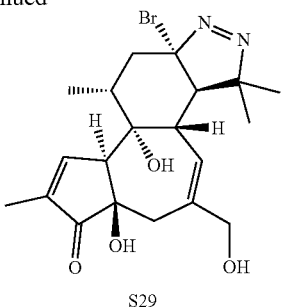

Pyrazoline S28 (68 mg, 0.1 mmol) is dissolved in dry methanol (2 ml) in a round bottom flask equipped with a magnetic stir bar at room temperature, and $HClO_4$ (20 µl, 70% in $H_2O$) is added. The reaction is allowed to stir at ambient temperature until TLC indicates complete consumption of the starting material. The mixture is neutralized by addition of solid $NaHCO_3$, diluted with EtOAc and filtered through a pad of CELITE®. The crude filtrate is concentrated under reduced pressure, and purified by flash chromatography. The usual analysis of the product confirms that the desired product S29 is present.

Example 26

Formation of Cyclopropane Ring Structure

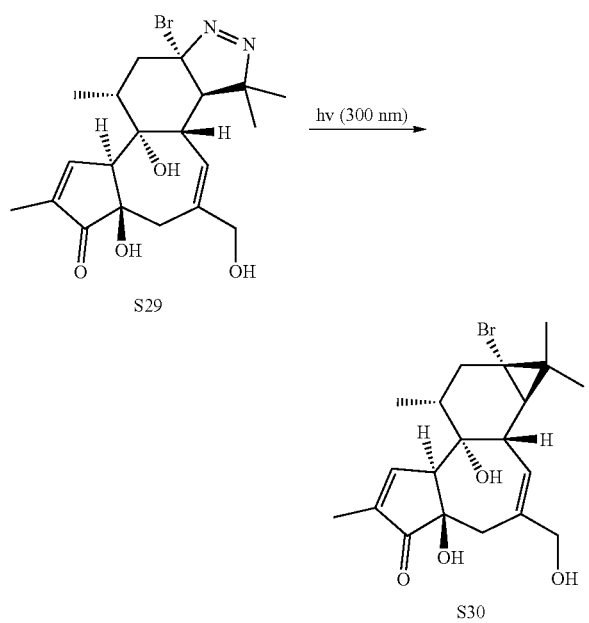

Pyrazoline S29 (44 mg, 0.1 mmol) is dissolved in a mixture of benzene and ethyl acetate (2 ml, 1:1, v/v) at room temperature in a disposable glass vial flushed with argon. The solution is irradiated with UV light (300 nm) using a Rayonet photochemical reactor at room temperature until TLC indicates complete consumption of the starting material. The reaction mixture is concentrated under reduced pressure, and the crude residue is purified by flash column chromatography. The usual analysis confirms that the desired 13-deoxy-13-bromoprostratin (S30) is present.

REFERENCES 1. (a) Newman, D. J.; Cragg, G. M. Natural Products as Sources of New Drugs over the Last 25 Years. *J. Nat. Prod.* 2007, 70, 461-477. (b) Newman, D. J.; Cragg, G. M.; Snader, K. M. The influence of natural products upon drug discovery. *Nat. Prod. Rep.* 2000, 17, 215-234
2. (a) Holton, R. A.; Somoza, C.; Kim, H. B.; Liang, F.; Biediger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. K.; Gentile, L. N.; Liu, J. H. First Total Synthesis of Taxol. 1. Functionalization of the B Ring. *J. Am. Chem. Soc.* 1994, 116, 1597-1598
3. See relevant U.S. Pat. No. 5,430,160
4. Wender, P. A.; Badham, N. F.; Conway, S. P.; Floreancig, P. E.; Glass, T. E.; Houze, J. B.; Krauss, N. E.; Lee, D.; Marquess, D. G.; McGrane, P. L.; Meng, W.; Natchus, M. G.; Shuker, A. J.; Sutton, J. C.; Taylor, R. E. The Pinene Path to Taxanes. 6. A Concise Stereocontrolled Synthesis of Taxol. *J. Am. Chem. Soc.* 1997, 119, 2757
5. Nicolaou, K. C.; Yang, Z.; Liu, J. J.; Ueno, H.; Nantermet, P. G.; Guy, R. K.; Claiborne, C. F.; Renaud, J.; Couladouros, E. A.; Paulvannan, K.; Sorensen, E. J. Total Synthesis of Taxol. *Nature,* 1994, 367, 630-634
6. Danishefsky, S. J.; Masters, J. J.; Young, W. B.; Link, J. T.; Snyder, L. B.; Magee, T. V.; Jung, D. K.; Isaacs, R. C. A.; Bornmann, W. G.; Alaimo, C. A.; Coburn, C. A.; Di Grandi, M. J. Total Synthesis of Baccatin III and Taxol. *J. Am. Chem. Soc.* 1996, 118, 2843-2859
7. Morihira, K.; Hara, R.; Kawahara, S.; Nishimori, T.; Nakamura, N.; Kusama, H.; Kuwajima, I. Enantioselective Total Synthesis of Taxol. *J. Am. Chem. Soc.* 1998; 120, 12980-12981.
8. Mukaiyama, T; Shiina, I; Iwadare, H; Saitoh, M; Nishimura, T; Ohkawa, N; Sakoh, H; Nishimura, K; Tani, Y; Hasegawa, M; Yamada, K; Saitoh, K Asymmetric Total Synthesis of Taxol (R). *Chem. Eur. J.* 1999, 5, 121-161.
9. (a) Gustafson, K. R; Cardellina, J. H., 2nd; McMahon, J. B.; Gulakowski, R. J.; Ishitoya, J.; Szallasi, Z.; Lewin, N. E.; Blumberg, P. M.; Weislow, O, S.; Beutler, J. A.; et al., A non promoting phorbol from the Samoan medicinal plant *Homalanthus nutans* inhibits cell killing by HIV-1. *J. Med. Chem.* 1992, 35, 1978-1986. (b) Wang, Y. B.; Huang, R.; Wang, H. B.; Jin, H. Z.; Lou, L. G.; Qin, G. W. Diterpenoids from the roots of *Euphorbia fischeriana. J. Nat. Prod.* 2006, 69, 967-970.
10. UNAIDS/WHO "AIDS Epidemic Update: December 2007", available at data.unaids.org/pub/EPISlides/2007/2007_epiupdate_en.pdf
11. (a) Blankson, J. N.; Persaud, D.; Siliciano, R. F. The challenges of viral reservoirs in HIV-1 infection. *Ann. Rev. Med.* 2002, 53, 557-593. (b) Yang, Q. E. Eradication of HIV in infected patients: some potential approaches. *Med. Sci. Monit.* 2004, 10, 155-65.
12. Cashmore, A. R.; Seelye, R. N.; Cain, B. F.; Mack, H.; Schmidt, R.; Hecker, E. The Structure of Prostratin: A Toxic Tetracyclic Diterpene Ester From *Pimelea-Prostrata. Tetrahedron Lett.* 1976, 20, 1737-1738.
13. Miana, G. A.; Bashir, M.; Evans, F. J. Isolation of Prostratin from *Euphorbia cornigera. Planta Med.* 1985, 51, 353-354.
14. (a) Gulakowski, R. J.; McMahon, J. B.; Buckheit, R. W., Jr.; Gustafson, K. R.; Boyd, M. R. Antireplicative and anti cytopathic activities of prostratin, a non-tumor-promoting phorbol ester, against human immunodeficiency virus (HIV). *Antiviral Res* 1997, 33, 87-97.

(b) Turley, R. R; Estes, J. D.; Burton, G. F.; Robison, R. A. Down-regulation of HIV-1 receptors and inhibition of HIV-1 entry by prostratin treatment. *J. Hum. Virol.* 2001, 4, 155.

(c) Witvrouw, M.; Pannecouque, C.; Fikkert, V.; Hantson, A.; Van Remoortel, B.; Hezareh, M.; De Clercq, E.; Brown, S. J. Potent and selective inhibition of HIV and SIV by prostratin interacting with viral entry. *Antivir. Chem. Chemother.* 2003, 14, 321-328.

(d) Hezareh, M.; Moukil, M. A.; Szanto, L; Pondarzewski, M.; Mouche, S.; Chemx, N.; Brown, S. J.; Carpentier, J. L.; Foti, M. Mechanisms of HIV receptor and co-receptor down-regulation by prostratin: role of conventional and novel PKC isoforms. *Antivir. Chem. Chemother.* 2004, 15, 207-222.

(e) Rullas, J.; Bermejo, M.; Garcia-Perez, J.; Beltan, M.; Gonzalez, N.; Hezareh, M.; Brown, S. J.; Alcami, J. Prostratin induces HIV activation and downregulates HIV receptors in peripheral blood lymphocytes. *Antivir. Ther.* 2004, 9, 545-554.

15. (a) Kulkosky, J.; Culnan, D. M.; Roman, J.; Dornadula, G.; Schnell, M.; Boyd, M. R.; Pomerantz, R. J. Prostratin: activation of latent HIV-1 expression suggests a potential inductive adjuvant therapy for HAART. *Blood* 2001, 98, 3006-3015.

(b) Korin, Y. D.; Brooks, D. G.; Brown, S.; Korotzer, A.; Zack, J. A. Effects of prostratin on T-cell activation and human immunodeficiency virus latency. *J. Virol.* 2002, 76, 8118-8123.

(c) Kulkosky, J.; Sullivan, J.; Xu, Y.; Souder, E.; Hamer, D. H.; Pomerantz, R. J. Expression of latent HAART-persistent HIV type 1 induced by novel cellular activating agents. *AIDS Res. Hum. Retroviruses* 2004, 20, 497-505.

16. (a) Gustafson, K. R.; Cardellina, J. H., 2nd; McMahon, J. B.; Gulakowski, R. J.; Ishitoya, J.; Szallasi, Z.; Lewin, N. E.; Blumberg, P. M.; Weislow, O, S.; Beutler, J. A.; et al., A nonpromoting phorbol from the Samoan medicinal plant *Homalanthus nutans* inhibits cell killing by HIV-1. *J. Med. Chem.* 1992, 35, 1978-1986.

(b) Szallasi, Z.; Krsmanovic, L.; Blumberg, P. M. Nonpromoting 12-deoxyphorbol 13-esters inhibit phorbol 12-myristate 13-acetate induced tumor promotion in CD-1 mouse skin. *Cancer Res.* 1993, 53, 2507-2512.

17. Bocklandt, S.; Blumberg, P. M.; Hamer, D. H. Activation of latent HIV-1 expression by the potent antitumor promoter 12-deoxyphorbol 13-phenylacetate. *Antiviral Res.* 2003, 59, 89-98

18. Burdelya, L. G.; Krivokrysenko, V. I.; Tallant, T. C.; Strom, E.; Gleiberman, A. S.; Gupta, D.; Kumasov, O. V.; Fort, F. L.; Osterman, A. L.; DiDonato, J. A.; Feinstein, E.; Gudkov, A. V. An agonist of toll-like receptor 5 has radioprotective activity in mouse and primate models *Science*, 2008, 320, 226-230.

19. Johnson, H. Variability in Content of the Anti-AIDS Drug Candidate Prostratin in Samoan populations of *Homalanthus nutans* (Euphorbiaceae). Plants in the Service of Human Health: Continuing the search for new plant-based therapies. Chicago, Ill. 48th Annual Meeting: Jun. 4-7, 2007.

20. In vitro studies indicate that prostratin is active in micromolar concentrations. Taking the estimated oral bioavailability (~28%) and body volume (~50 liter), a patient would need ~50 mg of prost rat in to reach --1 µM prostratin in the body.

21. Cairnes, D. A.; Mirvish, S. S.; Wallcave, L.; Nagel, D. L.; Smith, J. W. A Rapid Method for Isolating Phorbol from Croton Oil *Cancer Lett.* 1981, 14, 86-91.

22. (a) Azam, M. M.; Waris, A.; Nahar, N. M. *Biomass and Bioenergy*, 2005, 29, 293-302. (b) *Alexander's Gas & Oil Connections*, News and Trends: Africa, vol 10, issue 20, Oct. 26, 2005

23. www.berkeley.edu/news/media/releases/2004/09/29_samoa.shtml 24. (a) Wender, P. A.; Kogen, H.; Lee, H. Y.; Munger, J. D.; Wilhelm, R. S.; Williams, P. D. Studies on Tumor Promoters. 8. the Synthesis of Phorbol. *J. Am. Chem. Soc.* 1989, 111, 8957-8958.

(b) Wender, P. A.; McDonald, F. E. Studies on Tumor Promoters. 9. A 2nd-Generation Synthesis of Phorbol. *J. Am. Chem. Soc.* 1990, 112, 4956-4958.

(c) Wender, P. A.; Rice K. D., Schnute M. E. The First Formal Asymmetric Synthesis of Phorbol. *J. Am. Chem. Soc.* 1997, 119, 7897-7898.

(d) Lee K.; Cha, J. K. Formal synthesis of (+)-phorbol. *J. Am. Chem. Soc.* 2001, 123, 5590-5591.

25. Bowry, V. W.; Ingold, K. U. Kinetics of Nitroxide Radical Trapping. 2. Structural effects. *J. Am. Chem. Soc.* 1992, 114, 4992-4996.

26. Bartsch, H.; Hecker, E. Zur Chemie des Phorbols, XI. Crotophorbolon-enolacetat und Acetoxy-crotophorbolon. *Z. Naturforschg.* 1968, 24b, 91-98.

27. For example: Warner, P.; Lu, S.-L. Propellanes. XV. Stereoselectivities of Cyclopropyl Radicals Via Tin Hydride Reduction. *Tetrahedron Lett.* 1976, 51, 4665

28. Appendino, G.; Bertolino, A.; Minassi, A.; Annunziata, R.; Szallasi, A.; Petrocellis, L.; Di Marzo, V. Synthesis and biological evaluation of phorbol-resiniferatoxin (RTX) hybrids. *Eur. J. Org. Chem.* 2004, 16, 3413

29. Davis, B. R.; Woodgate, P. D. Clemmensen Reduction. Part III a, b-unsaturated ketones *J. Chem. Soc. (C)* 1966, 2006-2010.

30. (a) Freeman, J. P. A synthesis of cyclopropyl acetates *J. Org. Chem.* 1964, 29, 1379-1382.

(b) Engel, P. S.; Shen, L. "Photochemical and thermal decomposition of 1-pyrazolines" *Can. J. Chem.* 1974, 52, 4040-4043.

31. Ruano, J. L. G.; Alonso, M.; Frail, U.; Martin, R.; Peromingo, M. T.; Tito, A. Asymmetric synthesis of cyclopropanes from sulfinylpyrazolines mediated by acids *Phosphorus, Sulfur, and Silicon* 2005, 180:1441-1442.

32. Kennedy, G. D.; Baumstark, A. L.; Dotrong, M.; Thomas, T.; Narayanan, N. Thermolysis of Hexasubstituted-4,5-dihydro-3H-pyrazoles: Synthesis of 1-Alkoxy- and 1-Acetoxy-1,2,2,3,3-pentasubstituted-cyclopropanes. *J. Heterocyclic Chem.*, 1991, 28, 1773.

33. Molchanov, A. P.; Korotkov, V. S.; Kopf, J.; Kostikov, R. R. Reactions of substituted ethyl 1,2,3,4,4',5'-hexahydrospiro-[naphthalene-2,5'-pyrazole]-3'-carboxylates with halogens *Russ. J. Org. Chem.* 2005, 41, 1036-1042.

34. Moiseev, A. G.; Neckers, D. C. Stereoselective Synthesis of 3,5-Dialkyl-3,5-dihydro-3,5-diphenyl-4H-pyrazol-4-ones. *Synthesis*, 2005, 17, 2901

35. Tuloup R.; Danion-Bougot, R.; Danion, D.; Pradère, J.-P.; Toupet, L. Une application du cycle pyrazoline à la lactamisation et à la formylation de 6H thiazines-1,3. *Can. J. Chem.* 1989, 67, 1125

CONCLUSION

While only a few embodiments of the invention have been shown and described herein for the production of deoxytilgiane-type compounds or structural or functional analogs thereof, it will become apparent to those skilled in the art that various modifications and changes can be made in the present invention without departing from the spirit and scope of the present invention. All such modification and changes coming within the scope of the appended claims are intended to be carried out thereby. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A process to produce a 12-deoxy tigliane-type compound or a structural analog thereof of the formula:

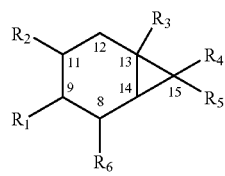

Formula I
wherein
  $R_1$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea;
  $R_2$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea;
  $R_3$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea;
  $R_4$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea;
  $R_5$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea; and
  $R_6$ is selected from the group consisting of hydrogen, alkyl (C1 to C15), cyclic alkyl (C3 to C15), aromatic ring, hydroxyl, carbonate, carbamate, ester, ether, thiol, amine, amide, guanidine and urea;
  with the proviso that $R_1$ and $R_6$ cannot both be hydrogen and wherein $R_1$ and $R_6$ may be connected as in the case of 12-deoxy tigliane-type compounds, or may be disconnected as in the case of structural analogs, said process comprising:
  a) contacting an enolate salt, enol ester, enol ether or a ketone at the position corresponding to C-13 of a compound, said compound possessing structural features of a C ring of a tigliane and possessing a C-14 linked to at least a propenyl group, with hydrazine or an agent equivalent to hydrazine at a temperature between −20 and +150° C. for about 0.1 to about 72 hours;
  b) contacting the product of step a with an organic solvent at approximately +20 to +250° C. to form a pyrazoline product;
  c) contacting the product of step b with an oxidizing agent which is an electron withdrawing compound or nucleophilic agent in an organic solvent at between about −10 to +120° C. for approximately 0.1 to 72 hours to form a product oxidized at said C13 position;
  d) forming from the product of step c) a compound of Formula I by
    1) contacting the product of step c with light of a wavelength that is absorbed by the product in a solvent at between about −20 and +60° C. for between about 1 to 240 min; or
    2) contacting the product of step c with an excited state of a sensitizer formed by absorption of light by the sensitizer; or
    3) contacting the product of step c with a metal or metal salt in an organic solvent at between about −80 and +110° C. for between about 1 and 48 hours; and
  e) isolating the compound of Formula I from the product of step d).

2. The process as set forth in claim 1, wherein $R_2$ is methyl, $R_3$ is an ester —OC(O)Ak, where Ak is an alkyl chain, $R_4$ and $R_5$ are methyl groups, and/or $R_1$ and $R_6$ are connected by a 5 member alkyl chain as in a tigliane skeleton.

3. The process as set forth in claim 1, wherein $R_{1-6}$ groups are straight-chained or branched, and contain one or more heteroatoms selected from the group consisting of boron, nitrogen, oxygen, phosphorous, sulfur, silicon and selenium.

4. The process as set forth in claim 1, wherein step a) is conducted in the presence of a base or an acid.

5. The process as set forth in claim 1, wherein step a) is followed by treatment with a base or a hydrazine scavenger.

6. The process as set forth in claim 1, wherein step b) is conducted in the presence of a base.

7. The process as set forth in claim 1, wherein step c) is conducted in the presence of one of a carboxylic acid, alcohol, thiol, amine, halide, or a combination thereof.

8. The process as set forth in claim 1 wherein step c) is followed by:
  contacting the product of step c) with a nucleophilic agent, an alcohol derivatizing agent or combinations thereof in an organic solvent at between −20 and +150° C. for between 0.1 and 72 hours or with an acid, a base, an oxidizing agent, or a reducing agent; or
  contacting the product of step c) with a nucleophilic agent, an alcohol derivatizing agent or combinations thereof in an organic solvent at between −20 and +150° C. for between 0.1 and 72 hours and then with an acid, a base, an oxidizing agent, or a reducing agent; or
  contacting the product of step c) with an acid, a base, an oxidizing agent, or a reducing agent and then with a nucleophilic agent, an alcohol derivatizing agent or combinations thereof in an organic solvent at between −20 and +150° C. for between 0.1 and 72 hours.

9. The process as set forth in claim 8, wherein said acid is perchloric acid.

10. The process as set forth in claim 1, further comprising:
  contacting the product of step d) with a nucleophilic agent, an alcohol derivatizing agent or combinations thereof in an organic solvent at between −20 and +150° C. for between 0.1 and 72 hours or with an acid, a base, an oxidizing agent, or a reducing agent; or
  contacting the product of step d) with a nucleophilic agent, an alcohol derivatizing agent or combinations thereof in an organic solvent at between −20 and +150° C. for between 0.1 and 72 hours and then with an acid, a base, an oxidizing agent, or a reducing agent; or contacting the product of step d) with an acid, a base, an oxidizing agent, or a reducing agent and then with a nucleophilic agent, an alcohol derivatizing agent or combinations thereof in an organic solvent at between −20 and +150° C. for between 0.1 and 72 hours.

11. The process as set forth in claim 10, wherein said acid is perchloric acid.

12. The process as set forth in claim 1, further comprising:
obtaining a compound for use in step a) that is phorbol, phorbol-20-trityl ether or crotophorbolone; and
contacting an obtained compound from the preceding step with a derivatizing agent, an acid agent, or a base agent at approximately −20 to 150° C. for between about 1 to 72 hr to produce an enol derivative or ketone at the position corresponding to C13 of a tigliane.

13. The process as set forth in claim 12, wherein the obtained compound is protected at positions corresponding to C-13 and/or C-20 of a tigliane or combinations thereof.

14. The process as set forth in claim 12, further comprising contacting the enol derivative or ketone with an oxidizing agent, a nucleophilic agent, or a reducing agent at approximately +10 to +100° C. for approximately 0.1 to 72 hours.

15. The process as set forth in claim 12, wherein said obtained compound is a phorbol analog or a precursor thereof.

16. The process as set forth in claim 15, wherein said obtained compound is protected at positions corresponding to C-13, C-20 of a tigliane.

17. The process as set forth in claim 16, wherein protecting groups are removed by an acid agent or a base agent.

18. The process as set forth in claim 12, wherein said derivatizing agent, acid or base agent is methanesulfonyl chloride in pyridine.

19. The process as set forth in claim 12, wherein said derivatizing agent, acid or base agent is hydrazine hydrate.

20. The process as set forth in claim 1, wherein said 12-deoxy tigliane-type compound is prostratin or 12-deoxy-phorbol-13-phenylacetate (DPP).

21. The process as set forth in claim 1, wherein step a) is carried out with hydrazine hydrate in the presence of potassium carbonate, followed by acetic acid.

22. The process as set forth in claim 1, wherein the product of step a) is treated with basic alumina.

23. The process as set forth in claim 1, wherein step b) is carried out in a mixture of N,N-diisopropyl ethylamine and toluene.

24. The process as set forth in claim 1, wherein said oxidizing agent in step c) is lead (IV) acetate.

25. The process as set forth in claim 1, wherein said oxidizing agent in step c) is iodosobenzene diacetate (PhI(OAc)$_2$).

26. The process as set forth in claim 1, wherein said oxidizing agent in step c) is premixed with phenylacetic acid.

27. The process as set forth in claim 1, wherein step c) is conducted in the presence of a mixture of carboxylic acids selected from the group consisting of primary alkyl, secondary alkyl, tertiary alkyl and aromatic organic carboxylic acids.

28. The process as set forth in claim 1, wherein step c) is conducted in the presence of a mixture of alcohols selected from the group consisting of primary alkyl, secondary alkyl, tertiary alkyl and aromatic alcohols.

29. The process as set forth in claim 1, wherein said nucleophilic agent in step c) is hydrogen cyanide.

30. The process as set forth in claim 1, where the preferred wavelength of light used in step d) is between 300 and 370 nm.

31. The process as set forth in claim 1, wherein $R_1$ and $R_6$ together comprise a ring structure whereby Formula I is a tigliane.

32. The process as set forth in claim 31, wherein $R_2$ is lower alkyl, $R_3$ is ester, $R_4$ is lower alkyl and $R_5$ is lower alkyl.

* * * * *

UNITED STATES PATENT AND TRADEMARK OFFICE
CERTIFICATE OF CORRECTION

| | | |
|---|---|---|
| PATENT NO. | : 8,067,632 B2 | Page 1 of 1 |
| APPLICATION NO. | : 12/178860 | |
| DATED | : November 29, 2011 | |
| INVENTOR(S) | : Wender et al. | |

It is certified that error appears in the above-identified patent and that said Letters Patent is hereby corrected as shown below:

In the Specification Under Column 1:

• Please replace Column 1, line no. 12-16 with:

-- FEDERALLY-SPONSORED RESEARCH OR DEVELOPMENT
This invention was made with Government support under contract CA031841 awarded by the National Institutes of Health. The Government has certain rights in this invention. --

Signed and Sealed this
Nineteenth Day of June, 2012

David J. Kappos
*Director of the United States Patent and Trademark Office*